US005585637A

United States Patent [19]
Bertelsen et al.

[11] Patent Number: 5,585,637
[45] Date of Patent: Dec. 17, 1996

[54] MULTI-HEAD NUCLEAR MEDICINE CAMERA FOR DUAL SPECT AND PET IMAGING

[75] Inventors: Hugo Bertelsen, Pleasanton; Horace H. Hines, San Jose; Matthew J. Murphy, Los Altos; Peter Nellemann; Donald R. Wellnitz, both of Pleasanton, all of Calif.

[73] Assignee: ADAC Laboratories, Milpitas, Calif.

[21] Appl. No.: 488,926

[22] Filed: Jun. 9, 1995

[51] Int. Cl.⁶ .......................... G01T 1/164; G01T 1/208
[52] U.S. Cl. .............................. 250/363.03; 250/363.04; 250/369
[58] Field of Search ..................... 250/363.03, 363.04, 250/369

[56] References Cited

U.S. PATENT DOCUMENTS 4,057,727  11/1977  Muehllehner et al. ............ 250/363.03
5,493,120  2/1996   Geagan .............................. 250/363.02

FOREIGN PATENT DOCUMENTS 2052207  1/1981  United Kingdom ............. 250/363.03

OTHER PUBLICATIONS

A. M. J. Paans, et al., "Performance Parameters of a Longitudinal Tomographic Positron Imaging System," reprinted from Nuclear Instruments & Methods, vol. 192, pp. 491–500 (1982).

G. Muehllehner, et al., "Performance Parameters of a Positron Imaging Camera," IEEE Transactions on Nuclear Science, vol. NS–23, No. 1, pp. 528–537 (Feb. 1976).

M. Tanaka, Y. Hirose, K. Koga, H. Hattori, "Engineering Aspects of a Hybrid Emission Computed Tomograph" *IEEE Trans. Nuc. Sci.* vol. 28, No. 1 (Feb. 1981) pp. 137–141.

*Primary Examiner*—Constantine Hannaher
*Attorney, Agent, or Firm*—Blakely, Sokoloff, Taylor and Zafman

[57]   ABSTRACT

A multi-detector head nuclear camera system automatically switchable (and optimized) to perform either SPECT imaging or PET imaging. The camera system employs, in one embodiment, multi-detector configuration having dual head scintillation detectors but can be implemented with more than two detector heads. The detectors contain switchable triggering circuitry so that coincidence detection for PET imaging and non-coincidence detection for SPECT imaging is available. Using a variable integration technique with programmable integration interval, the event detection and acquisition circuitry of the camera system is switchable to detect events of different energy distribution and count rate which are optimized for PET and SPECT imaging. The system also includes dual integrators on each scintillation detector channel for collecting more than one event per detector at a time for PET or SPECT mode. In PET or SPECT mode, the system also employs variable PMT cluster sizing having smaller cluster sizes for PET imaging and relatively larger cluster sizes for SPECT. In PET or SPECT mode, the system also employs variable centroid shape and zonal triggering. Utilizing the above programmable settings, the camera system can be automatically configured to operate in either SPECT or PET imaging modes.

49 Claims, 32 Drawing Sheets

335

| PEAK PMT ADDRESS | TYPE | ANALOG GLOBAL ENERGY DATA BUFFER ADDRESS → COUNT → | | | | | | | | | | | | | |
|---|---|---|---|---|---|---|---|---|---|---|---|---|---|---|---|
| | | 0 | 1 | 2 | 3 | 4 | 5 | 6 | 7 | 8 | 9 | 10 | 11 | 12 | ...13 | n |
| 0 | | | | | | | | | | | | | | | | |
| ... | | | | | | | | | | | | | | | | |
| 7 | NORMAL | 55 | 1 | 8 | 20 | 19 | 3 | 6 | 18 | STOP | | | | | | |
| ... | | | | | | | | | | | | | | | | |
| 38 | EDGE | 55 | 22 | 23 | 39 | 37 | STOP | | | | | | | | | |
| ... | | | | | | | | | | | | | | | | |
| 46 | CORNER | 55 | 41 | 42 | 43 | STOP | | | | | | | | | | |
| ... | | | | | | | | | | | | | | | | |
| 54 | | | | | | | | | | | | | | | | |

FIG. 8

CENTROID TYPE

345

| PMT ADDRESS | NORMAL | SHORT EDGE | LONG EDGE | CORNER | AUX TYPE 1 | AUX TYPE 2 |
|---|---|---|---|---|---|---|
| 0 | Wx / Wy | Wx / Wy | Wx / Wy | Wx / Wy | Wx / Wy | Wx / Wy |
| 1 | Wx / Wy | Wx / Wy | Wx / Wy | Wx / Wy | Wx / Wy | Wx / Wy |
| 2 | Wx / Wy | Wx / Wy | Wx / Wy | Wx / Wy | Wx / Wy | Wx / Wy |
| 3 | Wx / Wy | Wx / Wy | Wx / Wy | Wx / Wy | Wx / Wy | Wx / Wy |
| 4 | Wx / Wy | Wx / Wy | Wx / Wy | Wx / Wy | Wx / Wy | Wx / Wy |
| 5 | Wx / Wy | Wx / Wy | Wx / Wy | Wx / Wy | Wx / Wy | Wx / Wy |
| ⋮ | | | | | | |
| 54 | Wx / Wy | | Wx / Wy | Wx / Wy | Wx / Wy | Wx / Wy |

FIG. 9

ENERGY NORMALIZED

| PMT # | NEAR PMTS | FAR PMTS |
|---|---|---|
| 0 | (6% ⟶ 0.17%) | (=0%) |
| 1 | | |
| 2 | | |
| ⋮ | | |
| 54 | | |

MULTI-HEAD NUCLEAR MEDICINE CAMERA FOR DUAL SPECT AND PET IMAGING

BACKGROUND OF THE INVENTION (1) Field of the Invention

The present invention relates to the field of nuclear medicine systems. Specifically, the present invention relates to signal processing systems for scintillation detectors.

(2) Prior Art

Gamma cameras performing Single Photon Emission Computed Tomography (SPECT) have been utilized in nuclear medicine for some time. Anger proposed and developed such a system in the 1950s which has been modified and improved extensively with the introduction of high speed digital computer systems for image acquisition as well as image reproduction. However, SPECT camera systems utilize a collimator that is installed in front of the scintillation crystal within a scintillation detector. The collimator is used to collimate the incoming gamma rays so that only rays of a certain angle of incidence actually penetrate the crystal. Although SPECT imaging is extensively used in nuclear medicine and provides beneficial image quality, the collimator introduces a source of image degradation in nuclear medicine images and tends to somewhat reduce the resolution and quality of images acquired by SPECT systems.

Cameras performing Positron Emission Tomography (PET) have been utilized in nuclear medicine as well with the introduction of relatively high speed detection electronics and computer systems for image acquisition and processing. These PET camera systems utilize a form of the scintillation detector that is used in SPECT systems, however, they do not utilize a collimator. In PET systems, the detection of two gamma rays in coincidence (in different scintillation detectors) is used to compute imaging information. A PET system employing two scintillation detectors is described in a paper presented by Gerd Muehllehner, M. P. Buchin, and J. H. Dudek entitled "Performance Parameters of a Positron Imaging Camera," published in the IEEE Transactions on Nuclear Science, Volume NS-23, No. 1, on February 1976 and also in a paper entitled "Performance Parameters of a Longitudinal Tomographic Positron Imaging System" by Paans, deGraaf, Welleweerd, Vaalburg and Woldring, in Nuclear Instruments and Methods, Volume 192, Nos 2, 3, on Feb. 1, 1982 pages 491–500. By utilizing higher energy gamma rays and eliminating the collimators, PET systems offer greatly improved image resolution and image quality over SPECT systems. Because the collimators are removed in PET systems, the detected count rate is higher in PET cameras over SPECT camera systems. Although both camera systems utilize different detection electronics and other circuitry, both PET and SPECT systems employ scintillation detectors.

The detection hardware for SPECT and PET systems is different in terms of the manner in which the systems detect and record events and is also different because PET systems operate at higher count rates over SPECT systems. Further, SPECT systems employ a different radionuclide over PET systems and detect gamma rays at different energy levels over PET systems. For this reason, although SPECT and PET systems are versatile and useful within nuclear medicine, in the prior art, different camera systems have been implemented and supplied for PET and SPECT imaging. Therefore, a facility desiring to perform SPECT and PET imaging is required to acquire two separate camera systems at a relatively greater expense.

It would be advantageous, then, to provide a nuclear camera system offering the ability to perform both SPECT and PET imaging techniques within a single configurable system. Therefore, the expense of acquiring two separate systems can be advantageously avoided. The present invention offers such advantageous capabilities.

Accordingly, it is an object of the present invention to provide a single dual head nuclear camera system that is switchable between SPECT imaging and PET imaging to perform either mode of operation. It is an object of the present invention to provide such a system employing high count rate event detection circuitry for PET studies and also switchable to offer detection of gamma rays of different energy distributions, one for SPECT imaging and one for PET imaging. It is also an object of the present invention to provide a scintillation detector pair having switchable triggering capabilities that can be used to detect and record SPECT events and also switched to perform coincidence detection for PET imaging. It is yet another object of the present invention to employ zonal triggering capabilities for event detection in both SPECT or PET imaging modes. These and other objects of the present invention not specifically recited will become clear within discussions of the present invention herein.

SUMMARY OF THE INVENTION

A multi-detector head nuclear camera system automatically switchable (and optimized) to perform either SPECT imaging or PET imaging is described. The camera system employs, in one embodiment, multi-detector configuration having dual head scintillation detectors but can be implemented with more than two detector heads. The detectors contain switchable triggering circuitry so that coincidence detection for PET imaging and non-coincidence detection for SPECT imaging is available and can be automatically selected. Using a variable integration technique with programmable integration interval, the event detection and acquisition circuitry of the camera system is switchable to detect events of different energy distribution and count rate which are optimized for PET and SPECT imaging. In one mode a relatively larger integration interval is selected for SPECT imaging and a relatively shorter integration interval is selected for PET mode. The system also includes dual integrators on each scintillation detector channel for collecting more than one event per detector at a time for either PET or SPECT mode. In PET or SPECT mode, the system also employs variable PMT cluster sizing having smaller cluster sizes for PET imaging and relatively larger cluster sizes for SPECT. In PET or SPECT mode, the system also employs variable centroid shape and zonal triggering. Utilizing the above programmable settings, the camera system can be automatically configured to operate in either SPECT or PET imaging modes.

When instructed to operate in SPECT mode, under computer control, the camera system automatically loads the longer integration interval into the detectors, programs a PMT address table to allow larger sized clusters to be generated, queues for installation of the collimators, and automatically sets the trigger detection mode to non-coincidence. When instructed to operate in PET mode, under computer control, the camera system automatically loads the shorter integration interval into the detectors, programs a PMT address table to only allow smaller sized clusters to be generated, queues for removal of the collimators, and automatically sets the trigger detection mode to coincidence detection. In SPECT mode, SPECT reconstruction procedures are applied and in PET mode, PET reconstruction procedures are applied.

BRIEF DESCRIPTION OF THE DRAWINGS

FIG. 2A1 illustrates event detection/trigger generation circuitry used by the dual head camera system of the present invention operating in SPECT mode of operation.

FIG. 2A2 illustrates event detection/trigger generation circuitry used by the dual head camera system operating in PET or coincidence mode of operation.

FIG. 2A3 illustrates circuitry of the coincidence timing circuit utilized by the camera system of the present invention to provide switchable SPECT/PET triggering mechanisms for generation of valid event triggering signals.

FIG. 3 is an illustration of a weighted centroid computation for determining the spatial coordinates of an event used by the present invention.

FIG. 8 is an illustration of the programmable PMT address table circuit of the present invention Digital Event Processor.

FIG. 9 is an illustration of the x and y weight table circuit of the present invention Digital Event Processor.

FIG. 18 illustrates the memory circuit of the present invention for providing far PMT addresses based on an input peak PMT address.

MULTI-HEAD NUCLEAR MEDICINE CAMERA
FOR DUAL SPECT AND PET IMAGING

DETAILED DESCRIPTION OF THE
INVENTION

In the following detailed description of the present invention numerous specific details are set forth in order to provide a thorough understanding of the present invention. However, it will be obvious to one skilled in the art that the present invention may be practiced without these specific details. In other instances well known methods, procedures, components, and circuits have not been described in detail as not to unnecessarily obscure the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. Unless specifically stated otherwise as apparent from the following discussions, it is appreciated that throughout the present invention, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Figure 1:
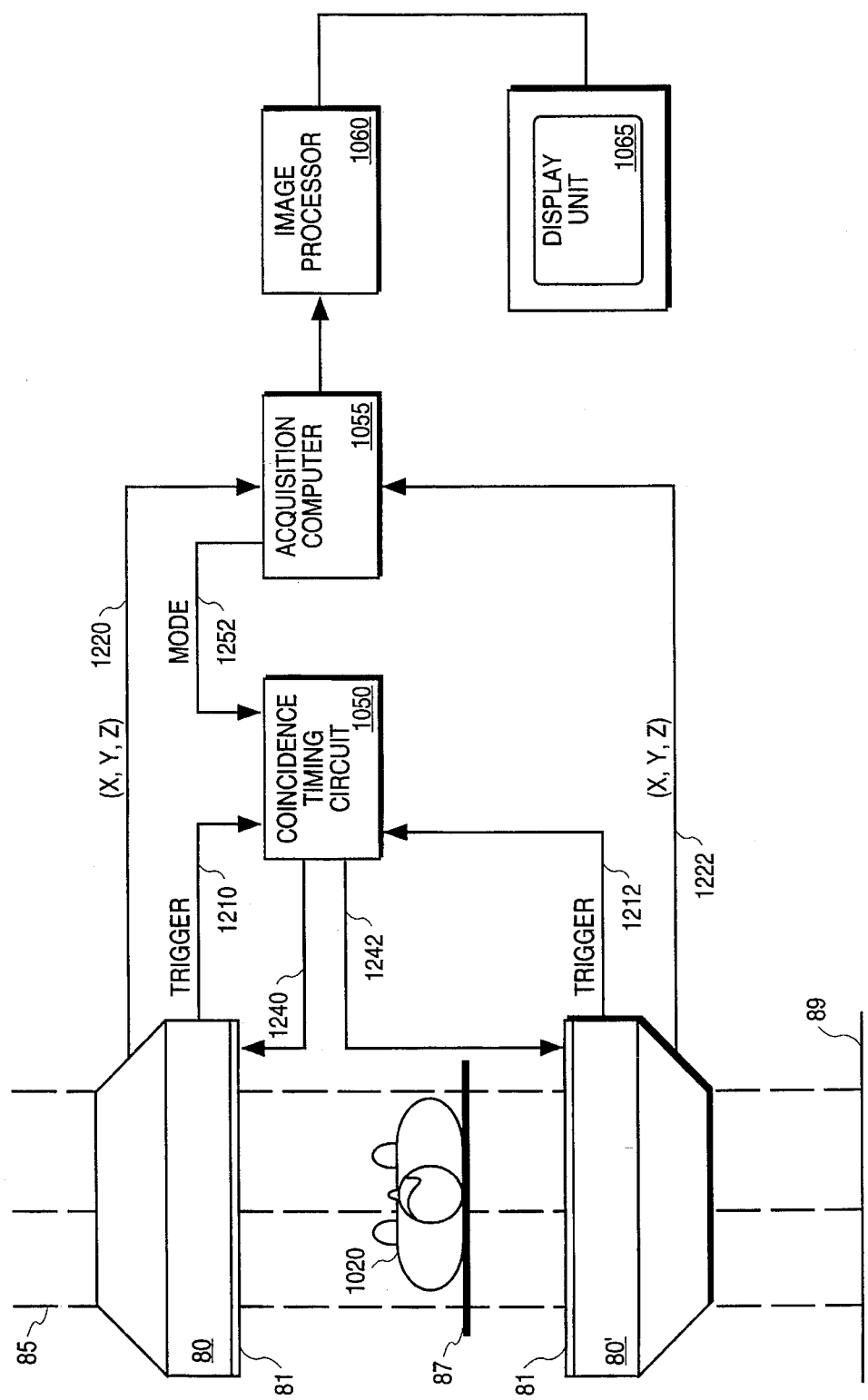
FIG. 1 illustrates a high level block diagram of a dual head gamma camera system employing both SPECT and PET operational modes, an acquisition computer and an image processor of he present invention.

The various embodiments of the present invention described herein are used in conjunction with a dual head scintillation detector camera system switchable between SPECT and PET imaging modes of operation. With reference to FIG. 1, a high level diagram of a dual head detector gamma camera system of the present invention is shown. Although an embodiment of the present invention is described with respect to a two detector camera system, it is appreciated that the teachings of the present invention can be extended to cover systems having more than two detectors (e.g., a triple head camera system is contemplated). Generally, the system of the present invention includes a pair of gamma camera detectors 80 and 80' ("dual head") composed of a plurality of photomultiplier tubes, PMTs, arranged in a two dimensional matrix convention and optically coupled to a glass plate to receive light (e.g., visible photons) from a crystal layer 81. The PMT array creates a photodetector. The crystal layer can be composed of sodium iodine, NaI, and is typically located between a collimator (not shown) and the PMT array. The collimator applied to each detector is used for SPECT imaging modes, but not for PET imaging modes, and is typically manufactured from a number of holes with lead septas arranged in a honeycomb convention to collimate gamma rays that strike the crystal 81. The detector pair are shown in a 180 degree configuration and can rotate with respect to each other such that they are at a 90 degree configuration.

Gamma rays that strike the NaI(TI) crystal 81 cause well known scintillation events that release a number of visible light photons that are detected by the PMTs with different light intensifies. Each PMT reports in the form of an analog signal indicative of the amount of light energy detected as a result of the scintillation event. In the present invention, these signals are digitized at an early circuit stage and are processed digitally. The gamma camera detectors 80 and 80' utilized within the scope of the present invention are of the Anger type and can be of a number of well known and commercially available designs and therefore some details of such a gamma detector will not be discussed in depth herein. However, as will be discussed herein, the present invention provides many enhancements in the image acquisition and processing of detected events so that the camera system can operate in either SPECT or PET image mode. An exemplary gamma camera detector used by one embodiment of the present invention can contain as many as 55 or 108 PMTs. A detector of the pair can also utilize smaller diameter PMTs along the edges to increase the detector's field of view. An embodiment of the present invention utilizes forty-nine 76 mm round PMTs and six 51 mm round PMTs for edge filling, however, the number of PMTs, their sizes and their configurations can be varied within the scope of the present invention.

It is appreciated that each detector, either 80 or 80' is similarly constructed and that discussions with respect to one detector are applicable to both.

The detector pair 80 and 80' of FIG. 1 are mounted on a gantry 85 which can rotate the detectors 80 and 80' in various orbits around an object (patient) 1020 resting on table 87 (e.g., for ECT scanning operations). In either configuration (180 or 90 degrees), the detector pair can rotate about a center of rotation through a number of projection angles, as is known in gamma camera technology. The gantry 85 and table 87 rest on base 89. The detector pair 80 and 80' can also be directed transversely across the table 87 (e.g., for total body scanning operations) or placed over the patient 1020 for static imaging.

Upon an event detection in either detector 80 or 80', signals 1210 and 1212, respectively, carry trigger pulses to a programmable coincidence timing circuit 1050 (CTC). The CTC unit 1050 then generates valid event trigger signals over lines 1240 and 1242, respectively, for the detectors 80 and 80' depending on the mode of operation (either SPECT or PET). A signal carried over line 1252 indicates to the CTC unit 1050 the proper mode of operation (SPECT or PET). The valid event trigger signals 1240 and 1242 are used by the detectors to start (or reset) their accumulators (integrators) which accumulate (integrate) the energy of the detected scintillation and are therefore called "valid event" trigger signals. In the PET mode, integration is not started until a coincidence is detected between detector 80 and 80'. In SPECT mode, an integration is started for each detector upon a trigger event, regardless of coincidence. After integration and centroiding, the detectors 80 and 80' output an X, Y, and Z value over lines 1220 and 1222, respectively. These signals indicate the coordinate value (X, Y) ("localization") of the detected event with respect to the detector and its measured energy value, Z.

Within embodiments that utilize more than two detector heads, event detection information from each detector head is forwarded to the CTC unit 1050 that then detects coincidence between any two detectors feeding the CTC event detection information (when in PET imaging mode). In SPECT mode, each detector reports event information in non-coincidence in a similar fashion as the dual detector system.

Although the location of such hardware is not material to the present invention, hardware is included within each detector for digitizing the PMT channel signals, correcting them, and outputting X, Y, and Z values as will be discussed further below. To this extent, each detector 80 and 80' contains preamplification and digitization hardware as well as a Digital Event Processor. These are discussed further below. This hardware can be located within or outside the scintillation detector 80 and 80'.

The values transmitted over bus 1220 and 1222 are input to an acquisition computer system 1055 which contains a general purpose digital computer system 1112 (FIG. 5) as described to follow. The acquisition computer 1055 stores the values for each detected event for each projection angle and this information is routed to an image processor 1060 which contains a standard user interface. The user interface provides a user input device for indicating which mode of operation (e.g. SPECT or PET) is requested. This device can also be located in computer 1055. The image processor 1060 performs image reconstruction and attenuation and uniformity correction based on the acquired event data for SPECT or PET imaging modes. The image processor 1060 is also coupled to a display unit 1065 (which can include a hardcopy device) for visualizing images captured by the camera system.

DETECTOR ELECTRONICS

The circuitry and logic of each detector 80 and 80' for signal processing is further illustrated within the following figures: FIG. 2A1, FIG. 2A2, FIG. 2B, FIG. 2C and FIG. 2D. It is appreciated that this circuitry can alternatively be located outside the detector heads 80 and 80' or partially spread inside and partially outside of the detector heads 80 and 80'. It is further appreciated that the acquisition computer 1055 also comprises a general purpose computer system 1112 (see FIG. 5) as will be discussed in more detail. An embodiment of the present invention can also be implemented utilizing discrete electronic components in lieu of a general purpose computer system.

TRIGGER DETECTION AND SWITCHABLE PET AND SPECT EVENT RECOGNITION

Since the present invention system is switchable between SPECT and PET imaging, the system employs two separate trigger mechanisms for recognizing a valid event and generating a valid event trigger signal. There are at least two differences between these trigger mechanisms for the SPECT and PET imaging systems. Generally, the first difference is that the actual trigger detection circuitry is different for SPECT and PET modes of operation because the count rate is faster for the PET system. The SPECT mode utilizes a leading edge discriminator in its event detection circuitry while the PET mode utilize a constant fraction discriminator in its event detection circuitry because the time between valid events from the two detectors needs to be known with high accuracy. Secondly, the PET mode utilizes a coincidence circuit to determine a valid event from a detected event while the SPECT mode does not. These differences will be explained below.

Figure 2A:
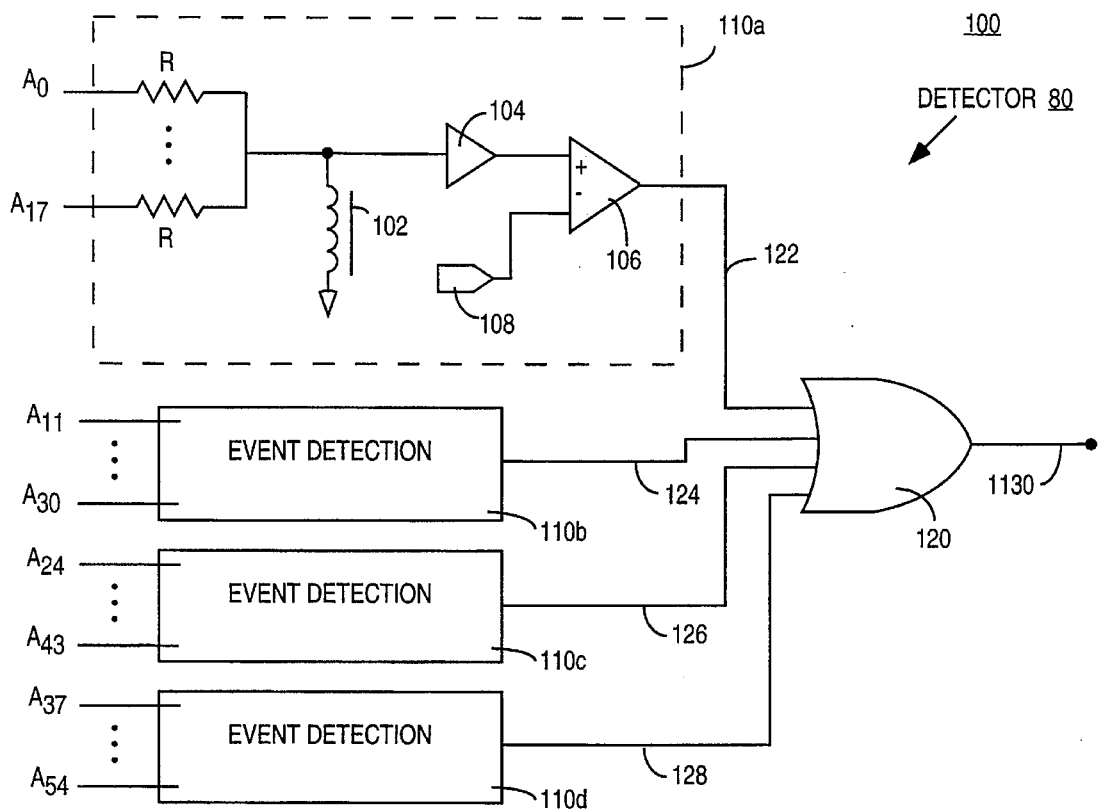
Figure 1:
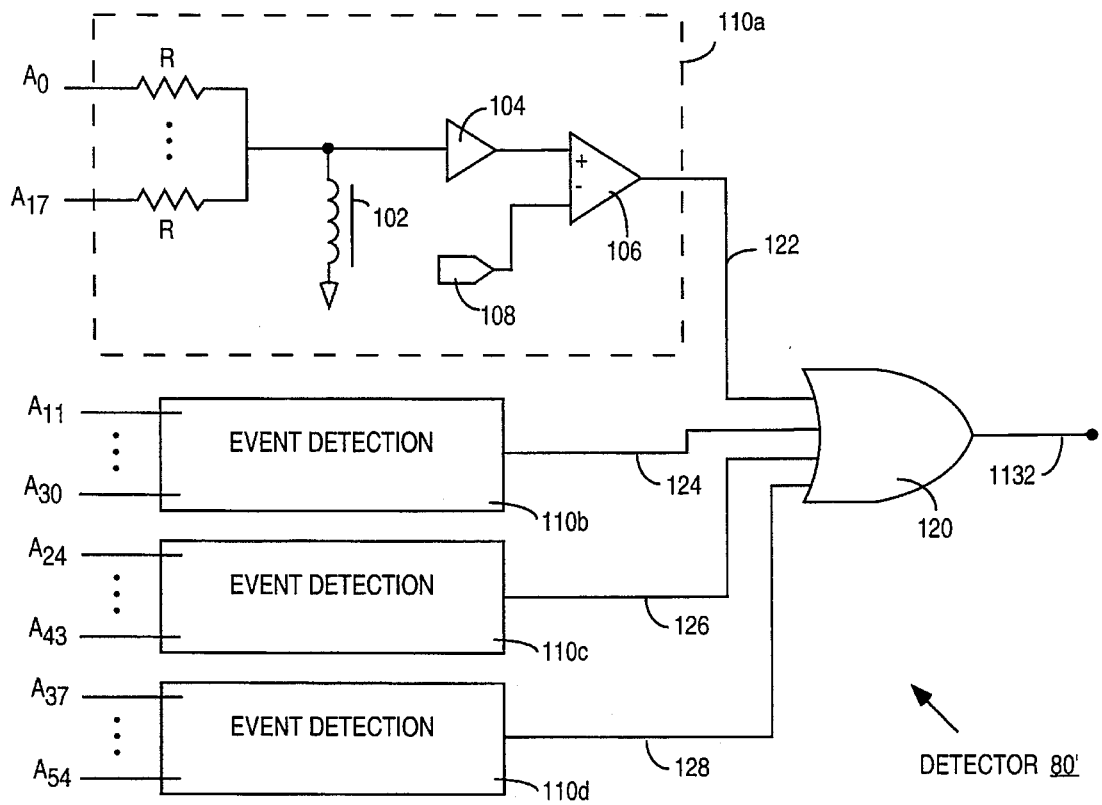
Figure 2A:
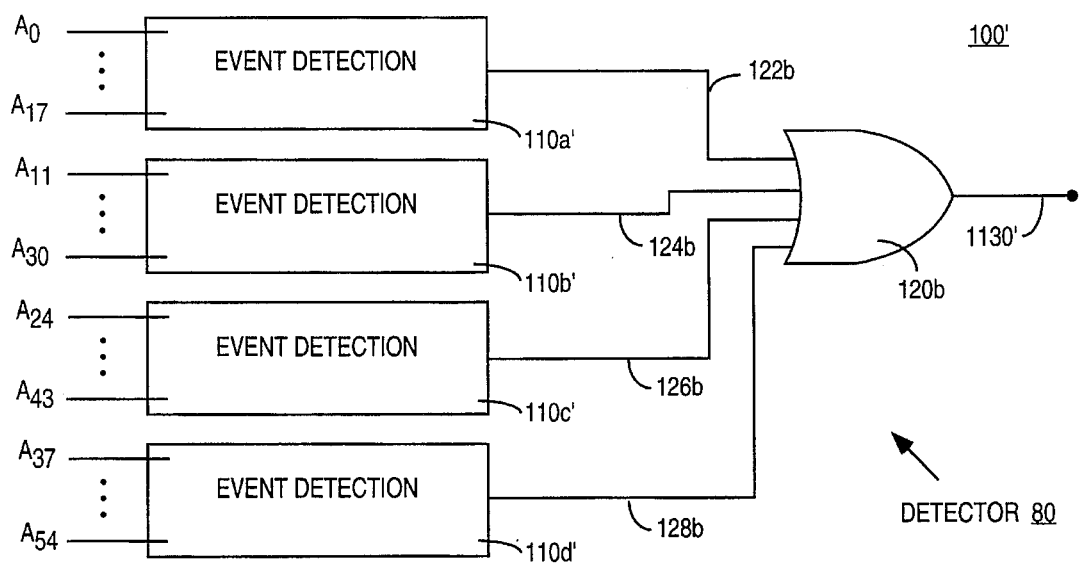

FIG. 2A1 illustrates detection logic 100 for detector 80 utilized in the SPECT mode. A duplicate circuit of 100 (lower) is used for detector 80' for SPECT mode. In a system having more than two detector heads, logic 100 is duplicated for each detector head. The outputs 1130 and 1132 from these two circuits belong to buses 1210 and 1212, respectively, and are forwarded to the CTC unit 1050 (see FIG. 1). Regarding FIG. 2A1, the trigger signal generation circuit 100 is duplicated for each detector as shown. Therefore, discussions regarding the operation of circuit 100 with respect to detector 80 are applicable to the duplicate circuit for detector 80' of the present invention. According to the arrangement of the PMTs in the detector, the output of each PMT associated with a particular spatial quadrant (or "zone") of the detector matrix is sent to one of four trigger detection circuits 110a, 110b, 110c or 110d. Each zone represents a separate spatial portion of the scintillation detector. The zones can be divided horizontally across the imaging surface, vertically, or both. Although the precise alignment of each PMT in each zone is not critical to the present invention, the zones can be overlapping. The PMT signals shown A0–A54 are voltage signals. The signals of the first zone, A0 . . . A17 are sent to trigger circuit ("event detection") 110a where each is coupled to a delay line 102 and an amplifier 104 which together create a 200 ns clip circuit. The trigger pulse received from the PMT circuits is roughly a 200 ns analog pulse. An event occurring within a particular zone will cause an event detection circuit of the corresponding zone to generate an output signal or "event indication." In systems having more than two detectors, the above event detection circuitry is located in each detector.

For the SPECT mode of operation, the clipped signal from circuit 104 is coupled to the positive end of a discriminator circuit 106 and a computer controlled reference input is coupled to a threshold input circuit 108. The reference signal at 108 is coupled to receive the output of a computer controlled DAC (not shown). Therefore, only trigger signals over the threshold voltage are allowed to pass through circuit 106 and they are clipped to 200 ns. The output of the comparator 106 is then coupled to the input of OR gate 120 via line 122. Line 130 will assert a triggering pulse when ever a PMT of the designated zone detects an event. This circuitry is replicated for each of the other four zones of the detector PMT matrix for detector 80 (e.g., signals A11 . . . A30 feed circuit 110b which generates a trigger over line 124, signals A24 . . . A43 feed circuit 110c which generates a trigger over line 126, and signals A37 . . . A54 feed circuit 110d which generates a trigger over 128). The same is true for detector 80'. It is appreciated that additional or fewer event detection circuits (e.g., for more or fewer zones) can be used within the scope of the present invention. Multiple trigger channels (zonal triggering) are used to maintain a high signal to noise ratio in the presence of correlated noise and to maintain low dead time at high count rates. The trigger channels are overlapped, as discussed above, to prevent sensitivity loss at the zone boundaries.

Trigger lines 122, 124, 126, and 128 of FIG. 2A1 are coupled to the input of OR gate 120. Therefore, when an event is detected by the camera detector 80, OR gate 120 of trigger circuit 110 of the present invention will generate a trigger pulse over line 1130. These triggering pulses are used, along with other signals, to generate Start(t0) and Start(t1) and (after going through CTC circuit 1050) are used by the integration circuits 280(0)–280(54) (FIG. 2C) of the present invention to start integration of the PMT signals for the detected gamma event. When an event is detected by the camera detector 80', duplicate OR gate 120 of the duplicate trigger circuit for detector 80' of the present invention will generate a trigger pulse over line 1132. Lines 1132 (for detector 80') and 1130 (for detector 80) are within buses 1212 and 1210, respectively (see FIG. 1).

Figure 2:
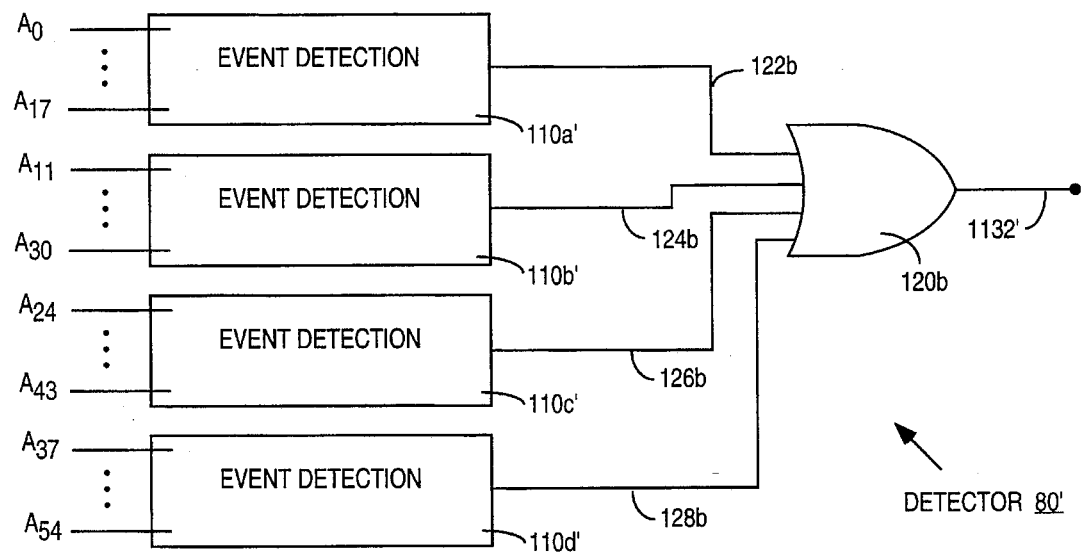

Event detection for the PET imaging mode comprises different electronics which are illustrated in FIG. 2A2. Circuit 100' is associated with detector 80 and a duplicate circuit (lower) is associated with detector 80'. In a system having more than two detector heads, logic 100' is duplicated for each detector head. Unless discussed as different, circuit 100' (used for PET) is analogous to circuit 100 (used for SPECT). The outputs 1130' and 1132' from these PET circuits 100' belong to buses 1210 and 1212, respectively, and are forwarded to the CTC unit 1050 (see FIG. 1). The event detection logic 110a'–100d' for each detector zone utilizes a constant fraction discriminator when in PET mode in lieu of the leading edge discriminator for SPECT imaging used in circuit 100. This is done to maintain timing accuracy when performing PET imaging. An event occurring within a particular zone will cause an event detection circuit (110a'–110d') of the corresponding zone to generate an output signal or "event indication." The output of the event detection circuits 110a–100d' are clipped to one-half the width of the desired coincidence timing window. For each detector, the outputs of the event detection circuitry are forwarded to an OR gates 120b. The outputs 1130' and 1132' of these gates are forwarded over buses 1210 and 1212, respectively. It is appreciated that pipelining of the preamplification/digitizer circuits (as will be discussed below) allows a 240 ns "memory" therefore allowing capture of the entire pulse that generated the detected coincidence pulse in PET imaging mode.

Figures 2, 2A, 3:
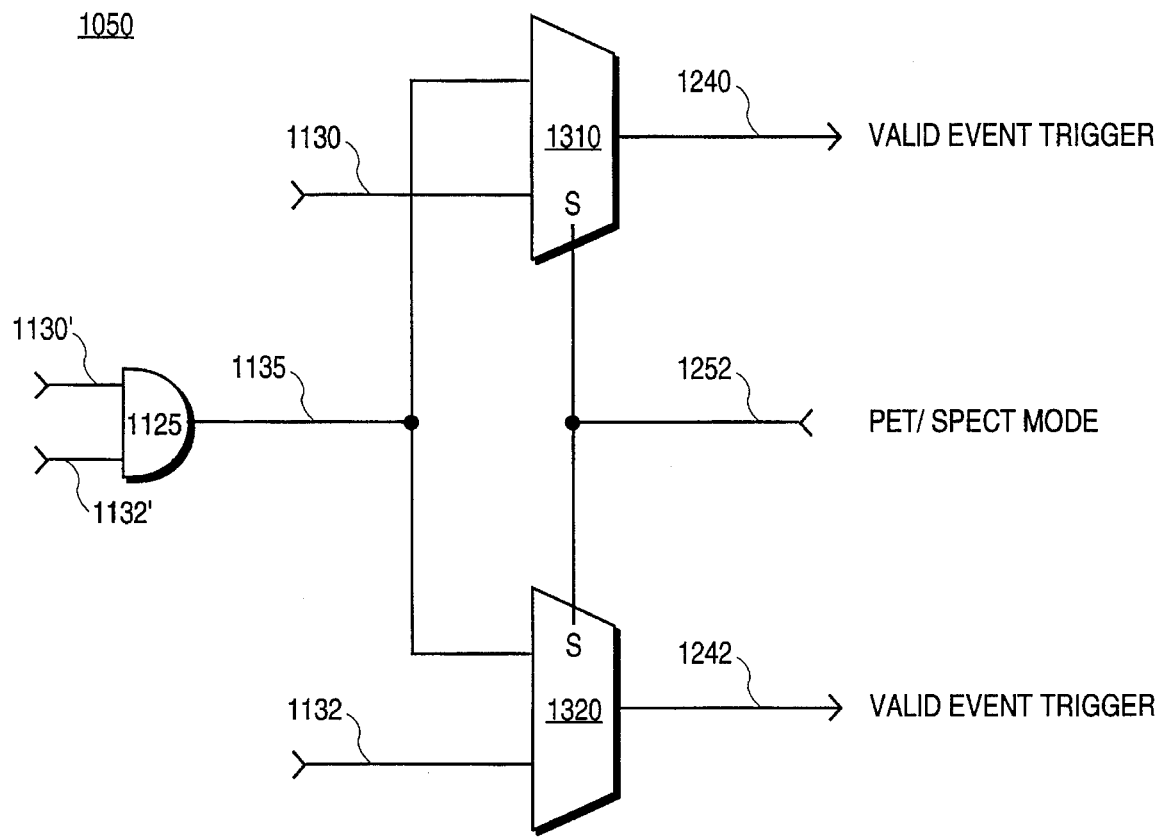

FIG. 2A3 illustrates the logic of the CTC unit 1050 (as shown in FIG. 1). Bus 1210 carries signals 1130 and 1130' while bus 1212 carries signals 1132 and 1132'. Signals 1130' and 1132' are input to AND gate 1125 which generates a signal over line 1135 only if signals 1130' and 1132' are in coincidence (e.g., within a 10–15 ns window). Signal 1135 is coupled to multiplexer 1310 and to multiplexer 1320. Signal line 1130 is coupled to multiplexer 13 10 while signal 1132 is coupled to multiplexer 1320. A control (or select) signal 1252 is coupled to the select inputs of multiplexers 1310 and 1320. When the control signal 1252 selects PET imaging operation mode, then the signal over line 1135 passes over both line 1240 to detector 80 and to line 1242 to detector 80'. These are the valid event trigger signals. When the control signal 1252 selects SPECT mode, then the signal over line 1130 is carried over line 1240 to detector 80 and the signal over line 1132 is carried over line 1242 to detector 80'. These are the valid event trigger signals. It is appreciated that the signals over line 1240 are used to trigger the integrators associated with the preamplification and digitization circuitry for detector 80 while the signals over line 1242 are used to trigger the integrators associated with the preamplification and digitization circuitry for detector 80'. The signals carried over line 1240 and 1242 represent "valid" event detection. The multiplexers 1310 and 1320 allow a switchable mode of operation between event detection for SPECT and PET imaging modes under the present invention including a coincidence detection mode (line 1135) and a non-coincidence detection mode (lines 1130 and 1132).

For detector 80, the valid event trigger signal 1240 is used as trigger signal 130 to convey start (t0) and start (t1) while for detector 80' the valid event trigger signal 1242 is used as trigger signal 130.

In a system having more than two detector heads, in SPECT mode, the event indication signals from each detector are routed back to their associated detector as the valid event trigger. In PET mode, a series of AND gates are coupled so that each possible combination of two detector is represented by an AND gate and, in such way, a coincidence between any two detectors of the system can be determined. Once a coincidence is detected, a valid event trigger is forwarded back to the two detectors in coincidence.

ANALOG SUM OF GLOBAL ENERGY

Figure 2B:
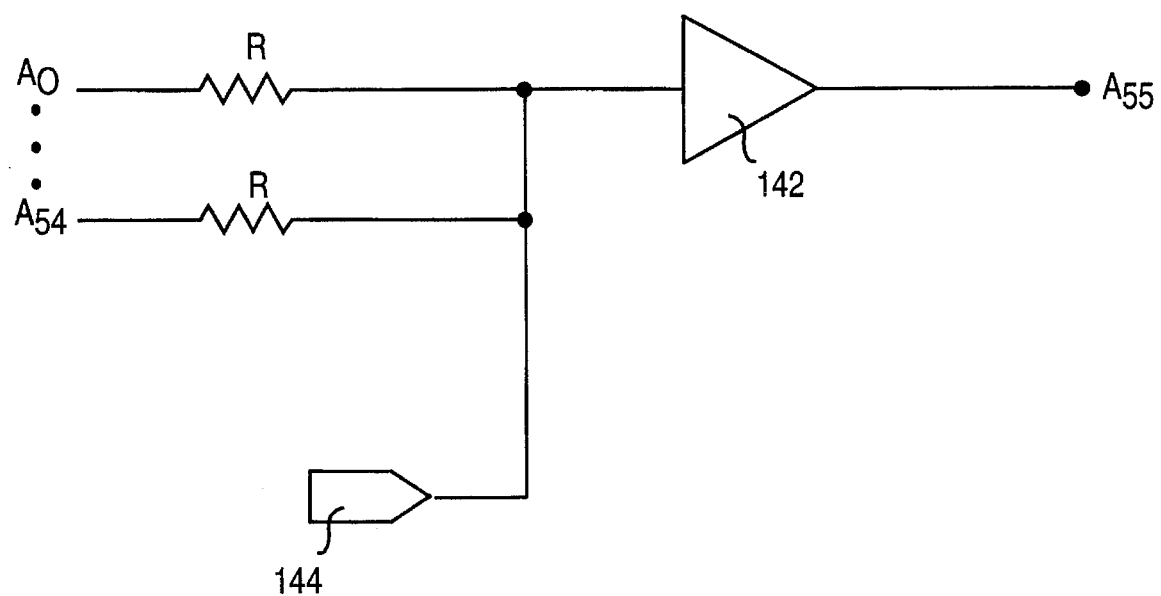
FIG. 2B is a circuit diagram of the circuitry utilized by the present invention for generating an analog total ("global") energy signal.
Figure 2C:
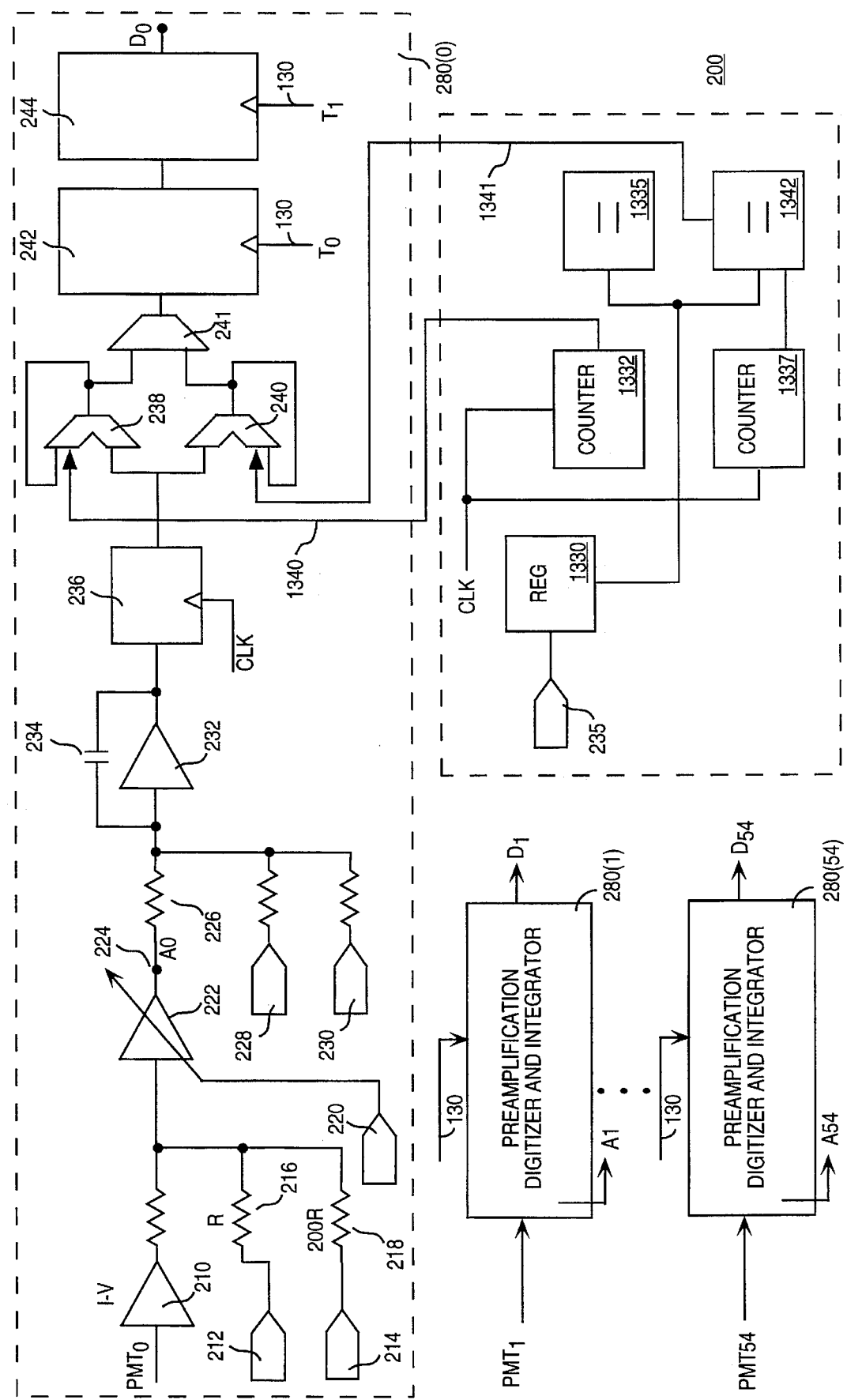
FIG. 2C illustrates the preamplification/digitizer circuitry of the present invention (utilizing dual integrators per channel) for providing a compensated digital response signal that is digitally integrated for each PMT of the gamma detector and allowing programmable integration intervals for PET/SPECT imaging modes of operation.

FIG. 2B illustrates an analog summing circuit utilized by one embodiment of the present invention. This circuit is included in detector 80 and a separate circuit in detector 80'. The voltage signals A0 . . . A54 from each PMT channel (e.g., signal from each PMT) are summed together and output by amplifier 142. An offset voltage is fed into the summing circuit via input 144. The offset voltage is controlled by a computer controlled DAC. The output, or total energy of the gamma event, is generated over line A55. This output represents the analog sum of all of the voltage signals from each PMT channel plus an adjustable offset from circuit 144. The analog signal over A55 is called the analog global energy signal. This global energy signal may be supplied to an available channel (e.g., channel 55) for preamplification, digitization and integration by circuit 200 (FIG. 2C). The Digital Event Processor of each detector the present invention receives signal A55 of its corresponding detector. As will be discussed to follow, the global energy value is also computed digitally by summing the digitized integrated channel signals of the PMTs. Either of these methods can be utilized within the scope of the present invention.

PREAMPLIFICATION DIGITIZER

Refer to FIG. 2C which illustrates the preamplification digitizer circuits 200 of the present invention for each of the 55 channels (plus one for A55) for detector 80. A duplicate of this circuit is used with the channels of detector 80'. In a system having more than two detectors, circuit 200 is duplicated for each detector. Circuit 200 is used for both SPECT and PET imaging mode and utilizes switchable circuitry to optimize between modes. These circuits perform the preamplification, digitization, and integration for each analog voltage signal for a PMT channel. The output of circuit 200 is fed to a Digital Event Processor for detector 80. A duplicate preamplification digitizer circuit 200 is used for detector 80' and outputs to a duplicate Digital Event Processor of detector 80'. As will be discussed, each preamplification digitizer circuit for each channel contains two separate integrator circuits. Unless discussed otherwise, circuit 200 for detector 80 is analogous in operation and structure to its duplicate circuit of detector 80'. Circuit 280(0) corresponds to the current (amps) output signal received directly from PMT #0 (e.g., channel 0) and this circuit 280(0) is separately replicated for each of the 55 PMT channels of the present invention and, as shown, circuits 280(0) to 280(54) operate to simultaneously process the current output signals for PMT0 to PMT54. Regarding circuit 280(0), the current signal output of PMT0 is fed into a current to voltage converter 210 and the output of this signal is fed through a resistor to a voltage gain amplifier 222.

A computer controlled digital to analog converter (DAC) outputs two adjustment signals over line 212 and 214 for baseline voltage correction. The signal over line 212 is fed through a resistor 216 for coarse adjustment and line 214 is fed through resistor 218, which has much larger resistance (e.g., on the order of 200X) than resistor 216, for fine adjustment. The signals received via lines 212 and 214 provide a baseline offset voltage adjustment to the output signal received from the PMT0. A computer controlled digital to analog converter (DAC) outputs a voltage adjustment signal to circuit 220 to control the gain of amplifier 222 having an exemplary gain adjustment of 10:1. The analog gain adjustments are coarse adjustment with fine gain adjustments performed by the calibration table, see FIG. 2D as discussed to follow. The baseline offset adjusted signal and the gain adjusted signal is then output at point 224 as signal A0 for each channel. Similarly, for each PMT channel, the above circuitry is replicated for generating signals A1 to A54. The trigger signal 130 is uniformly supplied to each of the circuits 280(0) to 280(54) so that each channel is triggered coincidentally.

The output of gain amplifier 222 is then fed into resistor 226. The voltage input 228 and voltage input 230 are coupled through respective resistors to the output of resistor 226. The output of resistor 226 is then fed into amplifier 232 and capacitor 234 in series. The outputs of the amplifier 232 and capacitor 234 are then coupled to the input of the analog to digital converter (ADC) 236. The above circuit (e.g., from point 224 to the input of ADC 236) is utilized for pulse insertion used for diagnostic purposes that are not particularly pertinent to the present invention. Pulses may be artificially inserted via inputs 228 and 230.

Referring to FIG. 2C, the ADC 236 converts the analog signal A0 to digital samples based on the frequency of clock input as shown. One embodiment of the present invention utilizes a sample frequency of 20 to 25 MHz as a sample clock. The output of ADC 236 is then fed to the input of two adders ("integrators" or "accumulators") 238 and 240 coupled in an integration configuration. The present invention utilizes dual digital integrators for each PMT channel in order to more effectively process conditions wherein two gamma events are detected in close temporal proximity. Each integrator 238 and 240 (of each channel 0–54) contains a separate register (accumulator) for containing the current sum value and performs piecewise linear integration with a clip binary value at 1023 (e.g., no rollover is allowed). The outputs of both integrators are coupled to multiplexer 241. The multiplexer 241 selects between one of the two integrator registers (accumulators) for output to the latch circuits 242 and 244. Latch circuits 242 and 244 comprise a two stage FIFO arrangement. The trigger pulses Start(t0) and Start(t1) received over 130 are used to reset the integrators. These trigger pulses arrive over line 1240 for detector 80 and over line 1242 for detector 80'. At the end of a programmable integration (accumulation) period, the value of the integration process for either integrator is then stored within a two stage latch circuit of 242 or 244. The output of the latch circuit 242 or 244 is the digitized value of the signal generated by PMT0 for a given event and this value is designated as D0. The digitized signal D0 is supplied to the Digital Event Processor 300. The above is explained in more detail with reference to FIG. 6B.

Under computer control, the duration of the integration period for all integrators is programmable over line 235 which is coupled to a computer processor. The programmed period (having a resolution of the sampling clock frequency of 20–25 MHz) is loaded into register 1330 over line 235. Upon a valid event detection signal (over line 1240) that resets integrator 238, a corresponding counter 1332 is also reset. Counter 1332 is coupled to the sampling rate clock. The output of the counter 1332 is coupled to a comparator 1335 which also receives an output from register 1330 which contains the programmable integration (accumulation) period. Upon a coincidence, an output signal is carried over line 1340 which signals the completion of the integration period for integrator 238. Upon a valid event detection signal (over line 1240) that resets integrator 240, a corresponding counter 1337 is also reset. Counter 1337 is coupled to the sampling rate clock. The output of the counter 1337 is coupled to a comparator 1342 which also receives an output from register 1330 which contains the programmable integration (accumulation) period. Upon a coincidence, an output signal is carried over line 1341 which signals the completion of the integration period for integrator 240. It is appreciated that like the integrator circuits 238 and 240, the counters 1332 and 1337 are not effected by the trigger pulse unless they are idle at the time the valid event trigger pulse is received.

It is appreciated that register 1330, counters 1332 and 1337, and comparators 1335 and 1342 are coupled to each channel circuitry 280(0)–280(54) and the connections shown with respect to channel circuitry 280(0) are exemplary of the connections made for each other channel. In other words, only one register 1330 is utilized to contain the integration interval associated with all channel integrators for a given detector. Specifically, the output of comparators 1335 and 1342 are coupled to the accumulators 238 and 340 of all channel circuitry 280(0)–280(54) in the fashion shown in FIG. 2C with respect to channel circuit 280(0).

The integration (accumulation) period programmed into register 1330 is programmable with a resolution of 20–25 MHz in one embodiment of the present invention. During PET imaging, the accumulation period is set to approximately 320 ns per event due to the high count rate received during PET imaging and the high energy distribution of gamma events that are detected (511K electron-volts) in PET imaging. During SPECT operational modes, the accumulation period is set to approximately 840 ns as a result of the lower count rate detected and the lower energy distribution of gamma events detected. Therefore, using the above circuitry, the present invention provides a programmable mechanism for optimizing the preamplification/digitizer circuits for either PET or SPECT modes and this mechanism is switchable. It is appreciated that a duplicate circuit 200 is included for detector 80' but its valid event trigger signals (e.g., 130) arrive over line 1242 instead of line 1240. The program signal 235 is coupled to both circuits 200 such that both detectors 80 and 80' are simultaneously configured for PET or SPECT mode of operation.

Using the dual integrators of FIG. 2C of the present invention, either one or both of the accumulators of 238 or 240 can be enabled to integrate an incoming signal from the output of ADC 236. The two integration results are multiplexed onto a common data path and either result can be selected and stored in the two stage latch circuit. Each integrator can be separately triggered by valid event trigger start(t0) and start(t1). In operation, when a trigger signal occurs, if either integrator is available (e.g., not integrating and not holding an integrated result) then that accumulator is reset and enabled to begin integrating the event. When either of the accumulators completes, the integrated value is transferred to the first FIFO stage (e.g., latch 242) assuming this stage is available. If it is not available, the accumulator holds the value. Integration continues for a predetermined period of time after the trigger signal until a sufficient amount of the gamma event's energy is integrated. Values are transferred from FIFO stage 1 (latch 242) to FIFO stage 2 (e.g., latch 244) as FIFO stage 2 becomes available (e.g., transfer its value). When data is written to FIFO stage 2, the present invention signals that data is ready to be transferred to an associated Digital Event Processor (DEP) 300, see FIG. 2D. Each detector 80 and 80' contains its own DEP circuit 300.

Referring to FIG. 2C, the dual accumulator design of the present invention provides an implicit mechanism for handling event pile-up where two events interact during the same time period. Since the present invention computes positions based on local PMT clusters, pile-up events which occur in different regions of the detector can be properly positioned and such are called temporal pile-ups. If the two events that are involved in a temporal pile-up happen to be separated by more than the trigger channel deadtime, then both accumulators will be enabled and both events will be fully integrated. Accuracy of positions will be impacted by the spatial distance separating the temporal events. The greater the separation, the lower the impact. This is discussed in more depth below.

Within circuit 200, the circuit 280(0) is replicated for each channel as shown in FIG. 2C. The output current signals from PMT#1 through PMT#54 are fed into circuits 280(1) through 280(54). The digital data signals D0 to D54 are output from circuits 280(0) through 280(54), respectively. Each of the 55 preamplification digitizer circuits 280(0)–280(54) are coupled to receive valid event trigger signals start(t0) and start(t1) from line 130. It is appreciated that an extra channel (e.g., a preamplification digitizer circuit 280(55)) can be added in order to process the analog global energy signal from A55 (see FIG. 2B). In this embodiment, the output D55 would correspond to the amplified, digitized and integrated value for all channels (e.g., the digitized value of the analog global energy of the event). In such an embodiment, the value D55 would be output to the DEP 300 (as will be discussed to follow) with an appropriate PMT address value indicating the data as analog global energy data.

The preamplification circuits of FIG. 2C can be directly adjusted using gain (e.g., line 220) and baseline offset (e.g., lines 212 and 214) adjustments. The above adjustment lines are referred to as control link signals which are coupled to computer controlled addressable DACs. The amount of nominal baseline and the amount of variation associated with levels of adjustment can be used to determine the accuracy of a given channel.

At the completion of the programmed integration period, when latch 244 data is present, then all of the digital data stored in each second stage latch for each channel is transferred to the appropriate DEP 300 (FIG. 2D) over bus 307. This is called a data "transfer" to the DEP 300 and occurs for both detectors 80 and 80'.

DIGITAL EVENT PROCESSOR

Figure 2D:
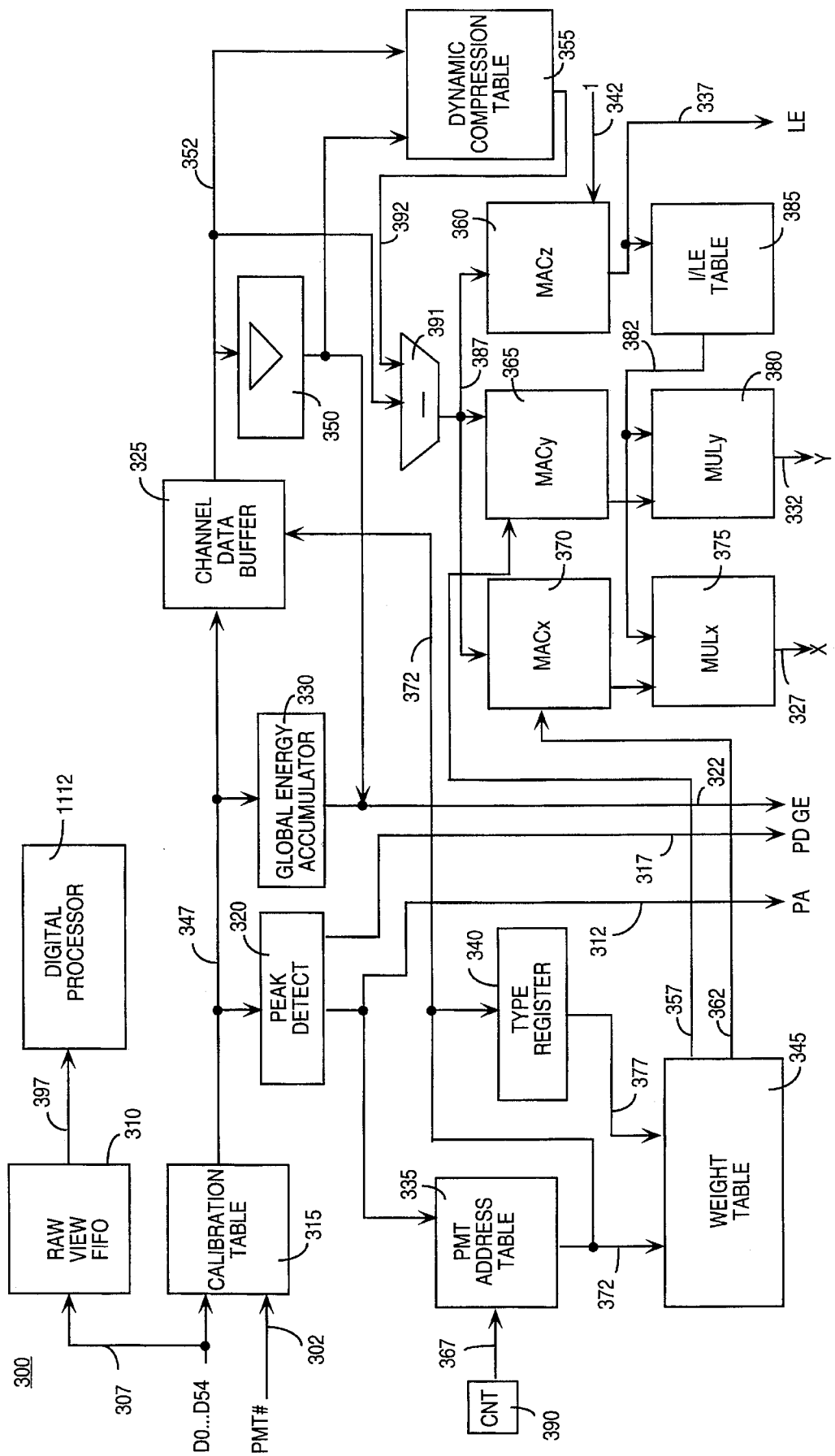
FIG. 2D illustrates the processing blocks of the present invention Digital Event Processor of each detector for generation of the spatial coordinates of an event, local and global energy, peak PMT address and the associated signal output.
Figure 3:
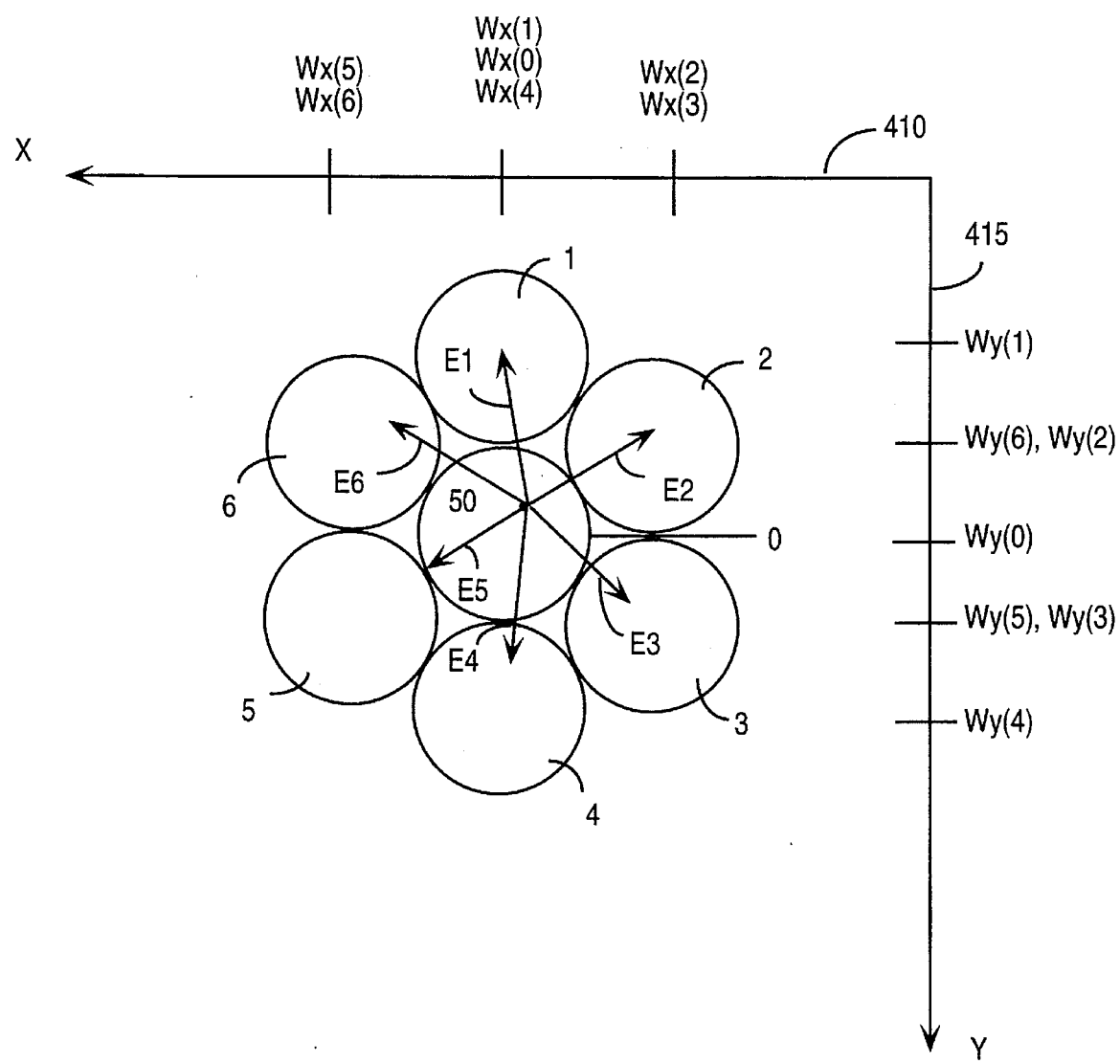

Refer to FIG. 2D which illustrates circuitry 300 of the Digital Event Processor (DEP) of the present invention. It is appreciated that the digital processor 1112 is not part of the DEP 300 circuit but is rather located within the acquisition computer system 1055. Discussions herein describe the DEP 300 associated with detector 80. A duplicate DEP circuit 300 associated with detector 80' operates in an analogous fashion with respect to output it receives from the preamplification/digitizer circuits associated with detector 80'. The duplicate DEP 300 associated with detector 80' is also similarly coupled to the digital processor 1112. The output of DEP 300 for detector 80 is carried over bus 1220 to the acquisition computer 1055. The output of duplicate DEP 300 for detector 80' is carried over bus 1222 to the acquisition computer 1055. Each DEP 300 of the detector pair 80 and 80' operates independently of the other to generate the X, Y, and Z outputs to the acquisition computer system 1055.

The following discussion describes the DEP 300 associated with detector 80, however, it is applicable to the duplicate DEP within detector 80'. The digitized and integrated signal values for the PMT channels over lines D0 through D54 are fed over bus 307 to FIFO 310 and to calibration table 315 shown in FIG. 2D. The data over bus 307 represents the digitized integrated signals supplied from each PMT channel circuit, 280(i), in response to a triggering event such as a scintillation event. The digitized data over bus 307 is stored into a raw view FIFO 310 that can be accessed over bus 397 by the digital processor computer 1112. The raw view FIFO allows data to be pulled from the input data stream without interrupting the normal data flow from the PMTs. This is utilized for on-the-fly baseline adjustment. A calibration table 315 receives as inputs (1) the digitized integrated channel data from bus 307 and also receives (2) PMT address (e.g., indicator) number over bus 302 of the reporting PMTs in order to correlate the digital data over bus 307 with the proper PMT channel output from circuits 280(i).

The calibration table 315 contains a lookup table (LUT) for providing a gain output which can vary with the PMT number input (represented in one embodiment as an address); this spatially variant gain is applied to the integrated signal value received over bus 307 and the result is output over bus 347 which is a corrected or finely compensated integrated signal value for each PMT channel. The gain value stored in the calibration table 315 is a fine gain adjustment dependent on the PMT number whereas the gain amplifier 222 is a coarse gain adjustment. The calibration table 315 also provides a baseline adjustment computation by digitally subtracting the reference voltage inserted by the baseline offset circuitry (e.g., inputs 212 and 214) of the preamplification circuits for each PMT channel independently. The output over bus 347 is the digitized values supplied from 307 with this baseline adjustment.

The output of the calibration table 315 is transferred over bus 347 to a peak detect circuit 320 which analyzes all the calibrated results of all 55 channels (for a given data transfer) and selects the PMT number having the largest integrated channel signal (e.g., "energy") output for a given measured event; this is the "peak PMT." The maximum integrated signal value and the associated channel address are retained for later use in the DEP process of the present invention. The integrated signal associated with the peak PMT is output from peak detect circuit 320 over bus 317 as value PD. The PMT address number associated with the peak PMT is output by circuit 320 over bus 312 as value PA. To support analog global energy data being transferred over a digitizer channel of 280(i), the peak detect 320 can be disabled for a given PMT address. Bus 347 is also coupled to a global energy accumulation (GE accumulation) circuit 330. Circuit 330 sums the corrected integrated channel signals output over bus 347 for each of the PMT channels for a given event. The output of circuit 330 is the digitized global energy GE (which is a digital sum of all of the PMT's digital integrated signals) and is transferred over bus 322 which forms output GE and also is coupled to the dynamic compression table 355.

Buffer 325 of FIG. 2D stores the digital integrated signal value of each PMT channel correlated with the appropriate PMT address received over bus 347. Buffer 325 can be implemented in RAM or other memory storage device. The PMT integrated signal values for all channels are stored in buffer circuit 325. The address of the peak PMT is output over bus 312 to circuit 335 which is the PMT address table. Circuit 335 contains a lookup table that outputs a PMT cluster based on a peak PMT address input from bus 312. The PMT cluster is a collection of PMTs whose integrated channel responses (as well as a total energy for the event) are used to perform the DEP computation to determine the spatial location of the event (e.g., the centroid of the cluster). By using a lookup table at circuit 335, the present invention is able to provide spatially variant cluster shape and to vary spatially the number of PMTs that form a given PMT cluster. When operating in PET imaging mode, circuit 335 is programmed to output relatively smaller (e.g. 7 PMTs) cluster sizes while operating in SPECT imaging mode, circuit 335 is programmed to output relatively larger (e.g. 17–19) sized clusters.

Within the scope of the present invention, for an input peak PMT address, the shape of the resultant PMT cluster and the number of PMTs that make up the selected PMT cluster vary based on the spatial location of the peak PMT address within the overall PMT matrix. It is appreciated that in SPECT imaging mode the PMT address table 335 can vary the PMT cluster associated with the peak PMT address based on a selection for high or low resolution wherein a low resolution mode may require 7 PMTs per PMT cluster where a higher resolution mode may require 9 to 19 PMTs per PMT cluster. Therefore, a resolution indication signal (not shown) is also input to the table 335. It is appreciated that in lieu of a resolution indicator signal, the entire table 335 can be reloaded with data for different desired resolutions. In such case the resolution signal is not used as an addressing signal but only initiates the downloading of the new information.

A sequence counter 390 is coupled to the PMT address table 335 via bus 367. The PMT address table 335 controls (1) the number of PMTs in the selected PMT cluster for the given event and (2) the type value of the PMT cluster (which is then stored in circuit 340 and held throughout the spatial computation for a given event). The PMT address table 335 also contains the address of the analog global energy channel. The sequence counter 390 then counts, sequentially, from one to the number of PMTs that are associated with the selected PMT cluster and sequentially presents each count value over bus 367. In one embodiment, the PMT address table 335 is itself addressed by two values, (1) the MSB of the address that originates from the peak PMT address value over bus 312 and (2) the LSB of the address value that originates from the count value of the sequence counter 390 over bus 367. The last entry within the PMT address table for a given peak PMT includes a stop code that indicates the end of the PMT cluster constitution for that peak PMT address. The centroid computation circuitry therefore stops (e.g., is terminated) when the stop code is reached (or equivalently when the maximum count value is reached as reported by the table 335).

The PMT address table 335 outputs over bus 372, in sequence based on the sequence counter 390, the PMT addresses of each PMT of the PMT cluster used in the spatial computation for a given event. The order in which these PMTs are presented over bus 372 is governed by the lookup table stored in the PMT address table 335 based on the peak PMT address value from bus 312 and the count value over bus 367. The PMT address values output from circuit 335 are also coupled to data buffer 325 to address this memory circuit which will output the appropriate integrated channel signal value over bus 352 for that PMT. This output is used in the DEP's spatial computation.

Referring still to FIG. 2D, the PMT cluster type value is output from the PMT address table 335 to the memory circuit 340 which holds the PMT cluster type value throughout a centroid (e.g., coordinate) computation. The PMT address values over bus 372 are also fed to a weight table circuit 345 that contains a lookup table correlating PMT address value with a given x and y weight value used for the spatial computation circuitry of the present invention. By providing the lookup table within circuit 345, the weight associated with a given PMT depends on its address value and is correlated with the spatial location of the PMT and it is also dependent on the PMT cluster type value from bus 377.

The weight value associated with a given PMT address can also vary based on the type value stored in 340 which is based on the peak PMT for the PMT cluster of the given event; this is accomplished by the type registration circuit 340 of the present invention. Therefore, if the peak PMT address corresponds to be an edge or corner PMT, then the PMT cluster will be of a special type and the weights associated with the PMT addresses of the resultant PMT cluster can be adjusted to account for the missing PMTs of the centroid computation (e.g., the PMTs that are not available due to the edge or corner location of the peak PMT). Therefore, the PMT weight value output from circuit 345 depends on (1) the PMT address value and (2) the type value from circuit 340 that is based on the address value of the peak PMT for the PMT cluster. The PMT address table 335 defines the PMT addresses that constitute the selected PMT cluster.

In one embodiment, the type registration circuit 340 may contain a lookup table based on the peak PMT address value output from circuit 335. As discussed, the PMT cluster type value is an offset into the weight table 345 for a given PMT cluster and is used to provide variations in the weights output of the weight table 345 for a given PMT address value of a given PMT cluster. Circuit 340 is coupled to supply the offset value to circuit 345 via bus 377. According to the operation of the present invention, for a given PMT cluster, the PMT addresses that make up the PMT cluster are sequentially output over bus 372 to the weight table and a constant type value is generated and output over bus 377 (based on the address of the peak PMT). The weight table 345 then outputs an x weight over bus 362 and a y weight over bus 357, for each PMT of the given PMT cluster.

The x weight value over bus 362 of FIG. 2D supplies a multiplier accumulator circuit (MACx) 370 for the x coordinate computation and the y weight value over bus 357 supplies a multiplier accumulator circuit (MACy) 365. These circuits 370 and 365 are reset and initialized at the start of the spatial computation for each gamma event. The x and y weight values are utilized in the spatial computations for a given event (e.g., gamma interaction) and specify the amount of contribution a given PMT's integrated channel signal value should carry (for a given PMT of the PMT cluster) in the coordinate computation process.

As discussed above, the PMT addresses of the PMTs of a given PMT cluster are placed over bus 372 in sequence. Bus 372 of FIG. 2D is coupled to address the buffer 325 with the PMT address value for each PMT involved in the PMT cluster. In response to the address value of a given PMT of the PMT cluster, buffer 325 outputs the stored and corrected digital signal value associated with the PMT (for a given event) as received over bus 347. This corrected signal value is transferred over bus 352 to block 350, to block 355 and to subtractor 391. A circuit 360 is coupled to receive the digital signal values of the PMT's involved in the given PMT cluster and accumulates these values to provide a local energy (LE) value which is generated over bus 337.

Block 350 is a buffer for containing either a digital or analog global energy value when operating in a mode wherein the global energy data is transferred over a digitizer channel and stored in the storage buffer 325. In this mode the global energy stored in block 350 is a digitized version of the analog global energy signal. Output from the analog signal A55 (of FIG. 2B) is fed to a preamplification digitizer channel of 280(*i*) and then over bus 307 to the calibration table 315 and stored in buffer 325. The global energy may also be computed by accumulator 330 by adding the values of the integrated signals from each PMT channel. The global energy value is then stored in buffer 350. Therefore, the global energy value GE over line 322 can be (1) a digitized value of the analog global energy value or (2) a digital summed value of the digital signals of each PMT channel.

The dynamic compression table 355 of FIG. 2D receives the global energy value of the detected gamma event over bus 322 and also receives the digitized integrated channel signal value for a given PMT of the PMT cluster over bus 352. The dynamic compression table 355 contains a lookup table of compensation values for the digitized integrated channel signals. The output of the lookup table is driven on bus 392 to a subtractor 391 which also receives the signal value over bus 352. The table 355 receives as an address the MSBs of the global energy (from bus 322) and predetermined bits of the signal value for each PMT over bus 352. Via the connection with the subtractor 391, the signal data over line 352 is shifted left by four bits (e.g., multiplied by 16). The output from table 355, in one embodiment, is subtracted from this left shifted signal value. The output of the subtractor circuit 391 is the dynamic compressed integrated signal value for a given PMT channel and is then fed to the MACx 370 circuit, the MACy circuit 365 and also to an energy multiplier accumulator (MACz) circuit 360.

The dynamic compression table 355 of FIG. 2D is utilized by the present invention to alter the integrated channel signal output from a PMT channel so that when summed with altered signals from other channels, the summation signal will be more linear in nature. The information stored in the dynamic compression table 355 that is used to perform the signal conversion is readily programmable within the present invention and different conversion data sets may be stored (down loaded) in the table 355 at one time. Since the conversion data may be altered readily (e.g., a new set can readily be downloaded, if needed) the dynamic compression table 355 of the present invention is modifiable. The subtraction logic 391 is a part of the compression procedure used by the present invention and is used in order to reduce the memory size requirement of the compression table 355. Therefore, it is appreciated that, given a larger memory size, the subtractor 391 may be eliminated from the present invention and integrated into the memory 355 by altering the data stored therein. The output of the dynamic compression table 355 is called the "dynamic compressed" or "compressed" integrated signal data for a particular channel and is supplied to the centroid computation logic via bus 387.

Therefore, as the sequence counter 390 counts through the PMTs of the PMT cluster, the buffer 325 supplies the integrated signal associated with each PMT. Also, the weight table 345 supplies the x and y weight values associated with each sequenced PMT. The MACx circuit 370 multiplies the x weight value and the dynamic compressed signal for each PMT and accumulates these values for each PMT of the PMT cluster as the sequencer counts. The MACy circuit 365 multiplies the y weight value and the dynamic compressed signal for each PMT and accumulates these values for each PMT of the PMT cluster as the sequencer counts. The MACz circuit has two inputs, one is coupled to bus 342 which is programmed to a value of "1," and the other input is coupled to bus 387 and therefore will accumulate the integrated signal of each of the PMTs of the PMT cluster to generate a value of the local energy (LE) over bus 337.

After the sequencer 390 of FIG. 2D reaches the last PMT of the PMT cluster, the MACz circuit will output the complete LE value over bus 337 which is coupled to a 1/LE circuit 385. This is a lookup table that provides the inverse (e.g., $(LE)^{-1}$) of the LE value. Circuit 385 can also be realized using a divider circuit. The value of (1/LE) is then output over bus 382 to x multiplier circuit (MULx) 375 and also y multiplier circuit (MULy) 380. Circuit 375 multiplies the accumulated result of the MACx circuit 370 with the (1/LE) value to generate the normalized x coordinate of the gamma event over bus 327. Circuit 380 multiplies the accumulated result of the MACy circuit 365 with the (1/LE) value to generate the normalized y coordinate of the gamma event over bus 332. Therefore, the DEP 300 of the present invention computes the spatial coordinates (x, y) and the total energy (GE) of each gamma event. Also produced for each event is the peak PMT energy (PD) which is the peak signal of the integrated channel signals received by the DEP, peak PMT address (PA) and the local energy (LE).

The X, Y, GE and LE values associated with the DEP circuit 300 of detector 80 are supplied over bus 1220 (see FIG. 1) to the acquisition computer 1055, while X, Y, GE and LE values associated with the DEP circuit 300 of detector 80' are supplied over bus 1222 to the acquisition computer 1055. In SPECT mode, the detector pair 80 and 80' perform event detection and localization relatively independently because their valid event triggering signals (1240 and 1242) do not need to be in coincidence. In PET mode, since the event detection needs to be in coincidence, the DEP circuits of both detectors 80 and 80' operate in a form of synchronization based on the coincidence of the valid event trigger signals.

The spatial coordinates (x, y) of a gamma event (interaction) are computed by the DEP 300 circuit using the below centroid computation:

$$x = \frac{Wx_1*E_1 + Wx_2*E_2 + Wx_3*E_3 + \ldots + Wx_n*E_n}{E_1 + E_2 + E_3 + \ldots + E_n}$$

$$y = \frac{Wy_1*E_1 + Wy_2*E_2 + Wy_3*E_3 + \ldots + Wy_n*E_n}{E_1 + E_2 + E_3 + \ldots + E_n}$$

Where:

$Wx_i$=the x weight from circuit 345 for the $i^{th}$ PMT of the Cluster $Wy_i$=the y weight from circuit 345 for the $i^{th}$ PMT of the Cluster $Wx_n$=the x weight from circuit 345 for the last PMT of the Cluster $Wy_n$=the y weight from circuit 345 for the last PMT of the Cluster $E_i$=the integrated signal for the $i^{th}$ PMT of the PMT Cluster $E_n$=the integrated signal for the last PMT of the PMT Cluster The DEP 300 operates as discussed above for each detected gamma event of an imaging session and stores the above information to a computer memory storage unit. This information is then transferred to correction electronics (or CPU system) where the data is corrected for energy, linearity, and uniformity. This can be done in either the acquisition computer 1055 or the image processor 1060. It is appreciated that a number of well known methods and circuitry components may be used for collecting the count data output from the DEP 300 circuits and for forming an image based thereon by correcting the data supplied from the DEP 300 circuits (e.g., for nonuniformities, etc.) and spatially recording the counts. Any of these well known methods may be used in conjunction within the present invention.

FIG. 3 illustrates the applicability of the above spatial computations and gives an exemplary situation. FIG. 3 illustrates a selected PMT cluster configuration as is generated based on the peak PMT address (here it is PMT0) and based on the PMT address table circuit 335. The PET imaging mode is selected in this example so the PMT cluster is composed of seven PMTs (six surrounding and one center PMT). The address table circuit 335 would also output a type registration to circuit 340 to indicate that the PMT cluster is of a symmetrical or normal type because the peak PMT is not located on the edge nor in a corner of the PMT array of the detector head 80. An exemplary x axis 410 and y axis 415 are shown and the weight values for each of the PMTs for the x and y axis are plotted along the axis for each PMT.

The exemplary event occurs at point 50 within FIG. 3 and the arrows extending outward represent the amount of light received by each PMT toward which the associated arrow points. The weight values for each of the PMTs in the x and y directions are also dependent on the spatial location of the peak PMT because the location of the peak PMT will alter the PMT type value which is used (in conjunction with the PMT address) to address the weight table circuit 345.

Figure 4A:
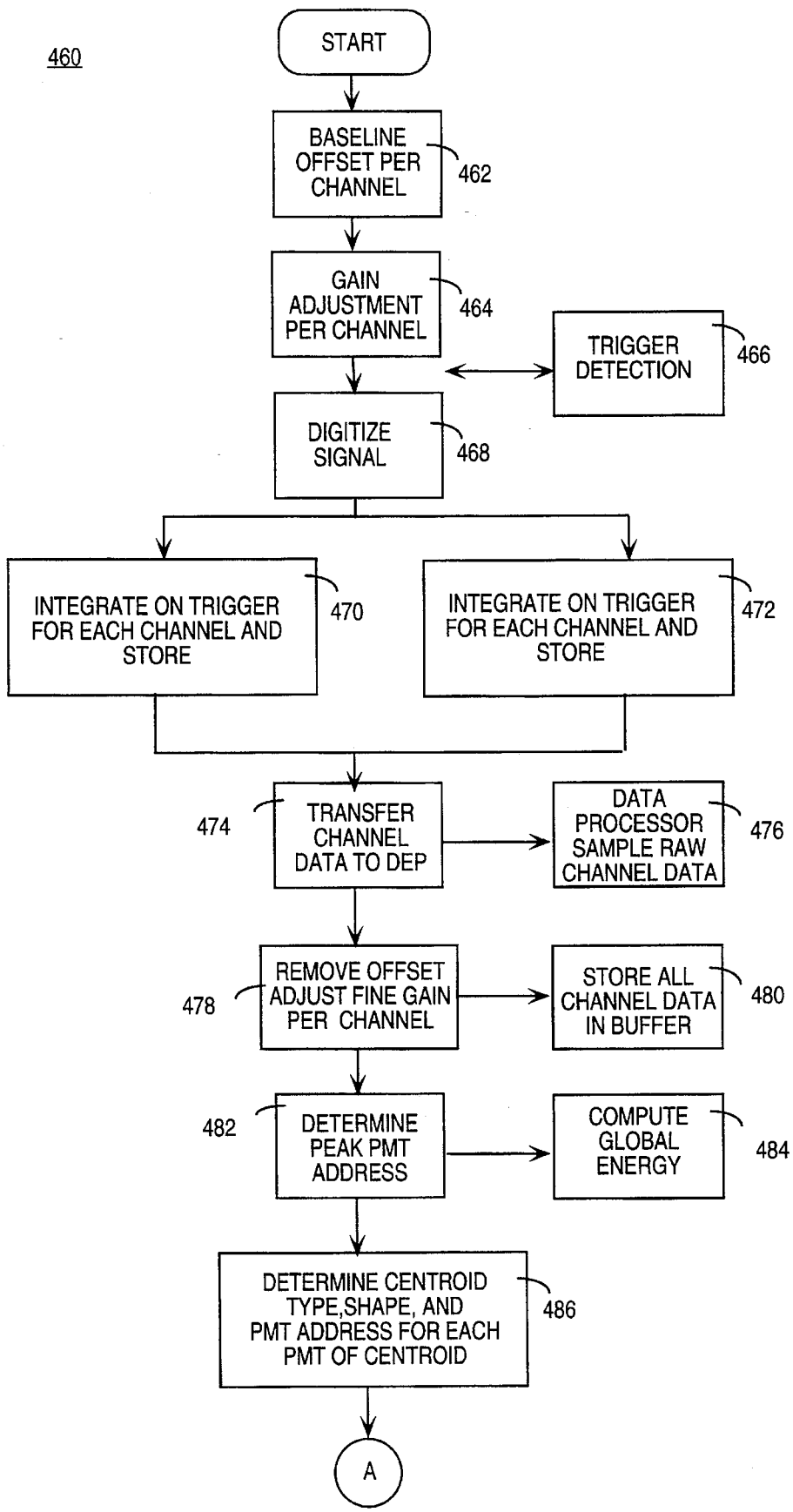
FIG. 4A and FIG. 4B illustrate an overall flow diagram of aspects of the Digital Event Processor of the present invention in SPECT of PET mode.
Figure 4B:
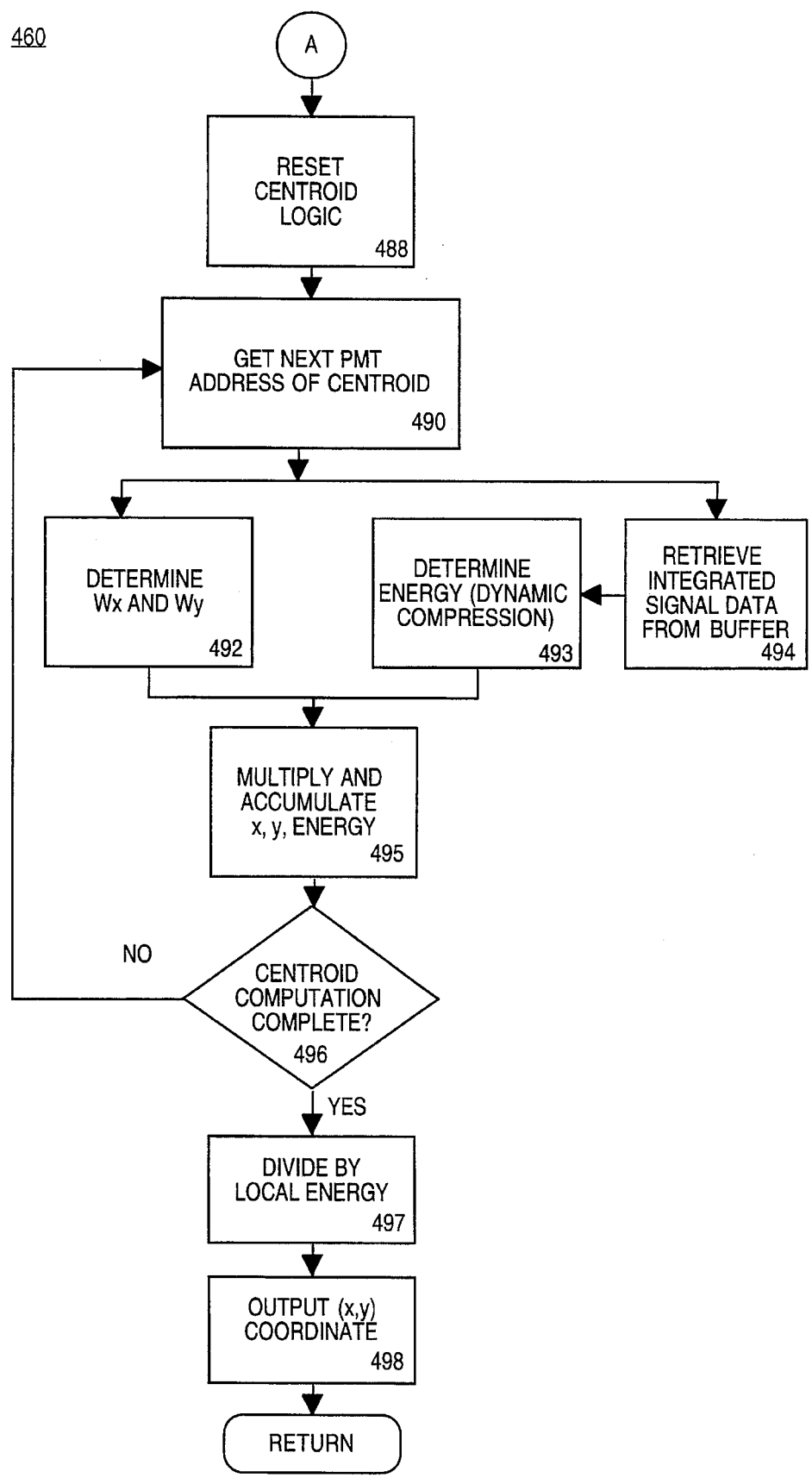

FIG. 4A and FIG. 4B are flow diagrams illustrating the general processing flow 460 of the present invention with respect to the operations of a single scintillation detector of the detector pair 80 and 80'. However, the flow 460 is performed by both detectors. It is appreciated that these flows pertain to both SPECT and PET imaging modes and that valid event trigger detection (block 466) would occur in coincidence for both detectors within PET imaging mode.

Refer to FIG. 4A where the procedure enters and receives a signal, over each PMT channel, and after convening the signal from current to voltage, performs a computer controlled baseline voltage offset for each channel at 462 and also performs a computer controlled coarse gain adjustment for each channel at 464. At block 468, each channel is digitized and also trigger detection is performed at 466 by the event detection logic of the present invention. Trigger detection is divided among four area zones across the surface of the each scintillation detector. As discussed above, in PET mode, a valid event trigger detection requires a coincidence signal between both detectors 80 and 80'. As discussed above, in SPECT mode, the zonal event detectors utilize a leading edge discriminator where in PET mode the zonal event detectors utilize a constant fraction discriminator. Dual integration takes place at blocks 470 and 472 wherein a first and a second valid event trigger may be used to integrate separate events occurring close in time. Both integration steps output integrated signals to the two stage FIFO circuit and at 474 these data values, per channel, are transferred to the DEP sequentially at the completion of an integration period. The raw data is sampled and made accessible to a data processor at 476 and this data is supplied to the calibration table at 478 which removes the baseline offset and also performs fine gain adjustment of the digital channel signal.

At 480, the data from the calibration table is stored for each channel in a buffer. At 482, the present invention determines the peak PMT by examining the channel data from the calibration table and also at 484 the global energy is determined by summing the digital data of each channel for the event. The peak PMT address is used as a measure of the coarse spatial location of the gamma event. At 486, the present invention PMT address table outputs a PMT cluster type and also determines the constitution of the PMT cluster based on the peak PMT address (and the selected resolution, e.g., fine or coarse, in one embodiment in SPECT mode.) At block 486, smaller sized PMT clusters are used in PET mode while larger sized PMT clusters are used in SPECT mode.

Referring to FIG. 4B, the flow 460 of the present invention continues at 488 where the circuitry used to perform the centroid computation is reset to initialize for the new computation. At 490, the sequence counter addresses the PMT address table so that the first PMT address of the selected PMT cluster is output. From this value, and also based on the PMT cluster type, the present invention generates an x weight (Wx) and a y weight (Wy) for the selected PMT address. Also, the buffer 325 contains and supplies the stored integrated signal data for this channel at 494 and at 493 the dynamic compression circuit outputs the dynamically compressed signal value for this channel. At 495, the x and y multiplication accumulation circuits are used to multiply the weight value times the dynamic compressed signal value and accumulate the result for the PMT cluster. At 495, a local energy accumulator also accumulates the local energy of the PMT cluster. At 496, the sequence counter increments and addresses the PMT address table for a next PMT address until the PMT cluster is complete (e.g., the stop indicator of table 335 is reached); flow returns to 490 if the PMT cluster is not complete. The above processing then continues with the next PMT address of the selected PMT cluster.

If the PMT cluster is complete, then flow continues to 497 where the x and y multiplication accumulation circuits are effectively divided by the local energy to produce a normalized (x, y) spatial coordinate for the gamma event. At 498, the pertinent information output from the DEP 300 (including the (x, y) coordinate and the total energy) is output to a computer system data processor or a correction board that performs energy, linearity and uniformity correction in known manners. When operating in PET mode, a pair of x, y, and energy information is generated from each detector 80 and 80' within a coincidence window. The pair corresponds to two points detected on the scintillation detector pair 80 and 80' corresponding to two gamma rays emitted in roughly opposite directions from a position-electron interaction. This pair is recorded by the acquisition computer system 1055 as corresponding to a discrete PET event and from this pair axial and transaxial angles of incidence are computed between the pair. The position of the positron interaction lies within the line connecting the two points of the pair. When operating in SPECT mode, the acquisition computer system 1055 records the detector, 80 or 80', to which the output data for an event applies.

ACQUISITION COMPUTER SYSTEM (DIGITAL PROCESSOR)

Figure 5:
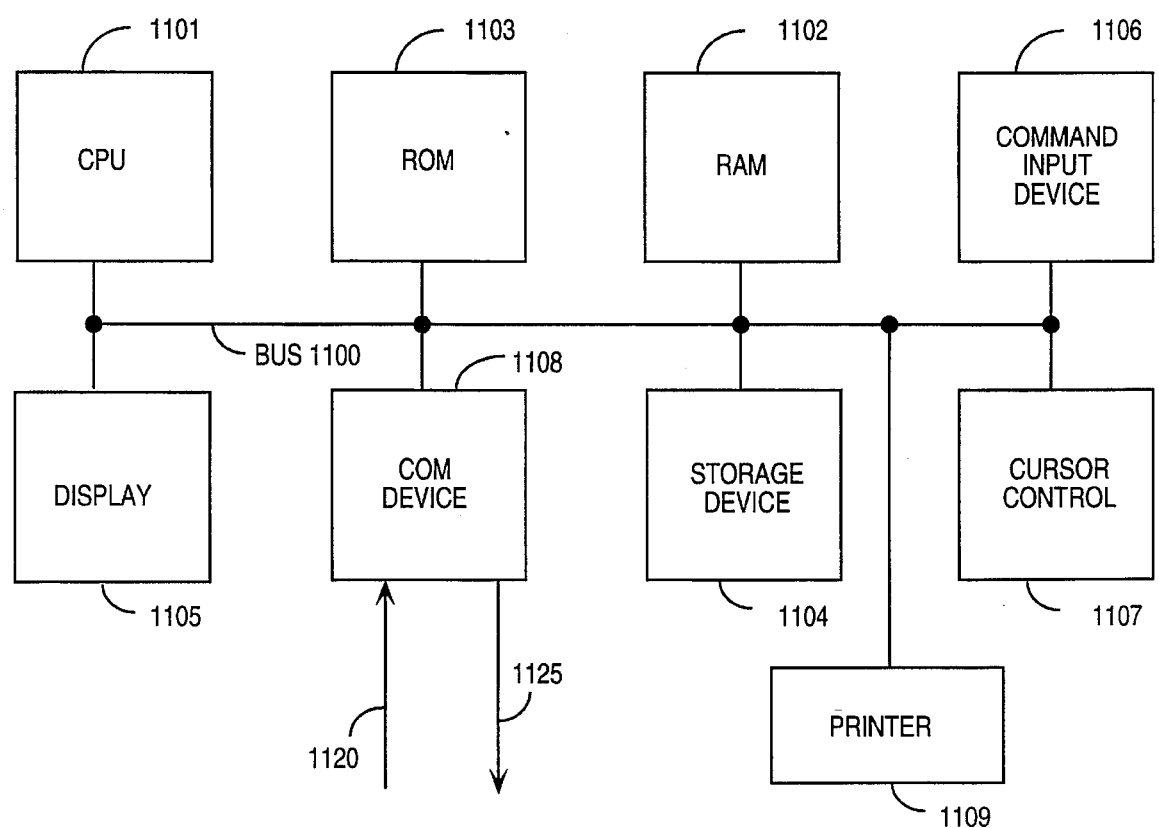
FIG. 5 is a diagram of a digital processor (computer system) and user interface of the present invention used, among other features, to automatically configure the camera system for SPECT of PET imaging modes.

Refer to FIG. 5 which illustrates components of a general purpose computer system 1112 (which can be implemented within the acquisition computer system 1055) that is capable of executing procedures of the present invention for controlling the DEP 300 circuit (e.g., control of baseline offset, gain, and trigger threshold) and for performing other recited functions. The computer system 1112 comprises an address/data bus 1100 for communicating information within the system, a central processor 1101 coupled with the bus 1100 for executing instructions and processing information, a random access memory 1102 coupled with the bus 1100 for storing information and instructions for the central processor 1101, a read only memory 1103 coupled with the bus 1100 for storing static information and instructions for the processor 1101, a data storage device 1104 such as a magnetic or optical disk and disk drive coupled with the bus 1100 for storing image information and instructions, a display device 1105 (which can also be external such as device 1065 of FIG. 1) coupled to the bus 1100 for displaying information to the computer user, an alphanumeric input device 1106 including alphanumeric and function keys coupled to the bus 1100 for communicating information and command selections to the central processor 1101, a cursor control device 1107 coupled to the bus for communicating user input information and command selections to the central processor 1101, and a signal generating device ("communication device") 1108 coupled to the bus 1100 for communicating command selections to the processor 1101. A hardcopy device 1109 (e.g., printer) may also be coupled to bus 1100.

The signal generation device 1108 includes a high speed communication port for communicating with both DEP 300 circuits. Input bus 1120 receives the data output from each DEP 300 such as signals PA 312, PD 317, GE 322, X 327, Y 332 and LE 337 over buses 1220 and 1222. Bus 1120 also supplies the raw data output from circuit 310 over bus 397 to the processor 1112 (with respect to both DEPs). Output from the processor 1112 are the control signals for controlling the fine and coarse baseline offset voltages (e.g., signals 212 and 214) and the PMT gain signal adjustment 220) for each channel. Processor 1112 also controls the trigger threshold 108. This processor 1112 also controls the state of the mode signal 1252 (FIG. 2A3) between SPECT and PET. Processor 1112 is also used to program register 1330 (FIG. 2C) to set the appropriate accumulation interval for both detectors 80 and 80'. The raw data sampled over bus 397 and the control signals generated by processor 1112 may be determined and adjusted in real-time by the present invention.

In PET imaging mode, the processor 1112 records together the X, Y, and energy values for a pair of gamma events that are detected in coincidence. The pair corresponds to two points detected on the scintillation detectors 80 and 80' corresponding to two gamma rays emitted in roughly opposite directions from a position-electron interaction. This coincidence information is used in the image generation procedures that are common to PET scanning. From the coincidence data of a pair of interactions, a line of intersection of each event can be determined which is projected through a given plane with the object. From these two points, an axial incidence angle and transaxial incidence angle are computed and recorded. In PET imaging, other mathematical manipulations allow a complete mapping of the three-dimensional distribution of the radionuclide within the organ to be determined. These procedures are well known in PET technology and are not discussed herein.

The display device 1105 of FIG. 5 (or the display unit 1065 of FIG. 1) utilized with the computer system 1112 of the present invention may be a liquid crystal device, cathode ray tube, or other display device suitable for creating graphic images and alphanumeric characters recognizable to the user. The cursor control device 1107 allows the computer user to dynamically signal the two dimensional movement of a visible symbol (pointer) on a display screen of the display device 1105. Many implementations of the cursor control device are known in the art including a trackball, finger pad, mouse, joystick or special keys on the alphanumeric input device 1105 capable of signaling movement of a given direction or manner of displacement. The keyboard 1106, the cursor control device 1107, the display 1105 and hardcopy device 1109 comprise the user interface associated with the image processor 1060.

DUAL INTEGRATION PER CHANNEL

The present invention provides multiple independent integrators per channel (e.g., two per PMT) in order to accurately process high count rates and to effectively reduce problems associated with pulse pile-up. This feature is particularly helpful for processing under PET imaging modes. Although described in a specific embodiment utilizing two integrators per channel, it is appreciated that the present invention system may be expanded to encompass a multiple number of integrators per channel (e.g., three, four, five, etc.). As will be discussed in further detail to follow, for each integrator added an additional stage within the serial latch circuit is required.

Figure 6A:
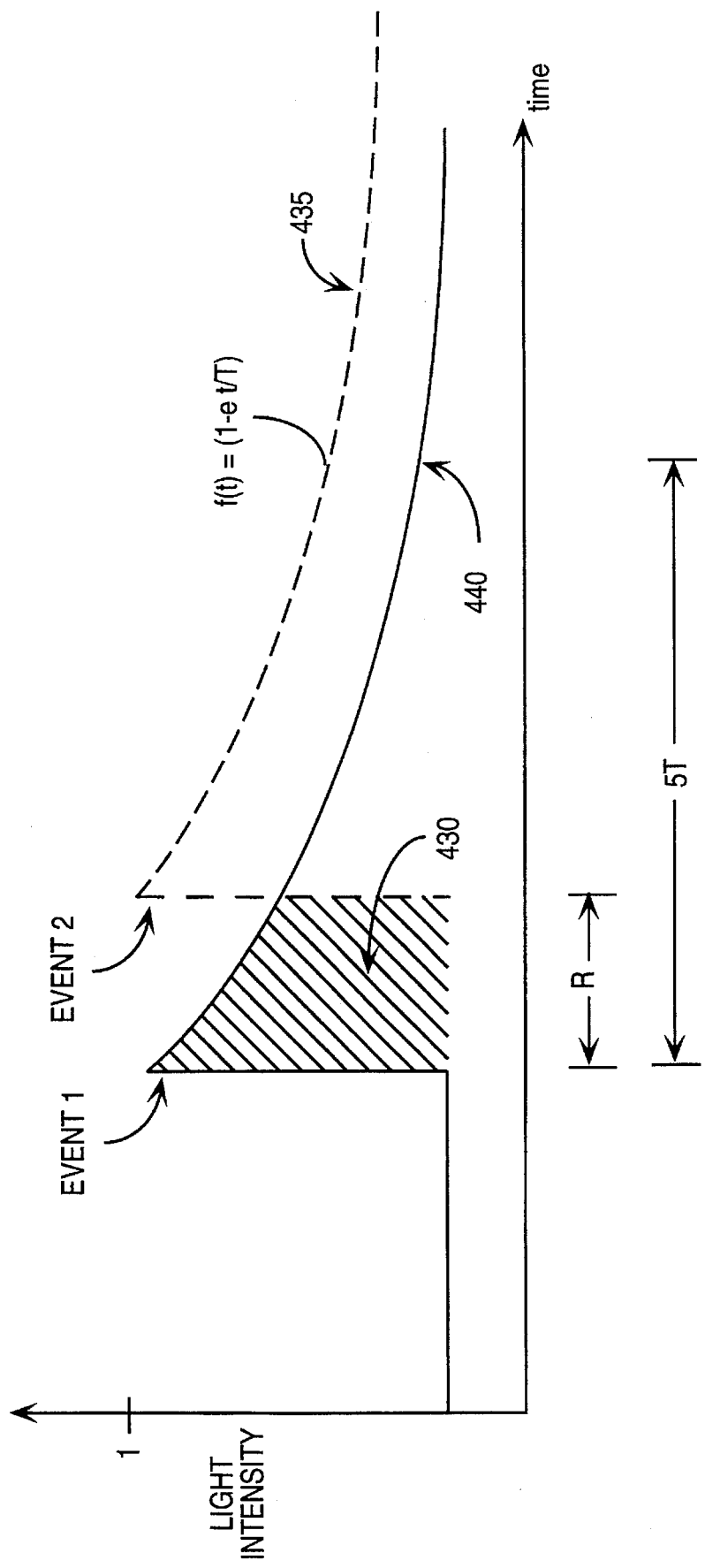
FIG. 6A represents the light intensity response for multiple events occurring close in time within the present invention.

FIG. 6A illustrates light intensity response (curve 440) over time for two events (in either PET or SPECT imaging modes). The light intensity response is a well known decaying exponential with a time constant, T. Event1 occurs and decays over time as shown by curve 440. Due to the characteristics of the crystal 81 used in the detector 80, at the end of 5T time intervals, most of the usable light intensity is radiated. However, there is some time value R, less than 5T, that can be used and gives a sufficient amount of energy to register event1 (e.g., energy associated with region 430). Prior art systems will attempt to utilize this decreased amount of energy (region 430) for registering events during periods of high count rate (e.g., if a second event occurs before 5T as shown as curve 435). However, this is not advantageous because as the separation between events decreases below 5T, less and less event energy is captured and spatial computations become less accurate. Further, at some point, (e.g., less then R) the temporal separation between two events will become too small and neither event can be registered. At higher count rates the spatial accuracy of the prior art systems decreases significantly.

The present invention, on the other hand, provides a mechanism for integrating the energy over 5T (for example) for both event1 and event2 because dual integrators are supplied per channel for all the PMTs of the array. Therefore, one integrator may sample and integrate the light intensity for event 1 over response 440 for 5T duration (or any other programmable duration) and the other can sample and integrate the light intensity for events over response 435. During periods of high count rate, the present invention does not sacrifice energy intensity when sampling each event when integrating over two events that closely occur in time. Furthermore, since two separate integrators are used, the present invention can accurately register two events even though their temporal separation is less than R. The present invention therefore provides higher accuracy at higher count rates over the prior art.

The present invention dual integrator embodiment utilizing two independent integrators is now discussed. As discussed with reference to FIG. 2C, the integration circuitry of circuit 280(*i*) for a given channel includes two integrators 238 and 240 each having independent accumulators and each coupled (via a mux 241) to a two stage sample and hold circuit (latch 242 and latch 244). Each integrator is independently triggerable and separately and independently integrates its associated channel signal over a programmable period. Trigger signals are transmitted over bus 130 and when received, act to reset the accumulator of an idle integrator. At the end of the programmable integration interval maintained by register 1330 (FIG. 2C), for an event, the present invention transfers the data of the second stage (244) to the DEP 300, moves the data of the first stage 242 to the second stage and moves the data of the accumulator of the completed integrator into the first stage of the hold circuit. This way, both integrators may be sampling, simultaneously, different events. They can each be independently triggered and at the end of the programmable sample period, the accumulator stores its result in the two stage hold circuit.

The above procedure operates most accurately when the two integrated events are sufficiently separate from one another such that their energy dissipation across the detector does not overlap or interfere in the integration computation. For instance, refer to FIG. 7 which illustrates an exemplary PMT array. A first event occurs over PMT 7, therefore the PMT cluster 75 is composed of PMTs 1, 8, 20, 19, 36, 18, and 7. The trigger pulse resets integrator 238 (per channel) which then integrates the energy for the first event for all 55 channels. Before the integration is complete for this first event, a second event occurs over PMT 38, so the PMT cluster 73 is composed of PMTs 38, 37, 22, 23, and 39. Integrator 240 (per channel) is reset and integrates the energy associated with the second event for all 55 channels. Since PMT cluster 75 and 73 are sufficiently separate, the contribution of energy associated with the second event over channels 1, 8, 20, 19, 36, 18 and 7 is relatively small and does not interfere with the integration computation for the first event. Likewise, the contribution of energy associated with the first event over channels 38, 37, 22, 23, and 39 is relatively small and does not interfere with the integration computation for the second event.

At the end of the computation for the first event, the integrated channel signal data of latch 244 is output to the DEP 300, for a given detector, the integrated channel signal of latch 242 is output to latch 244 and the value of the accumulator of integrator 238 is output to latch 242. At the end of the computation for the second event, the integrated channel signal of latch 244 is output to the DEP, the value of latch 242 is output to latch 244 and the value of the accumulator of integrator 240 is output to latch 242. The first and second events will be processed by the DEP 300.

Figure 6B:
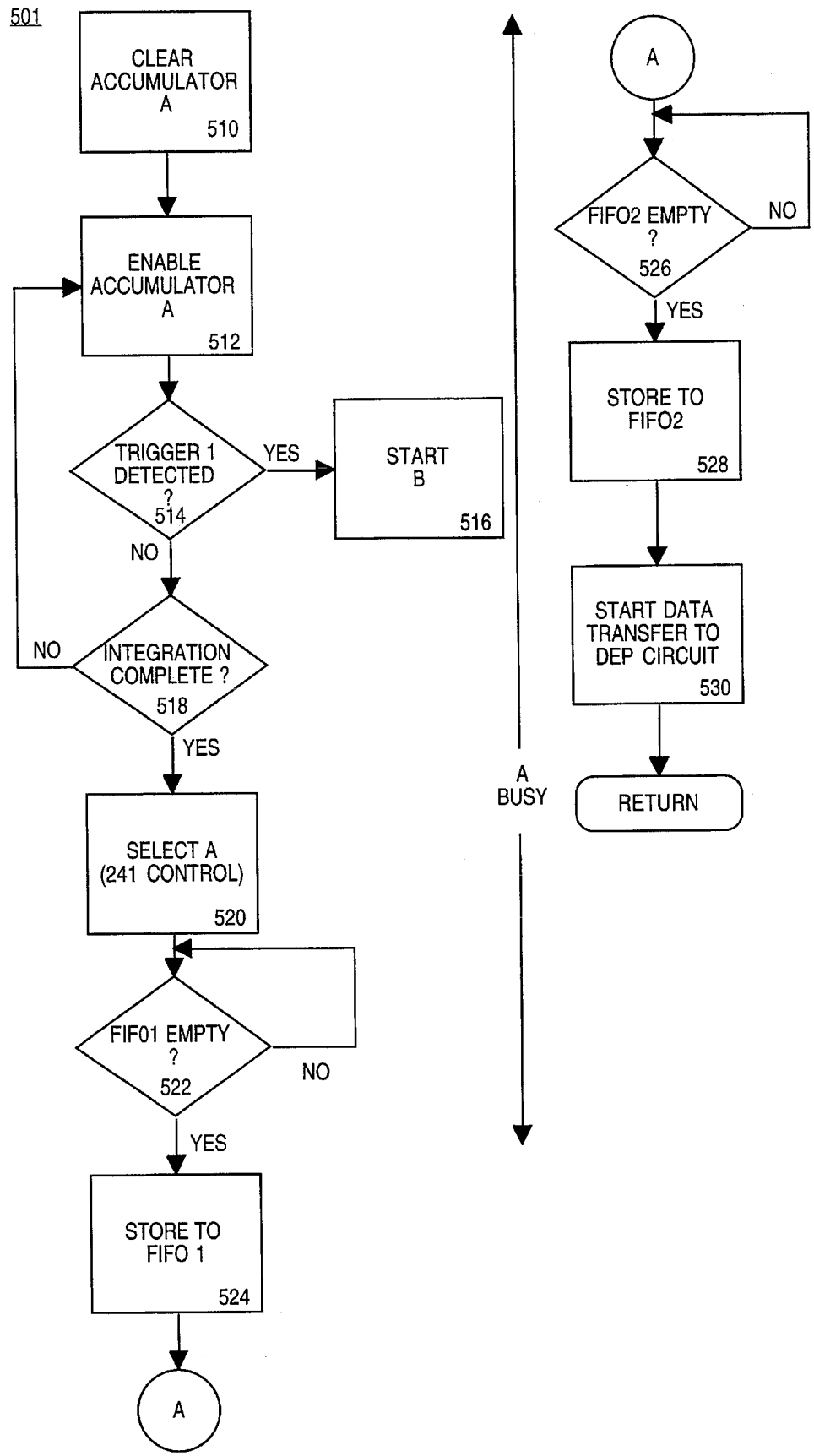
FIG. 6B illustrates a flow chart of the timing performed for dual integration on a particular channel using a programmable integration period.

FIG. 6B illustrates in more detail the process performed by the present invention to perform dual integration per channel. Each channel of each detector performs this process. The process shown 501 represents the process for integrator A but it is appreciated that the process for B (block 516) is identical except that the "B" control signals are used. As shown, the process starts at 510 in response to a valid event trigger signal, Start(t0). Then, the A accumulator is cleared (e.g., integrator 238) by assertion of a CLRACCA control signal and at 512 this accumulator is enabled to integrate by assertion of an ENACCA control signal. At block 514, if Start(t1) is detected then at block 516 the process for integrator B is started and operates concurrently with process 501. If not, then at block 518 it is checked if the programmable duration integration for A is complete. If so, not then the process returns to 512 where integration continues.

When integration for A is complete over the programmable interval, at block 520 a control signal for MUX 241 selects the data from integrator 238. At block 522 FIFO1 (242) is checked if empty and if empty, at block 524 the data is latched into FIFO1. At block 526 if FIFO2 (244) is empty then data from FIFO1 is latched into FIFO2 at block 528. At block 530 the data transfer from FIFO2 to the Digital Event Processor is started for all channels. During the period from block 510 to block 522 the A integrator is busy. It is appreciated that there is only one valid event trigger signal and it is classified as Start(t0) or Start(t1) by its temporal relationship to the other trigger signal. During the A busy period, a trigger signal will cause the B process to start. The register 1330 (FIG. 2C) can be loaded with the programmable integration period at any time but is typically loaded before an imaging session is started and is not altered during the session.

VARIABLE PMT CLUSTER CONSTITUTION

As discussed above, the PMT address table circuit 335 of the present invention contains a lookup table that provides the addresses of the group of PMTs that constitute the PMT cluster for a given event based on the peak PMT for that event (supplied from circuit 320) and based on a count value supplied over bus 357 from the sequence counter 390. A centroid is computed (using a centroiding computation) based on the PMT cluster to arrive at a spatial coordinate value of the event. In this way, the PMT cluster constitution of the present invention varies for each peak PMT. According to the present invention, also associated with each PMT of the detector array is a type registration or classification that describes the type of PMT cluster that is formed.

Due to the high count rate experienced during PET imaging, the present invention, via the computer system 1112, generally controls the size of a PMT cluster to be no more than seven PMTs per cluster while in SPECT mode the typical PMT cluster size is allowed to include more PMTs, such as 19 PMTs per cluster. The exact number of PMTs per cluster is not essential, however, the present invention advantageously allows cluster sizing to be reduced when operating in PET mode while PMT cluster sizing is increased during SPECT mode. Therefore, during initialization of a PET imaging mode of operating, the system 1112 automatically controls the programming of the present invention to select and utilize a reduced number of PMTs per cluster while during initialization of a SPECT imaging mode of operating, the system 1112 automatically controls the programming of the present invention to select and utilize an enlarged number of PMTs per cluster. Specifically, to initialize under either PET on SPECT imaging mode, computer system 1112 loads a predefined PMT cluster table (FIG. 8) into circuit 335 so that the proper PMT cluster sizes are available. The predefined tables (one for PET and one for SPECT) can be stored in unit 1102 or 1103 or 1104, for instance, before downloading into circuit 335.

Figure 7:
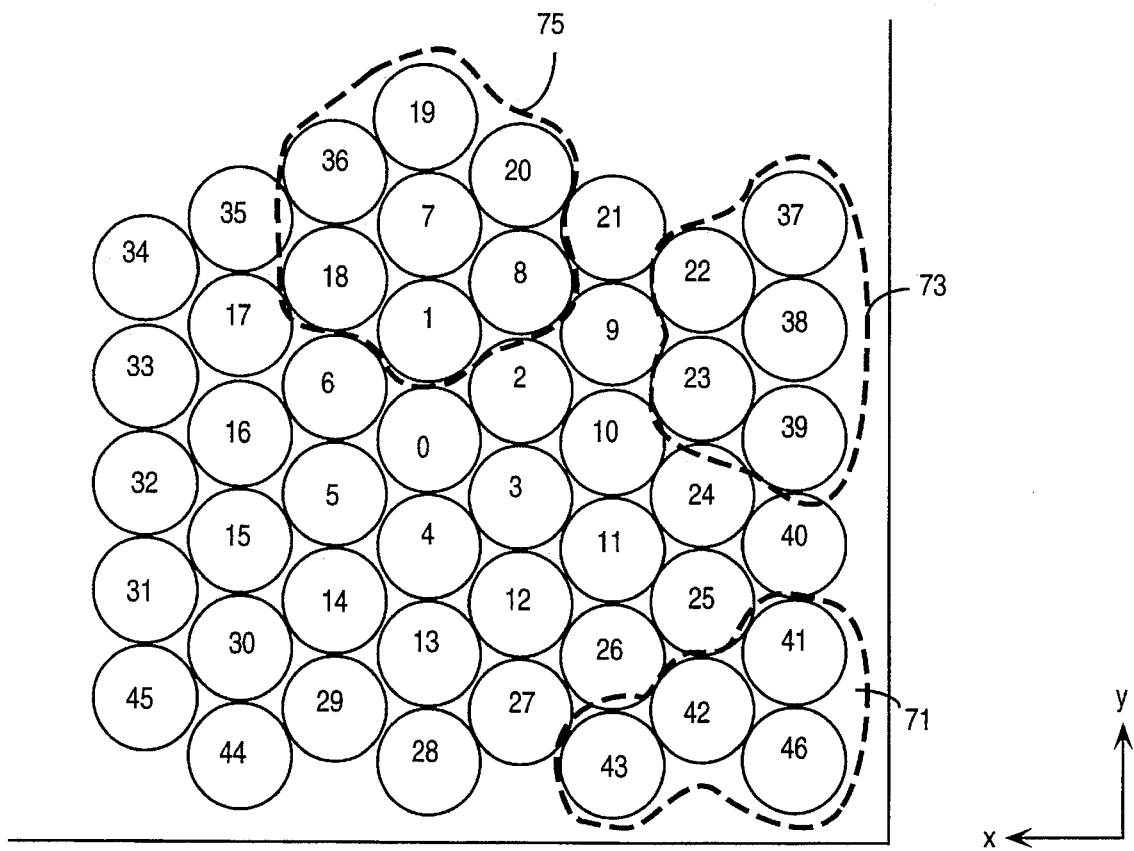
FIG. 7 illustrates an exemplary PMT array of a detector of the present invention and illustrates three different cluster types.

With regard to variable cluster shape, the present invention provides four different types of exemplary PMT clusters: 1) normal; 2) long edge; 3) short edge; and 4) corner. The normal PMT cluster anticipates the peak PMT to be located in an area of the PMT array that can be surrounded by other PMTs such that the PMT cluster is substantially symmetrical about both axis. Such a PMT cluster is shown in FIG. 7 as PMT cluster 75 with PMT 7 as the peak PMT which is surrounded by outer PMTs. The determination of the peak PMT gives a coarse spatial location for the event and the present invention PMT address table 335 is able to utilize this coarse location of the event in determining the PMT cluster constitution for that event so that the fine spatial location may be provided via the centroid computation of the DEP 300.

Two PMT cluster types (long edge and short edge) correspond to PMT clusters having peak PMTs located on the edge of the detector PMT array. Edge PMT clusters are not symmetrical about one axis. The PMT array of the present invention is rectangular and contains a long edge and a short edge and depending on the edge location of the peak PMT, the PMT cluster defined thereby can be a long edge PMT cluster or a short edge PMT cluster. The PMT clusters of these types are different because the light distribution at the long and short edges are different. An edge type PMT cluster is shown in FIG. 7 as PMT cluster 73 having PMT 38 as the peak PMT. The fourth type of PMT cluster of the present invention is a corner PMT cluster and the PMT of this type is located in a corner type of the PMT array, such as PMT cluster 71 of FIG. 7 having peak PMT 46. This PMT cluster type is not symmetrical about either axis. It is appreciated that the above PMT cluster types are exemplary and many other PMT cluster types may be utilized within scope of the present invention depending on the particular geometry of the PMT array utilized and the geometry of the detector head.

It is appreciated that for a given peak PMT address, the type value for the PMT cluster can change depending on the selected resolution of the spatial computation. For instance, a normal type PMT cluster at high resolution having the same peak PMT may be different from the PMT cluster generated at low resolution for the same peak PMT (which may be an edge type cluster). This is the case because at least in SPECT mode, at higher resolution, more PMTs are required (e.g., 17 or 19) to complete the PMT cluster rather than 7 for the low resolution cluster and these additional PMTs may overrun the edge of PMT array.

Type fields are important because the PMT cluster type will effect the x and y weights assigned to a particular PMT of a particular PMT cluster in the spatial computation. For instance, PMT cluster types that are symmetrical about only one axis (e.g., edge types) will have modified weight values assigned to those PMTs of the PMT cluster that are located along the axis that is not symmetrical. For instance, refer to FIG. 3 which illustrates a spatial computation based on a normal PMT cluster type. The spatial coordinate is computed from an average of a sum based on the weight of a PMT multiplied by the integrated channel signal of the PMT for each PMT of the PMT cluster. The weight values for the PMTs must be adjusted in the computation of a spatial coordinate along an axis for which a PMT cluster is not symmetrical. Referring to FIG. 3, assume that PMTs 2 and 3 were not available because PMT 0 was located along an edge. The resulting PMT cluster is composed of PMTs 0, 1, 6, 5, and 4 and is not symmetrical about the X axis. For the coordinate computation of the X axis coordinate, the average calculation would be skewed or shifted to the left because the PMTs of the right (e.g., PMTs 2 and 3) are missing. Therefore, the weight values of the PMTs of the resulting PMT cluster must be reduced to compensate for the skew to the left. The same is true for corner PMT clusters, however the weight values must be adjusted for the computation of both coordinates because corner PMT clusters are not symmetrical to the X or Y axis.

The weight adjustment of the PMTs based on the PMT cluster type field is made by the weight circuit 345 and will be discussed further below.

Refer to FIG. 8 which illustrates the format of the PMT address table circuit 335 for low resolution selection in SPECT mode or for PET mode. The PMT address table circuit 335 is addressed by the peak PMT address value and also addressed by the count value (here shown from zero to n). Circuit 335 contains an entry for each of the 55 PMTs of the detector array. For each peak PMT, the circuit 335 outputs a PMT cluster type value and the PMT addresses of the PMT cluster. The output of the circuit 335 is (1) a PMT cluster type value and (2) the PMT addresses (a "PMT list") of the PMTs of the PMT cluster defined by the peak PMT address. Since the PMT clusters are programmable and of variable size and PMT number, a "stop" indicator is placed at the end of the PMT list (or included as part of the last PMT address entry). Exemplary data is shown in FIG. 8 and corresponds to the PMT clusters shown in FIG. 7. The first entry shown of FIG. 8 relates to PMT cluster 74 of FIG. 7 and PMT 7 is the peak PMT and the PMT cluster is a normal type having PMTs 1, 8, 20, 19, 36, and 18. Entry 38 of FIG. 8 relates to PMT cluster 73 of FIG. 7 and is an edge type PMT cluster. Entry 46 of FIG. 8 relates to PMT cluster 71 of FIG. 7 and is a corner PMT cluster.

The data stored in the memory circuit 335 that is used to formulate the PMT clusters for each peak PMT can be programmable and may be downloaded from the computer system 1112 at initialization of an imaging mode or between SPECT/PET selections. In such an embodiment, different datasets may be loaded into the memory circuit 335 for different configurations. Alternatively, the circuit 335 may be implemented using static ROM memory. In one embodiment, two separate PMT cluster tables (FIG. 8), one for PET and one for SPECT imaging, can be loaded into circuit 335 with a mode selection (line 1252) being fed into circuit 335 for selection between the two tables for PET and SPECT mode.

Based on a clock signal, the sequence counter 390 of the present invention will present the count field over bus 367 (one at a time) and this count value will address the circuit 335 along with the peak PMT address to output (1) the PMT cluster type and (2) the PMT address of the PMT cluster as shown in FIG. 8.

It is appreciated that depending on the desired resolution (or count rate) of the gamma camera, or the operational mode of the camera (e.g., PET or SPECT), the PMT address table 335 of the present invention will output different sized PMT clusters for each PMT cluster type. For instance, if high resolution spatial determination is required, or if SPECT imaging is being performed, or low count rate is expected, then the PMT clusters will be increased in size to include 17 to 19 PMTs for a normal PMT cluster (instead of seven for normal cluster types in low resolution). As discussed above, if PET imaging is desired then 7 PMTs per cluster are supplied to allow high count rate with minimum pileup. Edge and corner PMT clusters will be increased accordingly in number. Therefore, in an alternative embodiment of the present invention, the PMT address table 335 receives an additional signal indicating low or high resolution and this signal will address the table to supply the appropriate centroiding information based on the required resolution. Alternatively, the entire table 335 may be reloaded with a different data set to vary the resolution in SPECT mode.

Given the design of the PMT address table of FIG. 8, the number of PMTs of a given PMT cluster may easily be increased since the stop indicator, which marks the completion of the PMT cluster, is readily adjusted. Further, as stated above, the PMT cluster type corresponding to a particular peak PMT address may vary from low to high resolution settings, or for PET or SPECT imaging modes.

VARIABLE PMT WEIGHTS PER PMT

According to the present invention, the weight table circuit 345 outputs x and y coordinate weights for each PMT of the PMT cluster based on the PMT address and the PMT cluster type information, both of which are generated by the PMT address table 335. FIG. 9 illustrates the weight table circuit 345 of the present invention. Depending on the type of PMT cluster (e.g., normal type, long edge type, short edge type, corner type, or other type) that the PMT is contained within, the x and y coordinate weights output from the circuit 345 for the PMT will vary. For each PMT address (e.g., from PMT0 to PMT54), the present invention provides a separate and programmable weight value for each coordinate computation (e.g., Wx and Wy) that varies by PMT cluster type. The values Wx are output over bus 362 and the values Wy are output over bus 357. As will be discussed below, the determination of the peak PMT gives a coarse spatial location for the event and the present invention weight table 345 is able to utilize this coarse location of the event in determining the proper weight values to assign the PMTs of the PMT cluster. The fine spatial location is computed via the centroid computation of the DEP. In such manner, the PMT address value signal over bus 372 and the type signal over bus 377 address the circuit 345.

Since some PMT clusters are not symmetrical about a given axis, for instance the X axis or Y axis for an edge type PMT cluster, the weight values associated with these axis are adjusted or varied in order to balance out the coordinate computation. This is accomplished by the present invention in order to compensate for the missing PMTs (of one axis) that are not available to provide a symmetric computation. For corner PMT clusters, the weight values associated with both axis are adjusted to compensate for the missing PMTs (of both axis) needed to provide a symmetric computation. Typically the weight values are decreased for certain PMTs in order to perform the above balancing. The values weight table 345 of the present invention may also be developed empirically based known events for certain locations.

Further, other factors such as the crystal boundaries, optical interfaces, and PMT photocathode properties can make the PMT contribution different depending on the location of the event. Since, the peak PMT address gives some indication of the coarse location of the event, the weight table 345 can compensate for the above factors by providing variable weights.

Therefore, the present invention provides the ability to adjust or alter the weight values for a given PMT depending on the PMT cluster type in which the PMT is located. Depending on the location of the peak PMT, the weight values for the PMTs used in the centroid computation may alter. These weight values are also dependent on the peak PMT address since the peak PMT address defines the PMT cluster type within the present invention. The ability to assign different weighting factors based on the peak PMT location permits higher accuracy in the centroid computations and reduces the demands on the correction processing steps. This contributes to allowing the detector 80 to have larger field of view without increasing the crystal dimensions.

The data stored in the memory circuit 345 of FIG. 9 that is used to provide the variable weights for each PMT can be programmable and may be downloaded from the computer system 1112. In such an embodiment, different datasets may be loaded into the memory circuit 345 for different configurations. Alternatively, the circuit 345 may be implemented using static ROM memory.

In operation, as the counter 390 counts sequentially, the PMT address table 335 outputs a sequential listing of PMT addresses within the PMT cluster. The type signal generated by bus 377 addresses the MSBs of the of the memory 345 and the PMT addresses are the LSBs. As each PMT is generated over bus 372, the memory circuit 345 generates an X and Y weight value (over buses 357 and 362) associated with the current PMT output over bus 372. This information is fed to the centroiding circuitry for computation of the spatial coordinate a the gamma event.

AUTOGAIN CORRECTION

As will be discussed further below, the autogain calibration of the present invention contain two phases: (1) an initial calibration; and (2) a routine calibration. The routine calibration can be performed with the collimator installed or with the collimator removed. Autogain correction, to the extent it operates in conjunction with a collimator is applicable only to SPECT imaging modes of operation because the PET imaging modes do not require collimators.

The present invention provides a procedure for automatically calibrating the gain of each PMT channel without removing the collimator during the routine gain calibration phase. This is beneficial at least since the gain calibration may be performing during periods of quality control without removal of the collimator while imaging a sheet source (e.g., Co-57) and thus saving time and effort. Further, since collimator removal is a laborious and time consuming procedure, the automatic gain calibration of the present invention provides an efficient mechanism for gain correction. The computer system 1112 adjusts a preamplification gain (Gp) for each PMT by using coarse and fine gain values. The coarse gain adjustment is accomplished by generating a digital gain value that is converted to an analog signal by a DAC and applied at input 220 of the preamplification circuit (280($i$)) for each channel ($i$). The fine gain adjustment is implemented in the calibration table 315 as a look-up table. The computer system 1112 stores the current value of both the coarse and fine gain (Gp) for each channel. The computer system 1112 also performs the automatic gain adjustment procedure as will be discussed in further detail below.

The effective gain associated with each PMT channel has two separate components. The first component is the physical gain associated with the individual PMT itself (Gt) and this gain is established by the physical characteristics of the PMT. The second component is the corresponding preamplifier gain (Gp). As is known, the PMT physical gain, Gt, may vary over time and change in the long term (e.g., over hours or days). These variations in the Gt create the problem that the present invention solves by adjusting the Gp gain associated with each PMT channel individually to compensate for the changes in Gt to obtain a stable (fixed effective gain) for each PMT channel.

The preamplification gain, Gp, contains two components. For each channel, the first component of the preamplification gain Gp is the gain applied to the output channel signal within the preamplification stages, 280($i$), for each channel (e.g., coarse adjustment); this component is applied at gain circuit 222 via input 220. A second component (e.g.,. fine adjustment) of the preamplification gain Gp is supplied by the calibration table 315. If the gain of a particular channel does not vary by more than some small percentage (e.g., 5%) then the gain value found within the calibration table for that channel is altered, not the gain applied at the preamplification stage for that channel.

The effective gain, Gt*Gp, is to remain fixed over time to yield the same output signal of a particular radionuclide emitting photon with distinct energy. The fixed gain of each PMT channel will give stable x, y coordinates and total energy values which will increase the time between required recalibration of the camera's energy, linearity and uniformity correction factors. Another advantage of the autogain calibration of the present invention is that it brings back the camera to its state when it was initially calibrated and when uniformity correction factors were generated.

In view of this, since the gain Gt may vary due to the physical characteristics of the PMT, the present invention compensates for this variation by altering the computer controlled value of the Gp gain that is applied to data from each channel. In this way, the automatic gain correction procedure of the present invention will maintain the resultant gain (e.g., Gt*Gp) at a fixed value for each channel. The actual value of this fixed amount can be determined and/or measured during manufacturing or at the site of installation and operation of the scintillation detector. Since energy, linearity and uniformity corrections are based on a fixed gain of each of the calibrated photomultiplier channels of the array, it is advantageous to maintain this calibration throughout the operational cycles of the gamma camera system so that the gains of the PMT channels are closely calibrated to match the gain when the energy, linearity and uniformity correction factors were calibrated.

Figure 10:
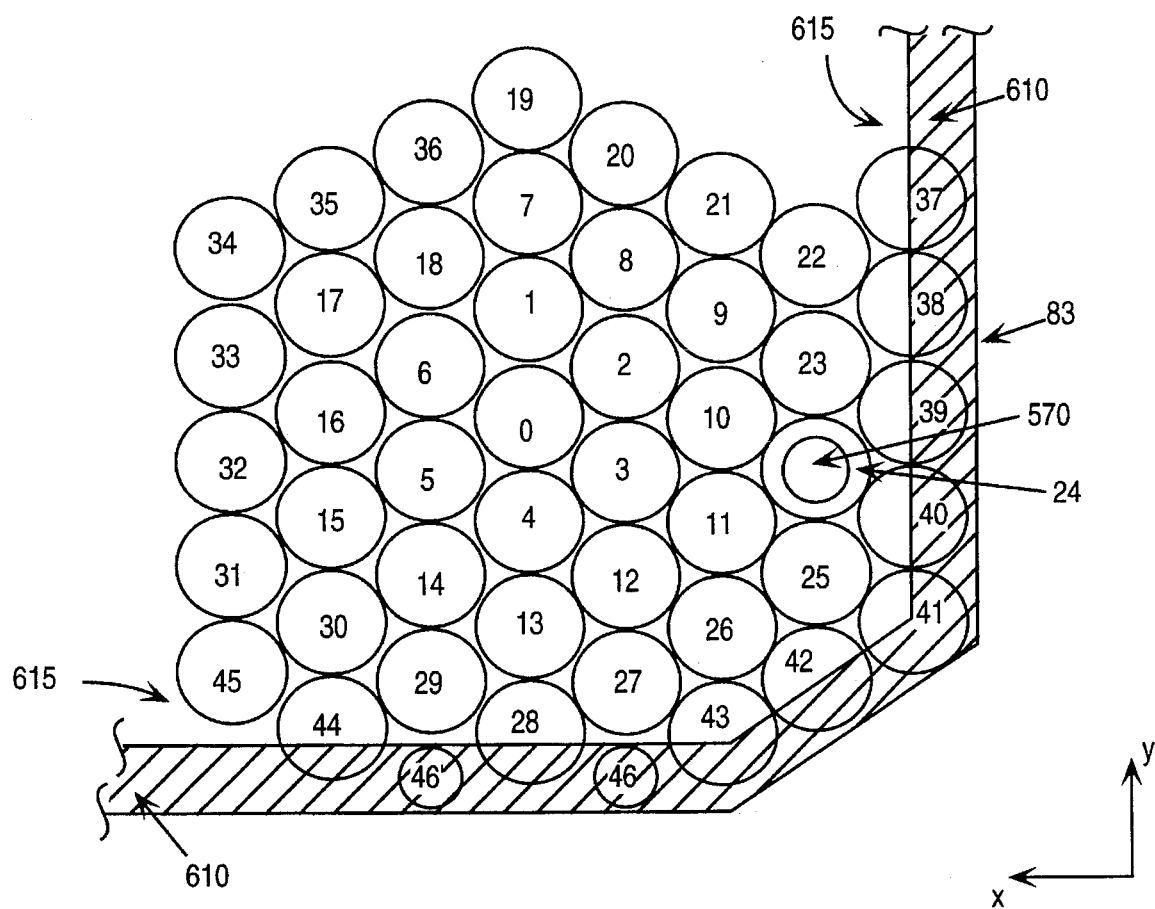
FIG. 10 illustrates a plane view of a collimator (with edges) as positioned over a PMT array of the present invention in SPECT imaging mode.

Central and Obscured PMTs. FIG. 10 illustrates an exemplary PMT array of the present invention as well as a collimator 83 that is positioned in front of the PMT array. The collimator 83 contains an inner region 615 composed of a honeycomb of holes with lead septas allowing radiation of a particular incident angle to pass there through. The collimator 83 also contains a second region (edge region) 83 that is solid lead and partially and fully covers some edge and corner PMTs. PMTs having their surfaces located totally under region 615 are the central PMTs (centrally located)

and PMTs having a portion of their surfaces located under region 610 are called obscured PMTs. The present invention provides an automatic procedure and apparatus for calibrating the gain factors of each PMT of the array (including those PMTs that are obscured) while leaving the collimator installed during the routine calibration procedure. Since PET imaging does not utilize a collimator, PET imaging does not utilized obscured PMTs.

Each PMT has an area 570 associated with it directly over the PMT surface, see region 570 of PMT 24 for instance(in FIG. 10). Although only one area 570 is shown, it is appreciated that each PMT of FIG. 10 has an associated region 570 located above its individual surface. The actual shape and size of the region 570 can be varied (e.g., it may circular, square, hexagonal, etc.). In the preferred embodiment of the present invention, this area 570 is circular and covers substantially all of the area above a given PMT. This central region 570 will be used for calibration of the preamplification gains (including adjustment of the calibration table) of each PMT when the collimator is removed and each centrally located PMT when the collimator is installed. (Some PMTs can be located only partially over the NaI crystal layer and therefore will receive less light.)

Figure 11:
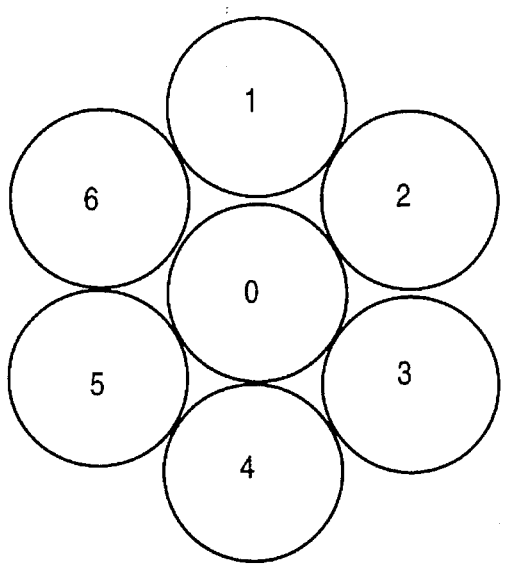
FIG. 11 illustrates placement of centrally located PMTs and obscured PMTs and an exemplary strip area associated with an obscured PMT in SPECT imaging mode.
Figure 11:
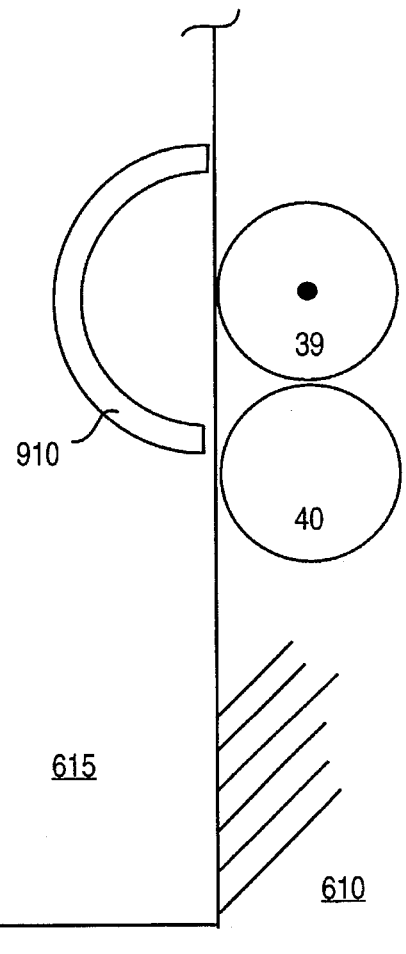

Strip Regions 910. FIG. 11 illustrates specialized regions 910 (one associated with each obscured PMT) utilized by the present invention for performing gain calibration for the obscured PMTs of the scintillation detector. FIG. 11 illustrates two obscured PMTs 39 and 40 that are obscured by the collimator's solid lead region 610 (when installed) as well as a group of centrally located PMTs (0–6) that are situated inside region 615 where the collimator consists of holes permitting radiation to pass through. The region 910, or "strip" area is associated the obscured PMT 39 but a separate strip area 910 is also associated with each obscured PMT of the scintillation detector. FIG. 11 illustrates only one such strip region 910 associated with obscured PMT 39. This region 910 may be of a variety of different geometries and in the preferred embodiment is semi-annular and extends in an arc fashion surrounding a region that is located substantially equidistant from the center of its corresponding obscured PMT 39.

It is appreciated that this strip region 910 may vary in size and shape consistent with the present invention. However, in a preferred embodiment of the present invention, this region 910 is located such that it extends substantially equidistant from the center of its associated PMT and generally adopts a thin shape as shown in FIG. 11. A further requirement of strip 910 is that it extend substantially (if not fully) within the region 615 of the collimator that allows gamma rays to pass through.

When the collimator is installed onto the scintillation detector, the present invention is not capable of performing gain calibration on the obscured PMTs utilizing an area located directly over their surfaces, such as region 570, because no gamma events are detected under region 610 due to the presence of the collimator's edge. Therefore, the present invention performs gain calibration for obscured PMTs by recording information associated with gamma events that are detected within the exposed strip area 910 associated with each obscured PMT. In general, the present invention measures the integrated channel response of an associated PMT, e.g., PMT 39, in response to all gamma events that occur within the strip area 910 over a sample interval during the initial calibration. This information will be used to adjust the gain of obscured PMT 39.

Figure 12:
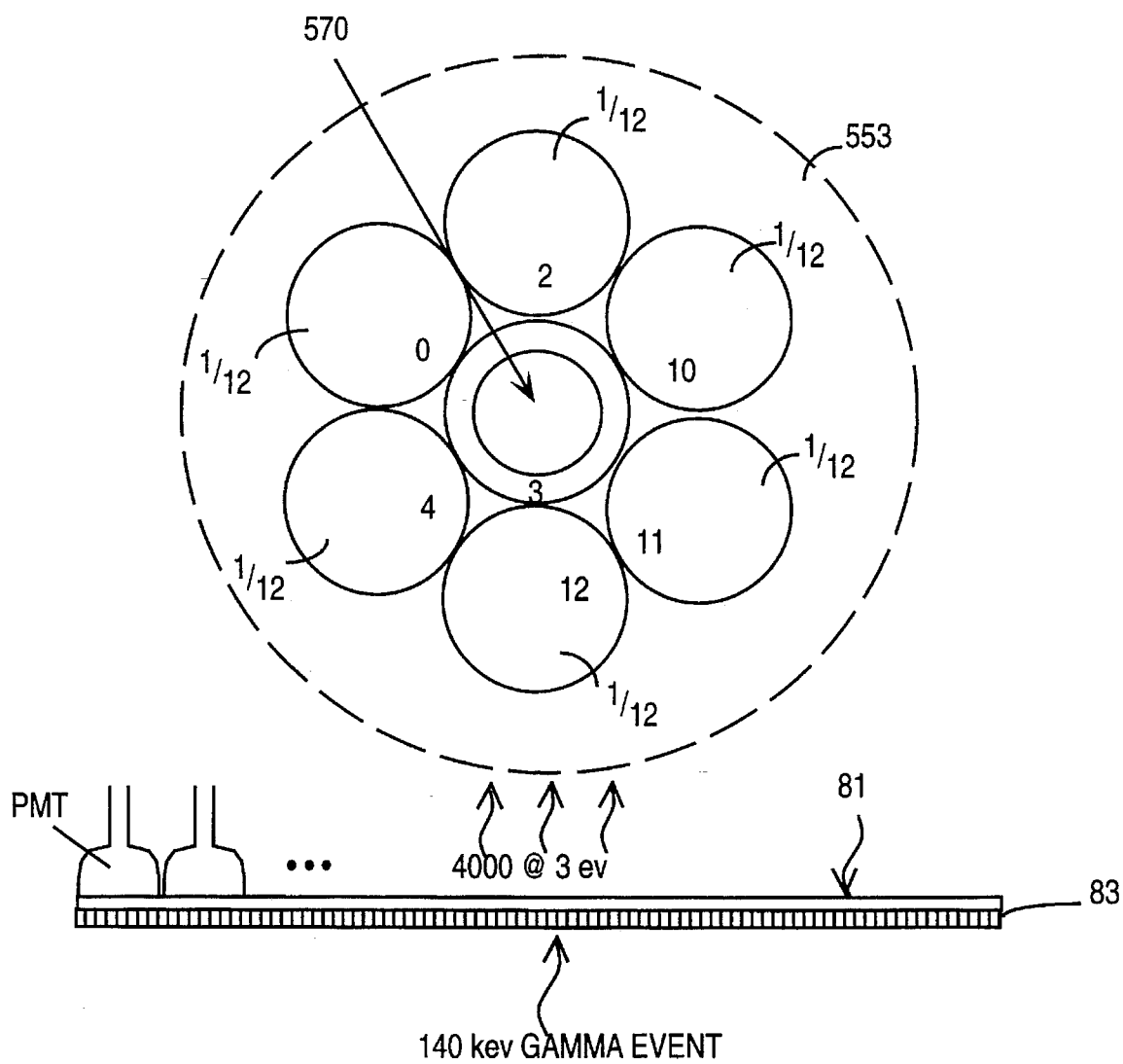
FIG. 12 illustrates energy absorption percentages for a typical PMT centroid arrangement for a gamma event.

PMTs of a PMT cluster detect different amounts of energy responsive to a gamma interaction depending on their spatial relationship to the interaction. Refer to FIG. 12 which illustrates an exemplary and typical PMT cluster 553. For a given gamma interaction (e.g., 140 keV), approximately 4000 separate 3 eV visible scintillation photons are emitted from the crystal 81 and of which only 50% are detected. Depending upon the size of the PMTs, if the gamma interaction occurs within the center of region 570, the center PMT will collect and report approximately 45 percent of the detected light energy. The surrounding adjacent six PMTs each collect approximately 8% of the detected energy. For a number of detected gamma events located near the center of region 570 of the center PMT, the center PMT should produce an integrated output voltage proportional to approximately 1000 3 eV light photons. Each of the adjacently surrounding PMTs should output a integrated mean voltage proportional to 160 3 eV light photons for the gamma events occurring within 570.

Figure 13A:
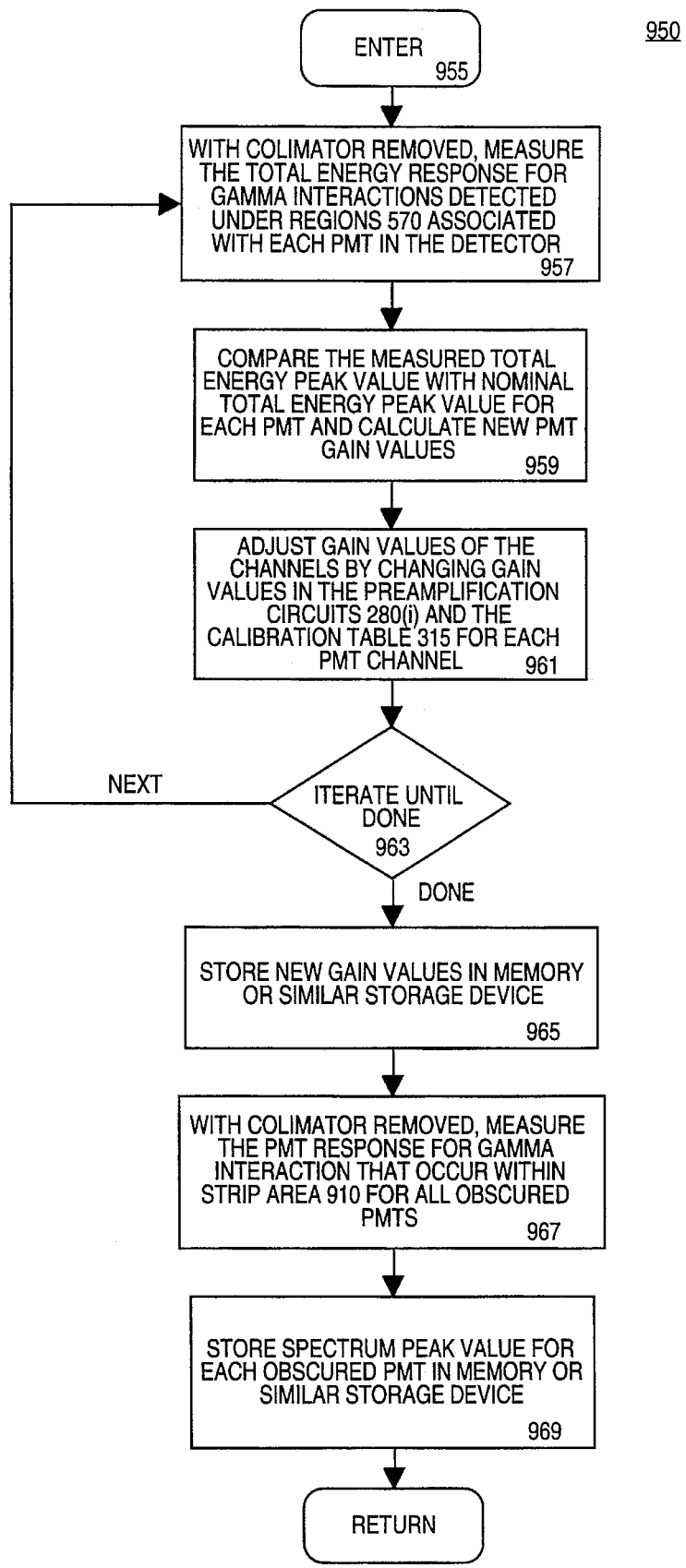
FIG. 13A is a flow chart illustrating initial calibration tasks executed by the autogain procedure of the present invention as typically executed at the factory during calibration or in the field without a collimator for SPECT mode of operation.
Figure 13B:
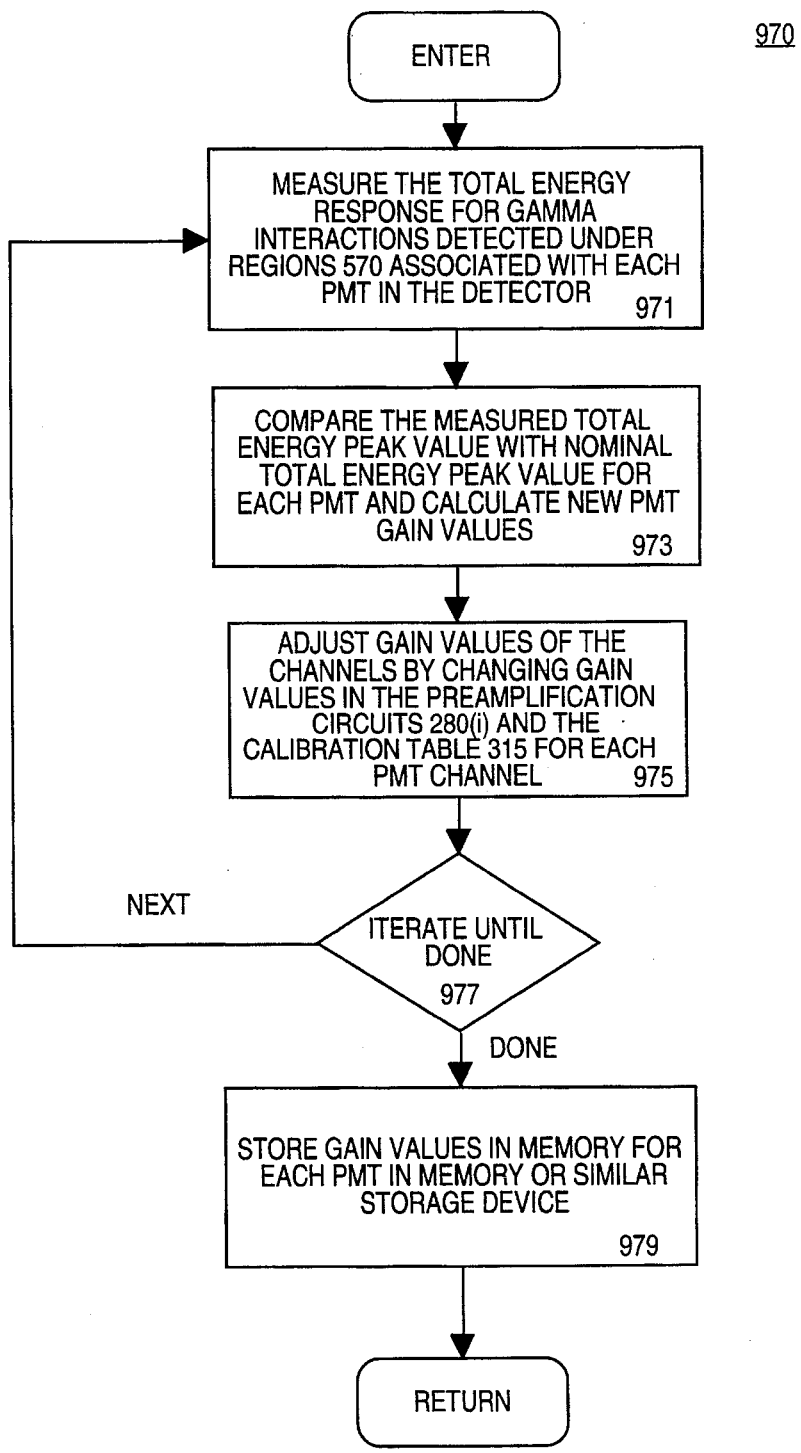
FIG. 13B is a flow chart illustrating routine calibration tasks executed by the autogain procedure of the present invention as typically executed at the site during routine calibration with the collimator removed for SPECT mode of operation.
Figure 13C:
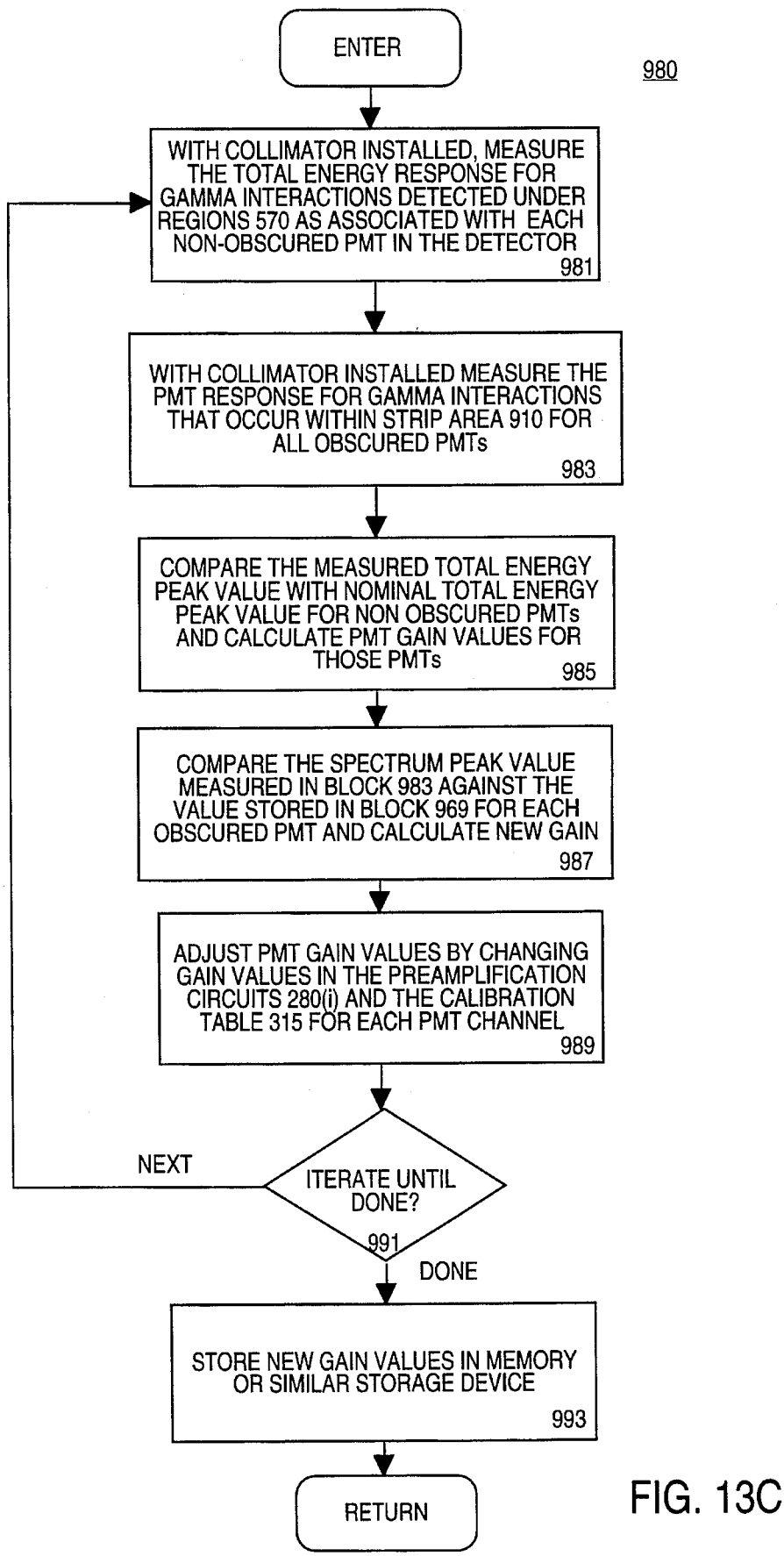
FIG. 13C is a flow chart illustrating routine calibration tasks executed by the autogain procedure of the present invention as typically executed at the site during routine calibration with the collimator installed for SPECT mode of operation.

Refer to FIG. 13A, FIG. 13B, and FIG. 13C which illustrate processing steps executed by the computer system 1112 of the present invention for performing automatic gain calibration/adjustment of the preamplification gains Gp (e.g., associated with circuits 280(i) and the adjustment within the calibration table 315) for each channel of the scintillation detector.

FIG. 13A illustrates the process flow 950 of the present invention that is used to perform initial or original calibration of the scintillation detector and is typically performed prior to the energy, linearity, and uniformity calibration. The energy, linearity, and uniformity calibration can be performed at the manufacturing site or can be performed at the operational site of the camera system. This is done prior to operational imaging of a patient. As shown, at step 957, the collimator is removed (if present) from the scintillation detector and the array of photomultipliers is irradiated with a uniform flood field of known energy gamma radiation (e.g., a known isotope is utilized). For all events that are detected within the regions 570 of FIG. 12 (for each PMT), the total energy of the events are recorded, individually, into memory 1102 and associated with the appropriate PMT such that a distribution is formed for each PMT of only those events that were detected above the PMT. The memory 1102 stores the information in a matrix form that associates a given PMT with a distribution of the total energy of gamma events detected within region 570 for that given PMT. At block 957, a measured peak total energy value of the distribution is determined by the computer system for each PMT.

Since a known isotope is utilized, its total energy is known (e.g., nominal total energy peak). At block 959 for each PMT, the measured total energy peak value, as reported by the scintillation detector at block 957, is compared by the present invention against the known ("nominal") total energy peak value associated with the isotope. Within block 961 of FIG. 13A, the gain of each PMT channel is then adjusted such that the measured total energy peak value matches the known or nominal total energy peak value.

For instance, since the energy detected by the scintillation detector responsive to each gamma event of the flood field is known (e.g., X), the peak energy calculated and associated with all PMTs is compared against the known value (X), and the gain (Gp) of the PMT is adjusted up or down accordingly such that the measured value and the nominal value are equal. It is appreciated that both the gain values associated with the preamplification circuits 280(i) and also associated with the calibration table 315 are adjusted at block 961. The gain values associated with the preamplification circuits are a coarse gain and the gain values of the calibration table 315 are fine adjustment values. At block 961, the gain values are also applied to the preamplification channels and the calibration table 315 for each PMT channel.

Refer to FIG. 12 which illustrates a PMT cluster of PMTs 0, 2, 10, 11, 12, 4, and 3 (center). The total energy of events occurring within region 570 of PMT 3 is recorded and stored over a number of events and a measured peak energy value is determined from the energy distribution (at block 957). For events occurring within region 570 for PMT 3, PMT 3 is inherently the central PMT (of the PMT cluster). Therefore, it is expected that the central PMT detects approximately 45% of the light energy (X) detected by the detector. If the total energy of the detected event (at region 570) is 5% higher than the expected value of X, then the gain Gp of the center PMT 3 is adjusted downward by 10% (at block 961) because approximately 45% of 10% adjustment will equally compensate for the detected 5% deviation. This is performed for each of the 55 PMTs of the PMT array.

However, the above gain (Gp) correction ignores the contribution of the peripheral PMTs. It is true that one or more of the peripheral PMTs (e.g., 0, 2, 10, 11, 12, or 4) may have a deviant gain which, for example, may cause a 5% energy deviation for events detected within 570 of PMT 3. If this is the case, then the above correction to the gain (Gp) of PMT 3 may have been made in error. Therefore, the present invention, at block 963, performs the above gain calibration/adjustment for each of the 55 PMTs a number of different times in an iterative procedure (e.g., 10 to 20 times but the number is programmable) to account for the possibility of inaccurate adjustments. Based on this iterative procedure, the effects of inaccurate gain adjustments become significantly reduced as each PMT is eventually adjusted as a center PMT for each iteration. At the end of the processing of the last iteration, the final preamplification gain (Gp) assigned to each PMT is recorded in memory 1102 (or other storage unit) at step 965. Each gain value is stored associated with its PMT.

Referring to FIG. 13A, block 967 is then entered. The collimator remains removed from the detector and the PMT array is again illuminated with the same flood field radiation. For each "obscured" PMT (e.g., not obscured during block 960, but obscured when the collimator is subsequently installed), a region 910 is defined that extends into the field of view of the detector that will encompass the open region 615 of the collimator (when installed). For each "obscured" PMT, each gamma interaction that occurs within its region 910 is recorded by the computer system 1112 at block 967. The integrated channel output for that "obscured" PMT is then recorded to memory 1102 and an energy distribution is formed wherein the peak energy value is then determined at block 969. In the preferred embodiment, the "obscured" PMT is a peripheral PMT by definition for all gamma events that occur within its associated region 910, therefore, the "obscured" PMT is expected to receive a fraction, C, of the total event energy (wherein C is less than 10 percent). For the example of FIG. 11, this would represent a fraction, C, of the value X (2000 photons of 3 eV each) as reported by the detector. The measured peak integrated channel signal detected at block 960 for the "obscured" PMT should register roughly a fraction of X, or C*X.

For instance, (see FIG. 11) for all events occurring within the region 910 associated with PMT 39, the integrated channel signal output associated with PMT 39 is recorded until a distribution is formed in memory 1102. This is performed for each obscured PMT (with respect to its associated strip area 910) over a number of gamma interactions (e.g., 500, but the number is programmable). The peak PMT signal of the distribution of integrated channel signals for each obscured PMT is then recorded into memory 1102 or other storage unit associated with its PMT. Processing of block 950 then returns.

At the completion of the process 950, the present invention calibrates each PMT tube of the array according to events that occur over each PMT and records this gain value in memory. Process 950 also records the peak integrated channel signal for each obscured PMT in response to events that are detected with the obscured PMT's individual strip region 910.

Refer to FIG. 13B which illustrates the routine calibration process 970 of the automatic gain correction of the present invention when the collimator is removed. Routine calibration 970 can be performed at the operational site for calibration of the scintillation detector while the collimator is removed. The processing of blocks 971–979 are analogous to the processing tasks 957–965 of FIG. 13A. Therefore, at block 979 of FIG. 13B, the corrected gain values are stored in memory 1102 and implemented within the preamplification stages 280(i) and the calibration table 315 for each channel. Since the collimator is removed, there are not any actual obscured PMTs.

Refer to FIG. 13C which illustrates the routine calibration process 980 of the automatic gain correction of the present invention when the collimator is installed. Routine calibration 980 can be performed at the operational site for calibration of the scintillation detector while the collimator installed. At block 981, a uniform flood field source is placed in front of the collimator. Interactions occur over the PMT array and the total energy of events detected over the center region (570) of each central PMT (e.g., non-obscured PMT) are recorded in memory 1102 and associated with that PMT. A distribution is recorded for each central PMT and a measured total energy peak value is determined for each central PMT. Block 981 is analogous to block 957 except the processing for block 981 is applicable only to central PMTs. The presence of the collimator does not interfere with this process because the centrally located PMTs are under the open section 615 of the collimator.

At block 983, for each obscured PMT, the present invention records the integrated channel signals from the obscured PMT only for gamma events that occur within that obscured PMT's associated strip region 910. A separate distribution of integrated channel signals is recorded for each obscured PMT and stored in memory 1102 (or other storage device). As stated above, the strip regions 910 associated with the obscured PMTs are aligned with the central portion of the collimator. The processing of block 983 is analogous to block 967, except at block 983 the collimator remains installed. It is appreciated that blocks 981 and 983, of process 980, can occur coincidentally.

At block 985 of FIG. 13C, the measured total energy peak values of the central (e.g., non-obscured) PMTs as reported from block 981 are compared against the known (nominal) total energy peak values for each central PMT channel. The gain value for each central PMT is then adjusted accordingly. The processing of block 985 is analogous to the processing of block 959 except only central PMTs are processed in block 985. The new computed gain values for the central PMTs are stored in memory 1102 (or similar storage device).

At block 987 the present invention, for each obscured PMT channel, compares the measured spectrum peak value (that was measured within block 983) against the stored peak value associated with that obscured PMT channel (that was stored by block 969). At block 987, the present invention computes a new gain (by increasing or decreasing the current gain) for each obscured PMT such that the measured value matches the stored value for each obscured PMT. This can be performed by a straight ratio computation (e.g., if the measured spectrum peak value reported from block 983 is 10% larger than the stored value from block 969, then the current gain for that obscured PMT is reduced by 10%, etc.). At block 987, the newly computed gain for each obscured PMT is then recorded in memory 1102 (or similar storage device).

At block 989 of FIG. 13C, the present invention then applies the newly computed gains of: (1) the central PMTs as computed in block 985; and (2) the obscured PMTs as computed in block 987, to the appropriate preamplification circuits 280(*i*) and the appropriate locations within the calibration table 315 for each channel. The preamplification circuit contains the coarse gain control while the calibration table 315 provide fine gain control. At block 991, the present invention performs the processing in an iterative manner over a number of times (a programmable number) to refine the calibration and adjustment. When done, processing flows to block 993 where the newly adjusted gain values for each channel (central and obscured) are stored in memory 1102 (or other storage unit).

It is appreciated that processes 970 and 980 can be performed by the camera system at any time. By performing the process 980 before imaging sessions of the gamma camera system, the preamplification gains of the PMT array are calibrated automatically such that the responses of the PMTs remain essentially the same as when they were calibrated at the factory. This will cause the scintillation detector to be calibrated to match the response it had when the energy, linearity, and uniformity correction values were created. This match between the energy, linearity, and uniformity correction factors and the detector response improves image quality.

In an alternative embodiment of the present invention, in lieu of using a peak energy determination of the distributions of processes 959, 969, 973, 985, and 987, an average or mean computation can be utilized. A "representative" data value of an energy or signal distribution can therefore be the peak, average, mean, or similar function, of such distribution.

In another alternative embodiment of the present invention, the integrated channel signals for each obscured PMT are not measured to perform the gain correction for these PMTs. In lieu of the integrated channel signals being recorded, the total energy of the events occurring within the strip regions 910 are recorded and an representative energy value is computed for this distribution for each obscured PMT. The above is performed for both blocks 967 and 983 such that the total energy of each gamma event is recorded and compared.

It is appreciated that the data related to the integrated channel signals that is needed by the above procedure is gained via the computer system 1112 from the DEP 300 from bus 397 (see FIG. 2D). The total energy for a given event is supplied over bus 322 of DEP 300. In each case where channel information is gathered for gamma events detected within specific XY regions, the present invention provides a coincidence circuit for comparing the XY coordinate of the event as output from bus 327 and 332 and the circuit compares this coordinate value against the known region (e.g., area 570 or strip region 910). If a match occurs, then the desired data is sampled either via bus 322 for the total energy signal or via bus 397 for the specific channel data. Alternatively, this specific channel data can also be supplied directly from buffer 325 of the DEP 300.

VARIABLE DYNAMIC COMPRESSION

The present invention DEP 300 circuits (of both detectors 80 and 80') provides a programmable, variable dynamic compression table 355 (FIG. 2D) so that the energy response of a PMT can be adjusted using a programmable digital function stored in memory rather than using dedicated analog hardware, as in the prior art. In effect, the dynamic compression table 355 of the present invention is utilized in place of the well known analog breakpoint driver circuits of the prior art. The breakpoint driver circuits of the prior art are composed of analog circuits (including diode networks) for adjusting the PMT output. However, opposite to the present invention, the prior art circuits are not programmable or readily modifiable.

The dynamic compression table 355 may be composed of programmable memory or static memory (ROM or PROM). If programmable memory is utilized, it may be composed of a number of well known memory types, such as RAM or EEPROM.

Figure 14A:
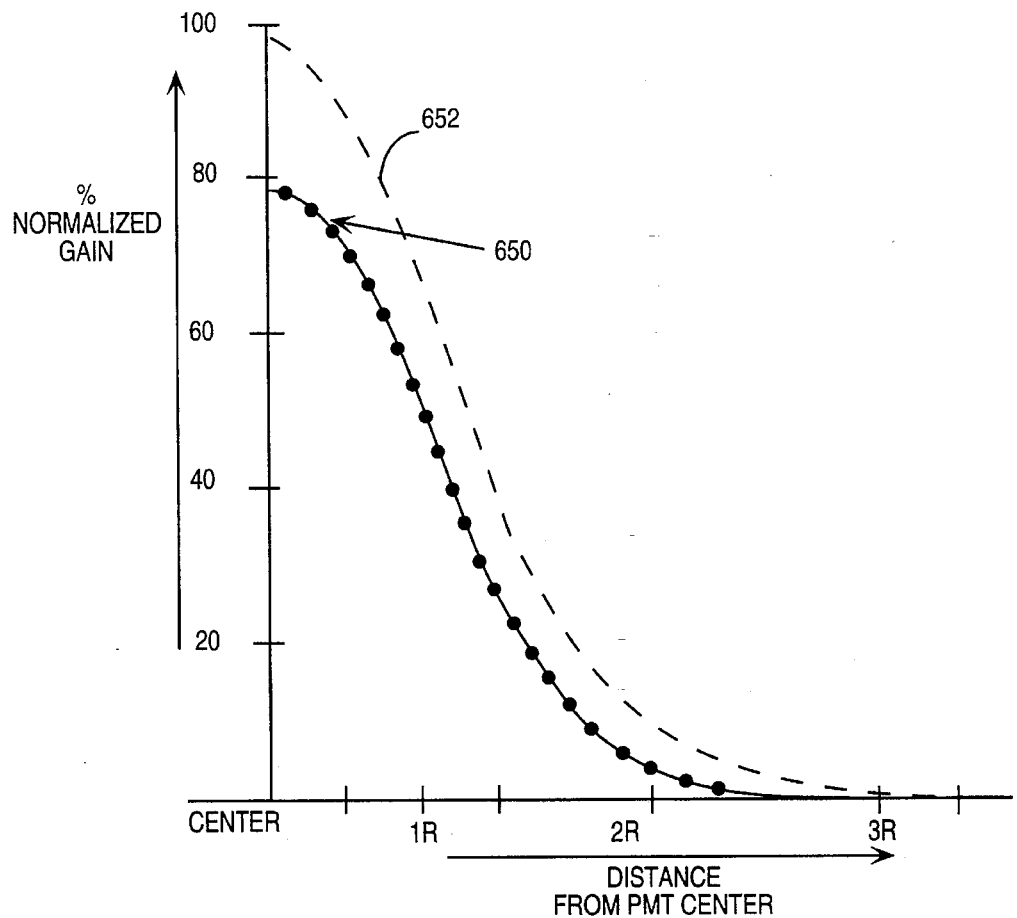
FIG. 14A illustrates an uncompressed response of a PMT for an event verses the distance from the center of the event and also shows compressed response.

The dynamic compression table 355 of the present invention performs two tasks: (1) it reduces or eliminates noisy signals from PMTs far from the point of the gamma interaction; and (2) its shapes the remaining signals in order to obtain a more uniform spatial response across the detector. Digital implementation of this procedure allows the use of relatively simple linear preamplifiers thus reducing the complexity and cost of the analog electronics, and improving the long term stability of the system. The Dynamic compression table 355 is utilized to alter the signal output from each PMT channel to remove nonlinearity so that when the signal summed with other altered signals, the resultant summation signal is more linear. Refer to FIG. 14A which illustrates the normalized energy response of a PMT based on the distance from the PMT center at which a gamma interaction occurs. The response 652 is the signal before correction by the dynamic compression table and response 650 illustrates the corrected or compressed response as output from the compression logic of the DEP 300. Due to the characteristics and physics of the PMT, the response is overly elevated for events that occur near the center of the PMT, therefore the compression logic reduces this response accordingly.

Figure 14B:
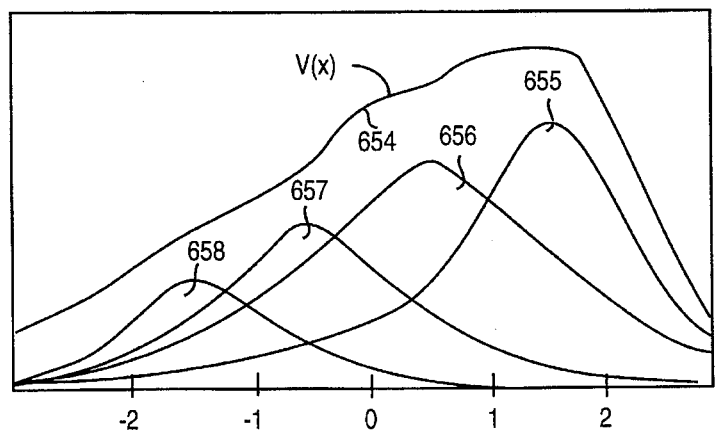
FIG. 14B illustrates a summation of PMT responses (of a PMT cluster) over a one dimensional PMT configuration.

Refer to FIG. 14B. The overly elevated response of the PMT tube near the tube's center poses a problem because when summed with other neighboring PMT's responses, the summation signal is not linear. The accuracy of the centroid computation depends, in part, on the linearity of the summation signal as evidenced from the centroid computations as previously described herein. FIG. 14B is a plot of PMT response over PMT position for 5 PMTs in a particular single axis. Response 654 is the summation of each of the 5 PMT signals. FIG. 14B illustrates that the summation signal 654 (sum of the PMT responses 655–658) can be slightly nonlinear, and this nonlinearity tends to reduce the spatial accuracy of the centroid computation. The dynamic compression table 355 and subtractor circuit 391 provides an adjustment to the input PMT integrated channel signal over bus 352 to allow a more linear summation signal. In affect, after compensation by the dynamic compression table 355, the summation signal 654 has a more linear slope.

Figure 15B:
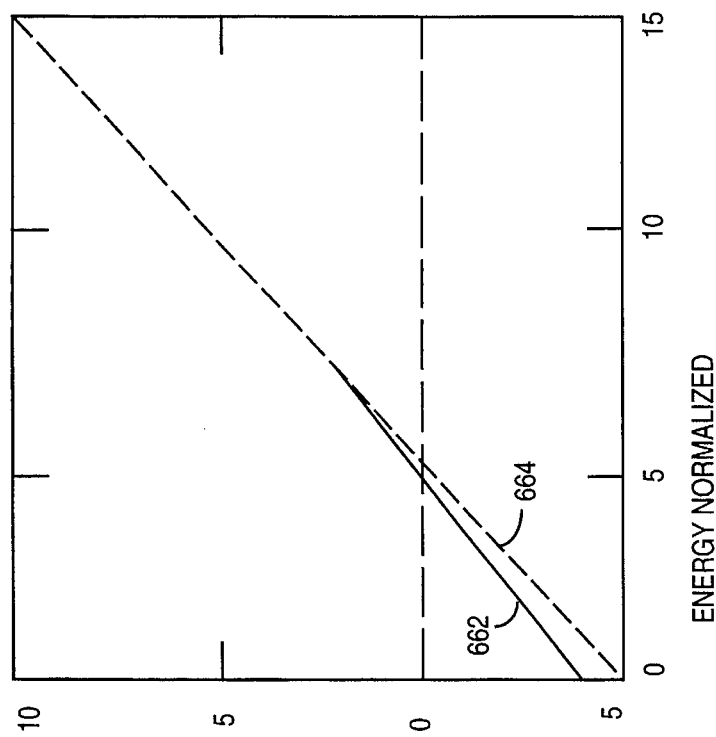
FIG. 15A and FIG. 15B and FIG. 15C illustrate exemplary compression procedures realized by the dynamic compression table and circuitry of the present invention.
Figure 15A:
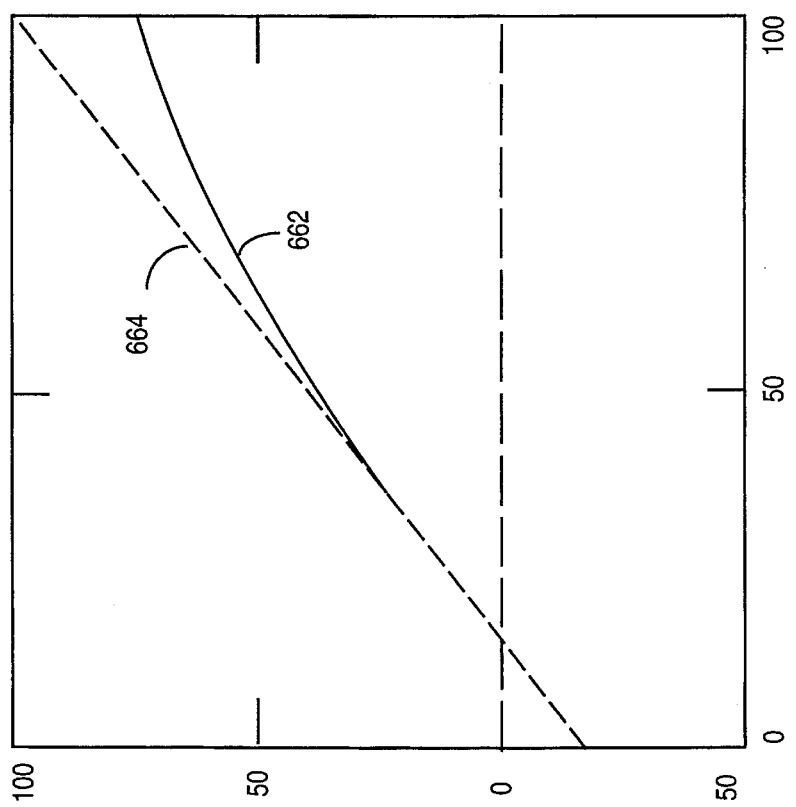

FIG. 15A illustrates a graph of the input energy response (normalized to global energy) 664 of a PMT channel and the desired normalized altered response 662 as a result of the dynamic compression procedure of the present invention. As shown, for moderate energy levels the higher the energy the more the attenuation. Since the dynamic compression procedure operates on normalized values, the dynamic compression table 355 receives, as an input, the global energy over bus 322. The dynamic compression table 355 outputs, over bus 392, the value of the offset or difference between signal 664 and 662 (for a given input signal over bus 352) multiplied by the global energy (GE). Therefore, the output of the energy table 355 of the present invention is not normalized. The subtractor 391 then subtracts this output of table 355 from the uncorrected PMT channel signal supplied over bus 352. The result is a corrected or compressed integrated channel signal over bus 397. FIG. 15B illustrates the response of the conversion utilized by the present invention for normalized input signals less than 15 percent of the max signal value. As shown, the corrected energy curve 662 is slightly higher in value than the input or uncorrected curve 664.

In a particular embodiment, the compression table 355 is 6×8×14 (32 k) in size and is addressed by the 6 MSBs of the global energy signals (322) and the 8 MSBs of the calibrated channel signal (352). Each 2 byte cell contains a 14 bit offset value which is subtracted from the 10 bit value of the channel signal 352. The dynamic compression table 355 is calculated to 14 bits of precision: 8 significant bits plus 6 fractional bits. The finer sampling allows the X and Y weighted sums to take on a greater number of values, reducing the quantization effects of the integer position calculation. The output of the offset value from table 355 is 16 bits and the input to the subtractor from bus 352 are the MSB 12 bits. The output from the compression table 355 of the present invention is at a higher resolution than the signal over line 352.

An exemplary and general compression procedure utilized by an embodiment of the present invention is illustrated as the response shown in FIG. 15A and FIG. 15B. Since the dynamic compression is a non-linear function, the PMT integrated channel signals are scaled by the global energy prior to dynamic compression. The scaling allows the dynamic compression function to be independent of energy, which is an improvement over the non-linear amplifiers of the prior art.

Within this exemplary procedure, the integrated channel signal supplied over line 352 ($E_{pmt}$) is scaled, normalized, by the global energy (GE) relative to the nominal peak global energy (ge) by:

$$E_{in} = E_{pmt} * (ge/GE)$$

The value ge is constant and an exemplary value is supplied below. The scaled signal, $E_{in}$, is passed to the dynamic compression (rolloff) procedure, D, as shown further below.

$$E_{fn} = D(E_{in})$$

Finally, the compressed signal is scaled back, denormalized, to its original level:

$$S = E_{fn} * (GE/ge)$$

where S is the signal that is output over line 387 from the subtractor circuit. The exemplary general roll off procedure of the present invention is shown below as:

$$D(E_{in}) = [SHi * e^{-(SHi*RHi)/SP}\pi + [SLo*[e^{-(SLo*RLo)/SP} - 1]] - bias*SP$$

Where:

$SLo = LoThresh *SP - E_{in}$ (for $E_{in} < LoThresh * SP$)
$SLo = 0$ (for $E_{in} >= LoThresh * SP$)
$SHi = E_{in} - HiTresh *SP$ (for $E_{in} > HiTresh * SP$)
$SHi = 0$ (for $E_{in} <= HiTresh * SP$)

According to the general procedure, SP is the nominal peak calibrated PMT signal and the each of the other parameters is expressed as a fraction of SP. LoThresh is the starting point of the low-end rolloff and HiTresh is the starting point of the high-end rolloff. RLo is the degrees of low-end rolloff. RHi is the degrees of high-end rolloff. Bias is the DC bias to be subtracted from the rolled off function. Preferred results have been achieved with the following parameters (however each is programmable and adjustable within the present invention):

ge=180
SP=200
LoTresh=0.08
HiTresh=0.25
RLo=2.5
RHi=0.35
Bias=0.05

In the computation of the preferred embodiment of the present invention, the compression table 355 contains only the offset value that is subtracted from the channel signal, e.g., the difference between lines 662 and 664 of FIG. 15B. Therefore, the actual value stored in the lookup table 355 is computed based on the difference between the above procedure and the channel input signal, times the global energy GE. This is shown below:

$$\text{Data output over bus } 392 = [E_{in} - E_{fn}] * [GE/ge]$$

The output over bus 392 is then subtracted from the uncorrected energy of the particular PMT channel. Therefore, the procedure below illustrates the corrected or compressed signal:

$$\text{Data output over bus } 387 = E_{pmt} - \text{Data output over bus } 392$$

The dynamic compression circuit 355 of the present invention ensures that the above subtraction does not yield a negative number. Any negative number output is zeroed. The above procedure an be reduced and given below assuming a normalized input signal from the range 0 to 100:

$$E_{fn} = [E_{in} * e^{-(0.35*TH)/100} + TL*(e^{-(2.5*TL)/100} - 1)] - 0.05$$

where:

$E_{in} = E_{pmt}/GE$
TH=$E_{in}$−25, if $E_{in}$<25; and TH=0, if $E_{in}$<=25
TL=8−$E_{in}$, if $E_{in}$<8; and TL=0, if $E_{in}$>=8
0.05=small baseline offset The input to the compression table 355 is GE (over bus 322) and $E_{pmt}$ (over bus 352) for a particular PMT channel. The output of the table 355 is shown below. The actual value stored in the lookup table is computed based on the difference between the above procedure and the normalized input, times the global energy GE. This is shown below:

$$\text{Data output over bus } 392 = [E_{in} - E_{fn}] * GE$$

The output over bus 392 is then subtracted from the uncorrected energy of the particular PMT channel. Therefore, the procedure below illustrates the corrected or compressed signal:

Data output over bus 387=$E_{pmt}$–Data output over bus 392

The dynamic compression circuit 355 of the present invention ensures that the above subtraction does not yield a negative number. Any negative number output is zeroed.

It is appreciated that given sufficient memory size within circuit 355 of the DEP 300, the data can be configured such that the global energy value GE is input, along with the channel data of bus 352 and the compression table 355 can then output the corrected value of the PMT channel data directly over bus 387. In this embodiment, the subtractor 380 is not utilized. Also, the data of the dynamic compression table 355 of the present invention can be further optimized by modifying the procedures illustrated above. These modifications or optimizations may involve empirical data that is particular to a camera system or operating environment.

Figure 15C:
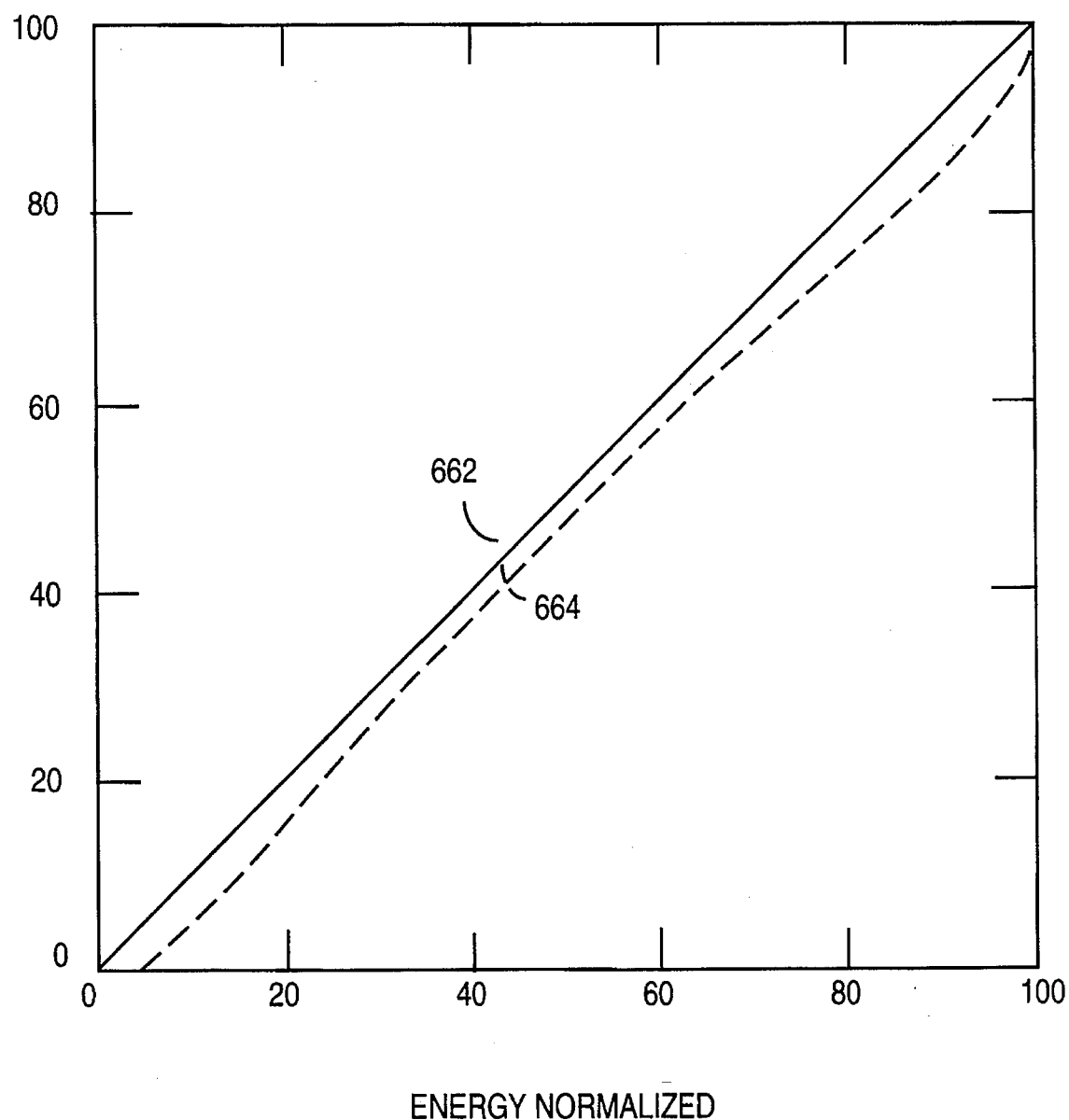

As shown in FIG. 15C, another dynamic compression procedure is illustrated that is stored in the dynamic compression table 355 and used in a similar manner with similar mechanisms as shown and discussed above.

Given the above procedures, the actual data tables (addressed by GE and $E_{pmt}$) may readily be determined by one of ordinary skill in the art and are exemplary only. Because the table 355 is programmable, the level of resolution desired by any one embodiment is variable depending on the available size of memory for circuit 355. According to the present invention, the data of the dynamic compression table 355 is generated by data processor 1112 according to a programmable set of parameters and the compression procedure shown above and this information is then downloaded into the memory 355. If RAM is utilized, then the actual correction data can be stored in a disk storage 1104 or ROM 1103 and then down loaded into the memory 355 before the gamma camera system is used. Therefore, the data processor 1112 may store a variety of different procedures and/or correction data tables and a user can select among them for generating tables of correction data and for loading them into memory 355 for use in the DEP 300 as system calibration. In this alternative, the dynamic compression table 355 is extremely flexible and programmable. Alternatively, when the memory 355 is EEPROM, the data is programmed into the memory 355 before use and can be reprogrammed by a technician.

AUTOMATIC BASELINE COMPENSATION

Figure 16:
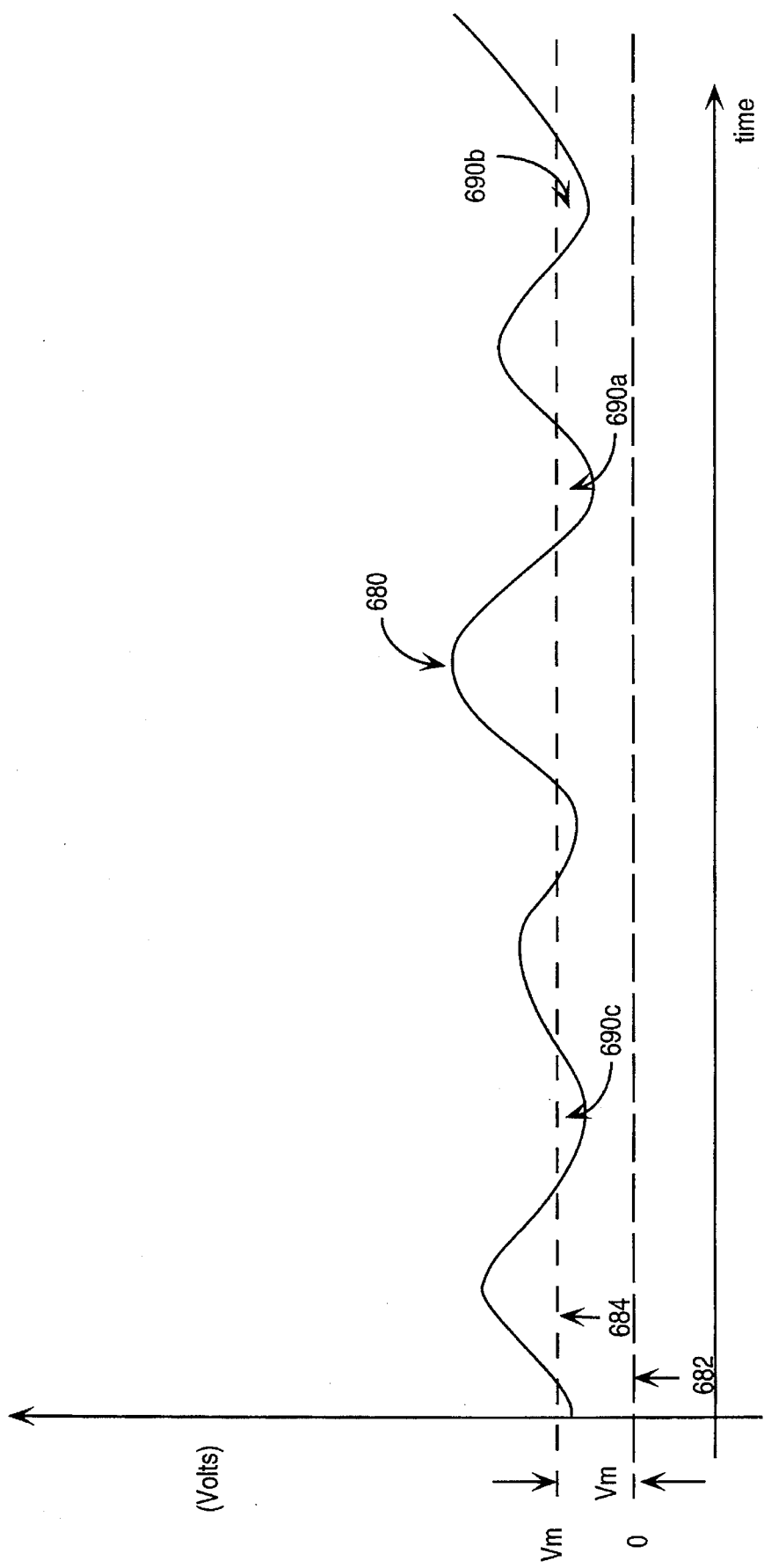
FIG. 16 illustrates an analog voltage wave form (with baseline offset) of a preamplification channel of the present invention.

Within the present invention, a slight DC offset (baseline offset) is maintained within each preamplification stage for each PMT channel via a digital input to a DAC which controls inputs 212 and 214 of FIG. 2C. This is the case for both detector pair 80 and 80'. Shown in FIG. 16 is an exemplary PMT analog channel output voltage signal 680 as sampled by ADC 236 (of FIG. 2C). Due to the integration processes performed for an event, negative voltages of signal 680 are unwanted, become clipped, and lead to inaccurate integration results. Due to circuit drift of the amplifiers of circuits 280(0) to 280(54) (e.g., due to temperature, current flow, etc.) the baseline of the voltage signal 680 as sampled by the ADC 236 may vary and, if left uncorrected, may dip below zero. The baseline shift of an individual PMT is typically a fraction of a channel signal, but the sum of the shifts over an entire detector can move the global energy peak by several channels. Baseline shifts also result in image registration variations. Drift may be compensated for by the use of expensive amplifier circuits, but since a separate set of amplifiers is required for each channel, such a solution is not economically practical. The present invention provides an automatic procedure and circuitry for baseline compensation in order to adjust for this variable drift by measuring and adjusting the baseline voltage in real-time.

In effect, the present invention inserts (via inputs 212 and 214) a base line compensation voltage amount called Vm in order to adjust the analog signal per channel. This is applicable for detector pair 80 and 80'. Each channel has an independent Vm. This is shown in FIG. 16. Line 682 shows true zero voltage and the signal 680 is adjusted by an amount Vm. After digitization and integration, this offset value Vm must be subtracted from the total, resulting in the net channel signal. Baseline subtraction is performed in the calibration lookup table circuit 315 of the DEP 300 for each channel, and is based on the particular Vm inserted for that channel.

The amount of voltage offset applied at 212 and 214 provided by the present invention varies, as discussed below. However, there is an ideal number Vm, that is computed based on the level of expected noise within the dynamic range of the ADC 236. Since this dynamic range is within 1024 units, in one embodiment, and since the expected noise percentage is roughly 8 percent, the digital value of Vm is approximately 78 units within the dynamic range of the ADC 236. Of course this value will vary depending on the specific implementation of hardware utilized. This value is initially used as an offset to control inputs 212 and 214 (a separate input is used for each channel) to offset signal 680. The value of Vm is determined such that signal 680 does not vary below zero. Vm is also adjusted such that a large portion of the dynamic range of the ADC 236 is not consumed by the offset voltage.

The actual value of the voltage offset as measured by the ADC 236 (when no event is present) may drift. In the present invention, the digital processor 1112 measures the signal output value for a particular channel that is not substantially receiving energy from a gamma event. This value should be near the ideal voltage Vm. The sampled voltage is compared against the ideal voltage and is modified up or down (in a real-time feedback arrangement) to closely match the ideal voltage Vm. In this manner, the present invention compensates for the drift associated with the electronics of the preamplification stage for each channel by modifying the value of the offset voltage. This sample and adjust procedure is performed separately for each channel.

The present invention procedure for monitoring the analog signal of each channel and for modifying the baseline of this signal based on the ideal baseline value of Vm is described below. Generally, the present invention provides two alternate methods for baseline compensation: (1) a method used during periods of low count rate; and (2) a method used during periods of high count rate. The computer system 1112 contains a baseline offset matrix of data values in memory 1102, one for each channel, that records the current baseline offset voltage applied at inputs 212 and 214. The values within this baseline offset matrix are updated by the present invention to compensate for voltage drift of the amplifier stages of the circuits 280(0) to 280(54). Although described with respect to one detector, it is appreciated that the below procedure operates with respect to both detectors 80 and 80'.

Figure 17A:
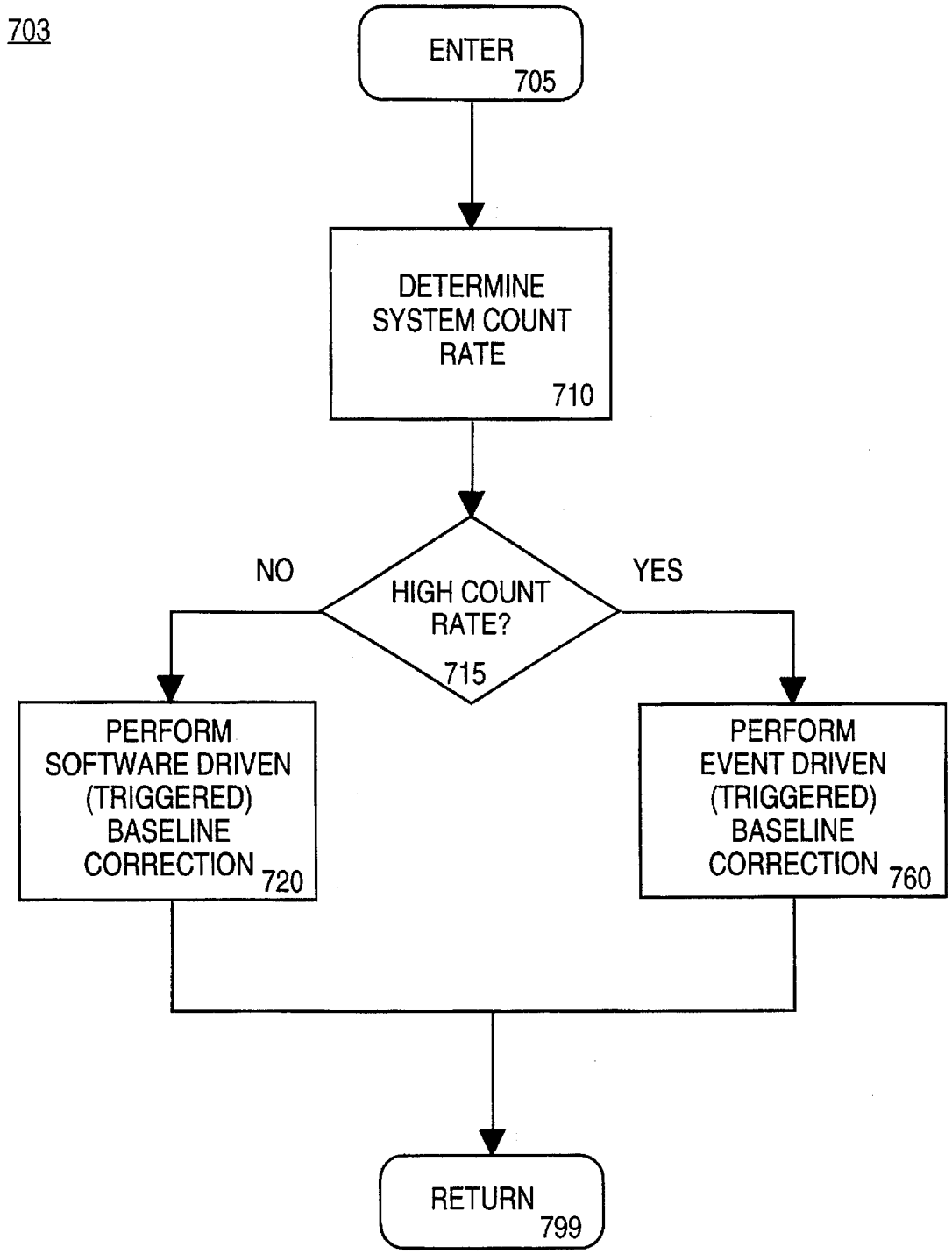
FIG. 17A illustrates a flow chart of the automatic baseline offset calibration of the present invention.

Refer to FIG. 17A which illustrates the channel baseline compensation procedure 703 utilized by the present invention and performed by digital processor 1112. Procedure 703 is performed both respect to both detectors 80 and 80'. At block 710, the present invention initially determines if the count rate detected by the camera system is high or low. High count rate is determined as a count rate that exceeds 75,000 counts per second, but this count rate is exemplary and is programmable within the present invention. Different procedures will be implemented by the present invention depending on the camera's count rate. At 715, the digital processor determines if the count rate is above the threshold (e.g., 75,000 counts/sec) and, if true, block 760 is performed for event triggered baseline correction. If the overall count rate detected by the gamma detector is lower than or equal to the threshold amount, then at block 720, the processor 1112 performs software triggered baseline correction. At the completion of a correction procedure, the processing is exited via 799. It is appreciated that the flow 703 of the present invention is repeated throughout the operational duty cycle of the gamma camera including periods in which the camera is idle and also during periods in which the camera is actively engaged in an imaging session.

Figure 17B:
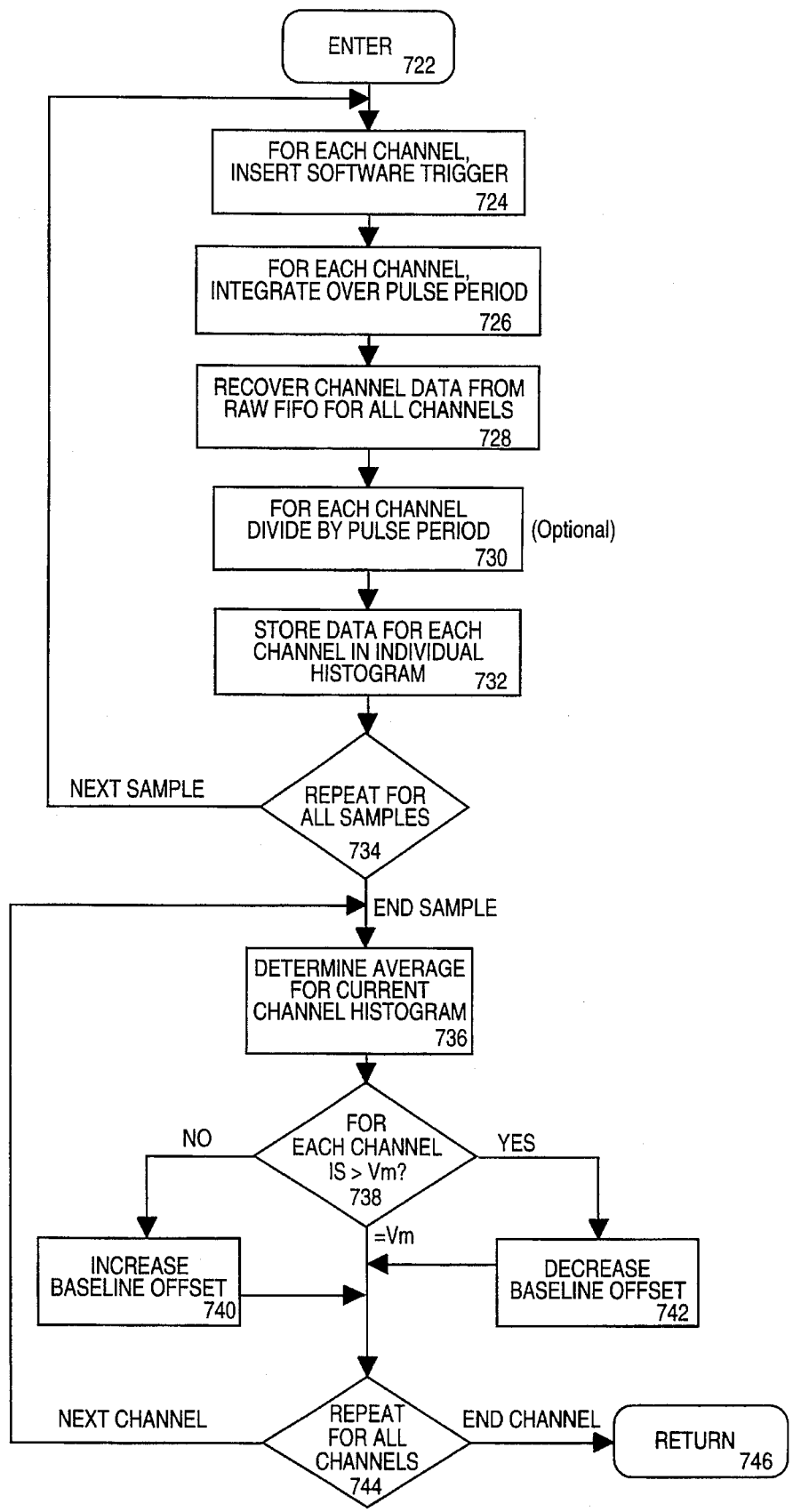
FIG. 17B illustrates a flow chart of the software triggered baseline offset correction procedure of the present invention.

Software Triggered. Refer to FIG. 17B which illustrates the software triggered baseline correction procedure that is performed during periods of low count rate. FIG. 17B illustrates the steps performed by the present invention by block 720. At block 724, for each of the channels of the detector 80, the present invention inserts a software generated trigger that emulates an actual event trigger that would be detected over line 130 of circuit 100 of FIG. 2A. For each channel (of both detectors), the digital processor 1112 in effect triggers an integrator (e.g., 238 or 240) to begin integrating over a pulse period. The integration is performed simultaneously for each channel at block 726 (or alternatively in stages) and each channel should, ideally, integrate over the baseline voltage since statistically no event is expected to coincide with the software triggered pulse period. The software trigger is also called a false trigger since it is not initiated based on detection of a true gamma interaction. Since the software triggered integration does not usually coincide with an event, for the most part, the integration performed by the channels will be over a pulse period wherein the baseline voltage should, ideally, be very close to Vm. This is the case because the channel should not be generating an output signal due to the expected (e.g., statistically) absence of an event.

At block 728, the data generated from the integration of block 726 is recovered from the raw FIFO memory 310 (of DEP 300) by computer system 1112. This memory contains the integrated result of each channel without subtraction of the Vm offset (which is performed by the calibration table 315). Optionally, at block 730, the data for each channel is divided by the pulse period to normalize the integration in time. This step is optional because if the time period of each integration is known, then this time period multiplied by the ideal Vm value can be used as a reference by which the base line offset value can be compensated. Either implementation is within the present invention. At block 732, the data for each channel is stored into a separate histogram that is maintained by computer system 1112 in memory 1102 for each channel. The histogram records the sampled baseline voltage (for a given channel) over the number of samples taken. At block 734, the above process is repeated for a next sample until a predetermined and programmable number of samples is taken. For each sample, the data associated with each histograms are increased. An exemplary number of samples used by the present invention is 250 samples per channel. Therefore, a particular histogram constructed for each channel by block 732 is composed of roughly 250 data points. These histograms are maintained by the present invention in RAM memory 1102 of the data processor 1112. Assuming 55 channels per detector, there needs to be 13,750 false counts per calibration process of the present invention for process flow 720.

At block 736 of FIG. 17B, the present invention utilizes the histogram created for a particular channel of a given detector to determine the average value of the sampled baseline offset amount. This determination may be made using a number of well known averaging, mean or weighted averaging procedures. Any number of different procedures may be utilized consistent within the scope of the present invention at block 736. At block 738, for the particular channel, the average is compared against Vm (which is stored in memory by processor 1112 and is constant for each channel). If the average for the particular channel is greater than Vm, then at block 742 the baseline offset of the particular channel which is stored in a baseline offset matrix within memory 1102 (as applied via signals 212 and 214) is decreased by one unit and the matrix is updated and block 744 is entered. If the average for the particular channel is less than Vm, then at block 740, the baseline offset of the particular channel (as applied via signals 212 and 214) is increased by one unit and the baseline offset matrix is updated and block 744 is entered. Otherwise, if the average value of the baseline is equal to Vm, then no baseline correction is required and block 744 is entered directly. It is appreciated that there is a separate computer controlled pair of inputs, 212 and 214, for each preamplification circuit 280(0) to 280(54).

At block 744, the above procedure (to block 736) is repeated for each channel, so that the baseline corrections for each channel are adjusted (in a feedback arrangement) separately. At block 746 the procedure is exited and the histograms maintained in memory 1102 for the above compensation procedure are reset. Therefore, as can be seen above, the present invention measures the channel voltage for each channel during periods of no expected events and records and adjusts the baseline voltage for the channels. Due to drift, these voltages may vary, but should be constricted to the value Vm to prevent clipping (due to negative voltage). The present invention provides a measurement and compensation procedure to effectively maintain the baseline voltages for each channel to the ideal value, Vm. This is performed using a feedback arrangement as shown in FIG. 17B thus avoiding the use of expensive circuitry within the preamplification stages 280(0) to 280(54).

It is appreciated that the present invention, for block 720, does not determine in advance if there is a real event occurring in coincidence with the software trigger generated at block 724. Statistically, it is rare (but possible) to have an event occur in coincidence with (and therefore interfere with) the software triggered integration period during periods of low count rate. Should an event occur during block 726 of the present invention, that data point will be much larger than the expected value (due to the PMT responses) and will be effectively excluded statistically from the average (or median) computed for the channel at block 736. In an alternative embodiment, the present invention may perform an additional step of excluding all data points from the histograms generated in block 732 that exceed a predetermined threshold in order to exclude data points corrupted by an event. However, given 250 samples (for instance), the number of data points corrupted by an event is very low and is negligible.

Figure 17C:
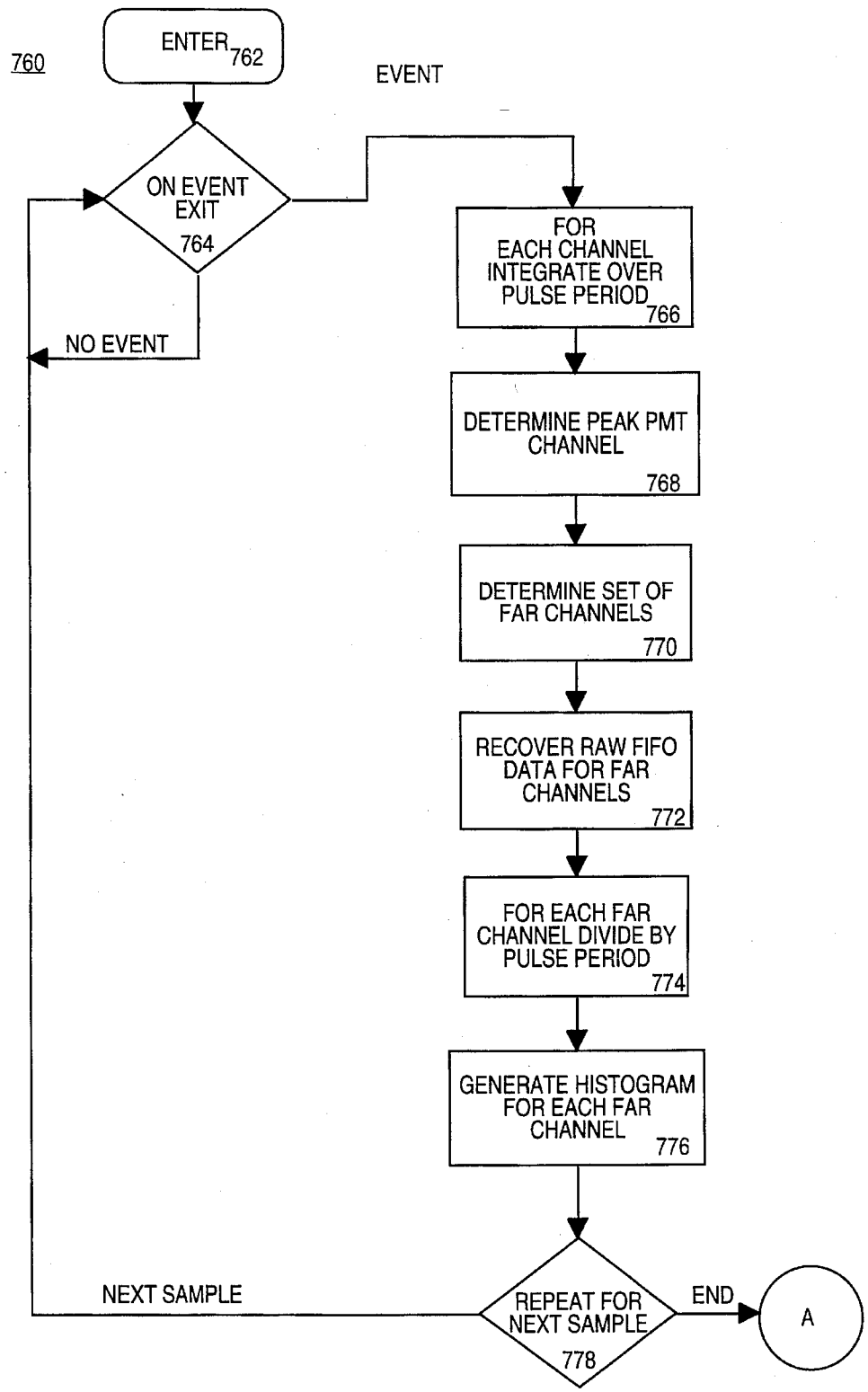
FIG. 17C and FIG. 17D illustrate flow charts of the scintillation triggered baseline offset correction procedure of the present invention.
Figure 17D:
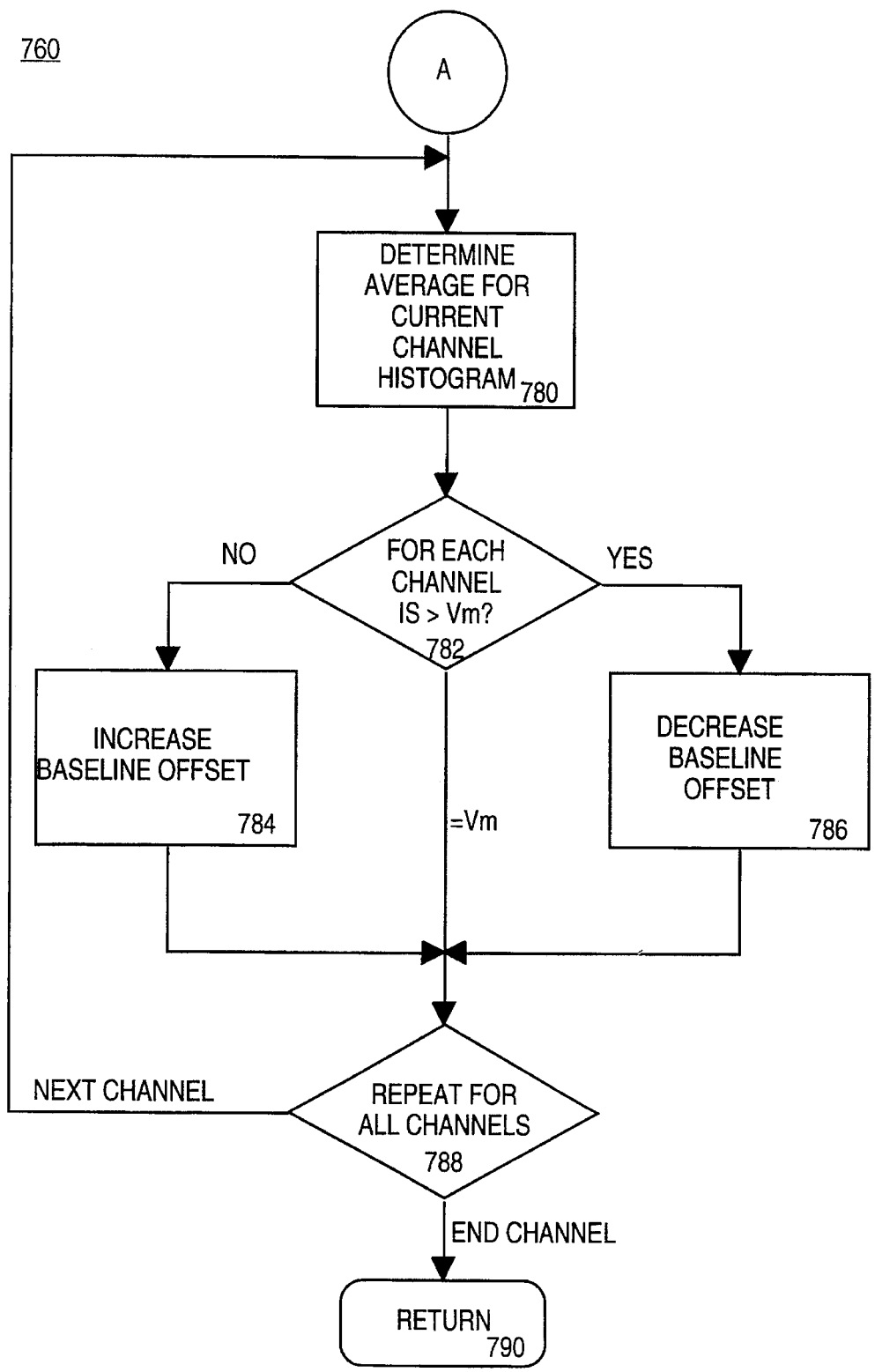

Scintillation Triggered. Refer to FIG. 17C and FIG. 17D which illustrate the procedure 760 utilized by the present invention to provide baseline compensation during periods of high count rates. Procedure 760 utilizes actual events to trigger the measurement processes and therefore is called event or scintillation driven baseline correction. The process begins at the detection of a gamma event at 764 and flows to 766. An event is detected via a trigger signal over line 130. For each channel, the trigger pulse causes each integrator to integrate over the pulse period as described previously herein. Also at block 766, the data from the integration is forwarded to the DEP 300. At block 768, the DEP 300 determines which channel was the peak channel (e.g., the peak PMT) for the event by using circuit 320 (FIG. 2D) described above.

Figure 18:
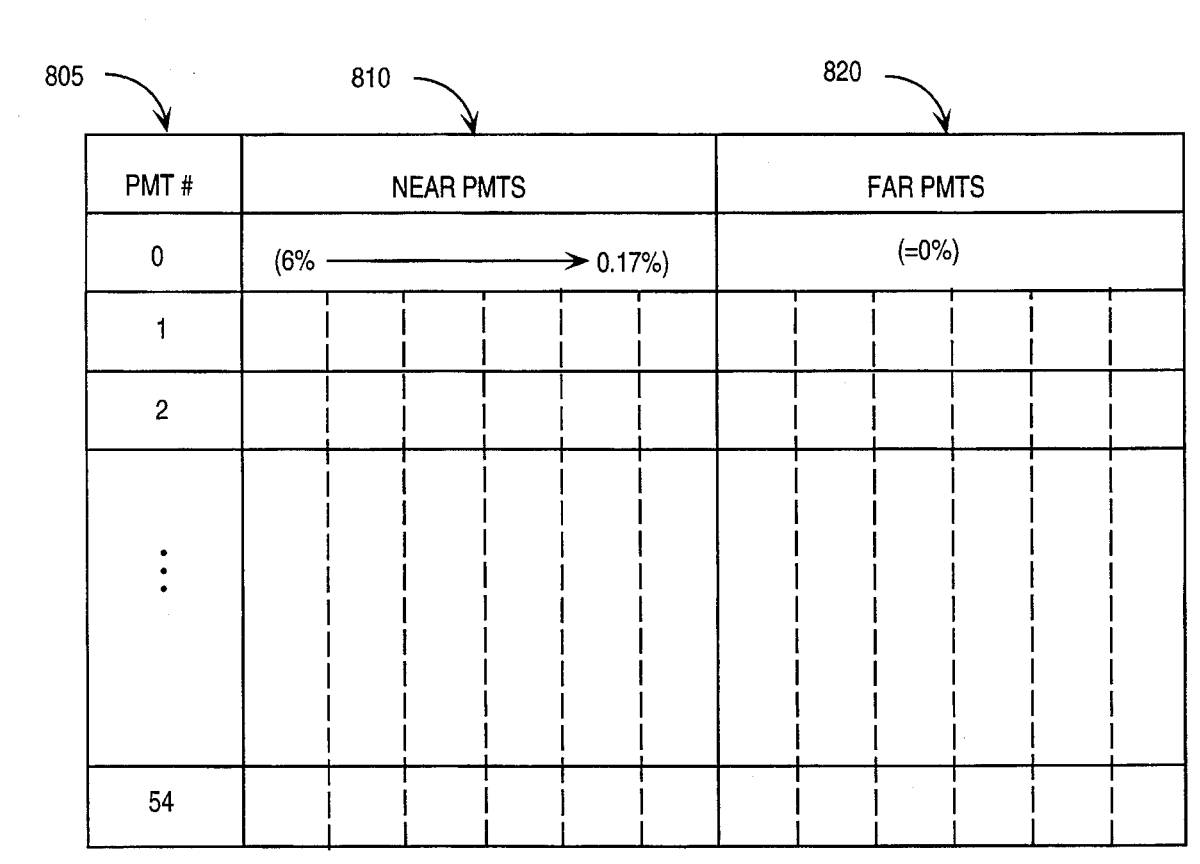

Based on the peak PMT value (which is reported back to the digital processor 1112), the present invention utilizes a memory circuit 800, as shown in FIG. 18, to determine which PMTs are spatially near to the peak PMT and which PMTs are spatially far from the peak PMT. Far PMTs are determined to be those PMTs that receive substantially no (or negligibly little) energy from the event and near PMTs are those PMTs that receive some energy (e.g., less than 0.17%, etc.) from the event. As shown in FIG. 18, there is an entry for each PMT in column 805 and column 810 lists those PMTs that are near and column 820 contains a list of those PMTs that are far. For each peak PMT there is a group of far PMTs that should receive substantially no energy from the event. For any given event detected at block 764 it is the far PMTs that are sampled by the present invention for baseline correction. The set of far PMTs for a given peak PMT address may be determined experimentally by measuring PMT responses for a known peak PMT address within a given PMT array.

At block 770 of FIG. 17C, the present invention addresses circuit 800 with the peak PMT address (number) to determine the set of far PMTs as reported by column 820. At block 772, for the given event the present invention directs computer system 1112 to recover the data associated with each of the far channels as stored in the RAW FIFO memory 310 of DEP 300. These far channels should report essentially an integration of the baseline voltage because they received an insubstantial amount of energy from the detected event. Optionally, at block 774 the integration data of the circuit 310 is divided by the pulse period to normalize the data in time for each far channel. At block 776, the present invention adds the value of the sampled voltage to the histogram for each far PMT channel sampled. At block 778, the above procedure is repeated for the next sample. This procedure continues until each channel obtains at least a predetermined and programmable number of data points in its histogram. An exemplary number of data points is 250 samples per channel.

It is appreciated that for each gamma event at 764, a different number and group of far channels will be sampled. Therefore, the number of histograms updated for each event will vary. The present invention therefore maintains a record of the channel having the least number of data points in its histogram and when this channel reaches the predetermined number (e.g., 250), block 778 will exit to "A" as shown.

Refer to FIG. 17D illustrating the remainder of process 760 of the present invention. From "A," the flow continues to block 780 where the present invention determines the average (e.g., weighted average, median, mean, etc.) baseline voltage for each histogram for all the channels. This process is analogous to the process of block 736 of the software triggered procedure 720 except each histogram of block 780 may contain a different number of data points depending on the spatial distribution of the detected gamma events. At block 782, the present invention determines for a particular channel if its average baseline voltage amount is larger than Vm. If so, then at block 786 the offset voltage stored in the baseline voltage matrix (and as asserted by signals 212 and 214) is decreased for that channel and block 788 is entered. If the average voltage is less than Vm for a particular channel, then at block 784 the baseline voltage as stored in the baseline voltage matrix is increased for that channel and block 788 is entered. If the average baseline offset voltage for the channel is equal to Vm, then no correction is required and block 788 is entered directly.

At block 788, the present invention repeats from block 780 for the next channel until all baseline voltages of channels of the detector head are compensated. At block 790, the process 760 exists. It is appreciated that in the event that two gamma events are detected within a small window of time, one event may trigger the calibration sample (e.g., block 764) and the other event may interfere with the integration of the far PMTs and therefore increase or interfere with the sample data. In these statistically rare cases, as with the software triggered procedure, these corrupted data points are effectively excluded (or minimized) statistically via the averaging functions of the present invention.

Therefore, as shown above, this embodiment of the present invention provides a mechanism and process that maintains the baseline offset voltage, per channel, to the ideal value Vm. Drift associated with the transistors of the preamplification stage of each channel is detected and corrected by using a feedback arrangement. By using the approach of the present invention, the preamplification stages of the detector circuitry may be implemented using less expensive (e.g., less drift tolerant) circuitry.

It is appreciated that during periods of high count rate, the software triggered sampling procedure 720 of the present invention becomes less accurate as more events occur during the calibration samples. Therefore, the event driven procedure 760 is more accurate for high count rates. At low count rates, the event driven calibration procedure 760 is not operational because the count rate becomes too low, e.g., background radiation on the order of 40 counts per second is too low to perform event driven calibration. Procedure 760 requires that each channel be exposed to at least 250 counts per baseline adjustment. Therefore, the use of both software driven 720 and event driven 760 baseline compensation of the present invention is advantageous for high and low count environments.

SWITCHABLE PET AND SPECT MODES OF OPERATION

Figure 19:
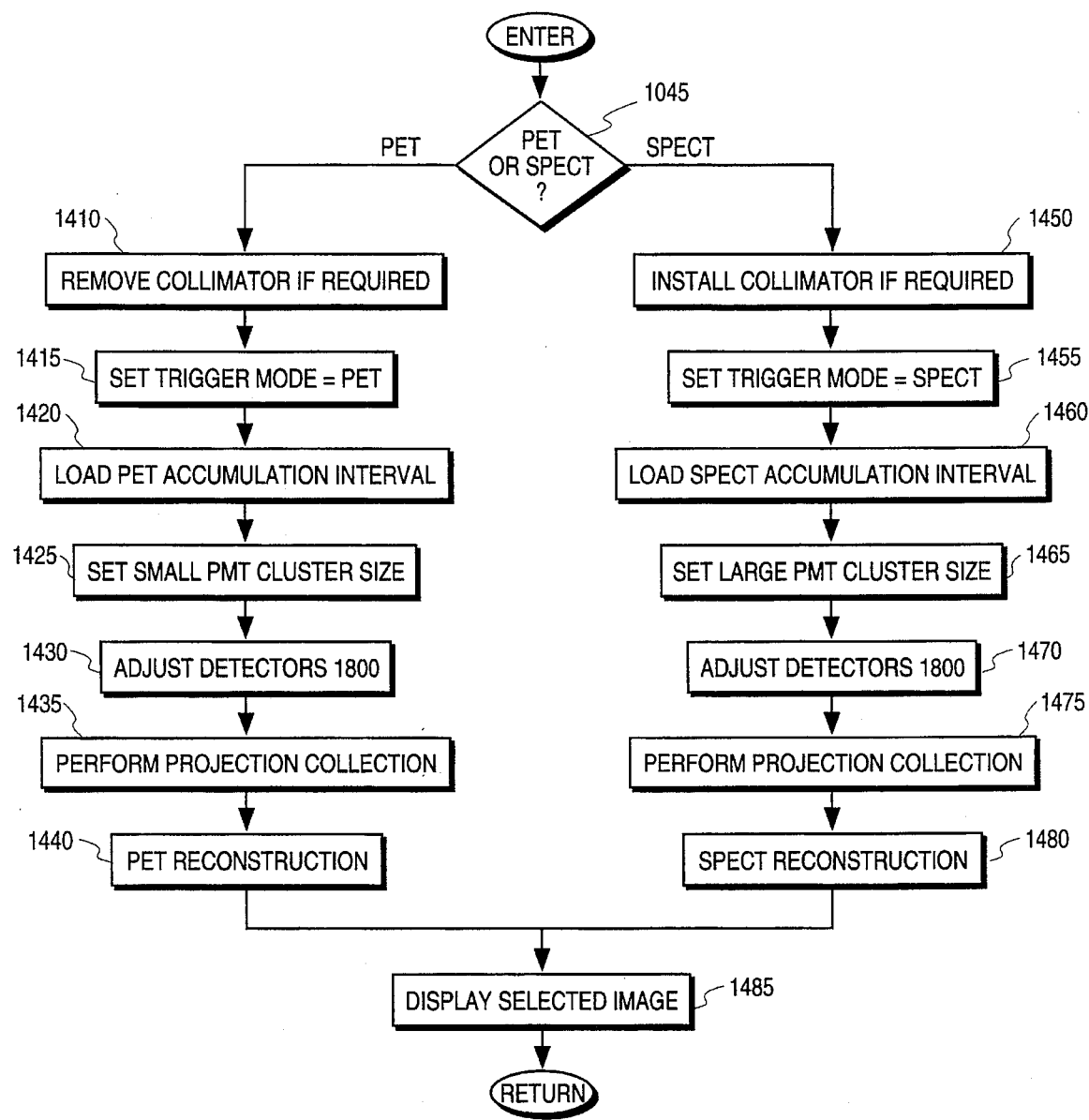
FIG. 19 is an illustration of a procedure utilized by the present invention for switching between SPECT and PET imaging modes of operation for medical imaging.

FIG. 19 illustrates a process 1400 utilized by the present invention when switching between SPECT and PET imaging modes of operation. When operating within PET imaging modes, the patient is injected with a Flouro Deoxi Glucose (FDG) or similar radiopharmaceutical prior to imaging emitting two 511 keV gamma rays. In SPECT mode, the patient is injected with a TI-201 radiopharmaceutical prior to imaging emitting a 140 keV gamma ray. Process 1400 of the camera system of the present invention starts at block 1405 wherein the system checks the user interface device (e.g., 1106 of FIG. 5) or memory 1102 to determine if a PET or SPECT imaging mode of operation is requested. If PET mode of operation is requested, then at block 1410, the camera system verifies to determine if the collimators are removed from the detectors 80 and 80'. Processing is suspended until the collimators are removed and an indication is displayed on unit 1105 or 1065 to indicate the presence of the collimators. If the collimators are removed, then the process continues to block 1415 wherein the camera system programs the trigger mode (e.g., line 1252 of the CTC 1050 of FIG. 2A3) to be in PET imaging mode. This will require coincidence trigger detection to generate a valid event trigger over lines 1240 and 1242.

At block 1420, the computer system loads the PET integration (accumulation) interval (e.g., approximately 320 ns) over line 235 of FIG. 2C into register 1330 for both detectors 80 and 80'. At block 1425, the present invention directs the computer system to set or download a PMT cluster table having a smaller PMT cluster size (e.g., 7 PMTS) into the PMT address table 335 of FIG. 2D for each indexed peak PMT. This is accomplished by programming the PMT address table (see FIG. 8) so that the cluster sizes are smaller for each peak PMT. At block 1430, the present invention adjusts the configuration of the detectors 80 and 80' such that they are at a 180 degree configuration for imaging. At block 1435, the present invention performs a PET imaging session across a number of projection angles with the detectors 80 and 80' in their 180 degree configuration. For each projection angle, within block 1435, data is collected by the present invention on an event by event basis according to the flow diagrams shown on FIG. 4A and FIG. 4B. Within PET mode, coincidence detection is performed between detectors 80 and 80' for the events. Collected data is recorded into the acquisition computer system 1055 (FIG. 1). It is appreciated that in PET mode, the energy value, Z, output by the detectors in response to an event is the sum of the energy detected by the cluster used to localize the event and not the sum of all the PMTS in the detector as is sometimes used in SPECT imaging. The collected data is then imaged by image processor 1060 and PET reconstruction is performed on the projection data at block 1440. PET reconstruction procedures on projection data are well known and are not discussed in detail herein. It is appreciated that at block 1440, attenuation correction maps can be applied to the emission data to correct for nonuniform attenuation. Such functionality is described in co-pending application Ser. No. 08/488,871, filed on Jun. 9, 1995, entitled Multi-Head Nuclear Medicine Camera for Dual SPECT and PET Imaging with Nonuniform Attenuation Correction, and assigned to the assignee of the present invention.

At block 1485, a user-selected image from the PET reconstruction can be displayed on display screen 1065 or display 1105. Since PET imaging data is collected without a collimator, the resolution of PET images is generally of higher quality over SPECT images. It is appreciated that the processing of blocks 1410–1430 can occur in any order and the order presented is exemplary only.

With respect to FIG. 19, if SPECT mode of operation is requested at block 1405, then at block 1450, the camera system verifies to determine if the collimators are present on the detectors 80 and 80'. Processing is suspended until the collimators are installed and an indication is displayed on unit 1105 or 1065 to indicate the absence of the collimators. If the collimators are installed, then the process continues to block 1455 wherein the camera system programs the trigger mode (e.g., line 1252 of the CTC 1050 of FIG. 2A3) to be in SPECT imaging mode which does not require coincidence detection for valid event trigger generation.

At block 1460, the computer system loads the SPECT integration (accumulation) interval (e.g., approximately 840 ns) over line 235 of FIG. 2C into register 1330 for both detectors 80 and 80'. At block 1465, the present invention directs the computer system to set a relatively larger PMT cluster size (e.g., larger than 7, for instance, 19 PMTS) into the PMT address table 335 of FIG. 2D for each indexed peak PMT. This is accomplished by programming the PMT address table (see FIG. 8) so that the cluster sizes are relatively larger for each peak PMT. At block 1470, the present invention adjusts the configuration of the detectors 80 and 80' such that they are at a 180 degree configuration for imaging. At block 1475, the present invention performs a SPECT imaging session across a number of projection angles with the detectors 80 and 80' in their 180 degree configuration. For each projection angle, within block 1475, data is collected by the present invention on an event by event basis according to the flow diagrams shown on FIG. 4A and FIG. 4B. Within SPECT mode, coincidence detection is not performed. Collected data is recorded into the acquisition computer system 1055 (FIG. 1). The collected data is then imaged by image processor 1060 and SPECT reconstruction is performed on the projection data at block 1480. SPECT reconstruction procedures on projection data are well known and are not discussed in detail herein. It is appreciated that at block 1480, attenuation correction maps can be applied to the emission data to correct for nonuniform attenuation. Such functionality is described in co-pending application Ser. No. 08/488,871, filed on Jun. 9, 1995, entitled Multi-Head Nuclear Medicine Camera for Dual SPECT and PET Imaging with Nonuniform Attenuation Correction, and assigned to the assignee of the present invention.

At block 1485 a user-selected image from the SPECT reconstruction can be displayed on display screen 1065 or display 1105. It is appreciated that the processing of blocks 1450–1470 can occur in any order and the order presented is exemplary only. Using the procedure 1400, the present invention offers a nuclear camera system automatically switchable and optimized between SPECT and PET imaging capabilities.

The preferred embodiment of the present invention, a dual head nuclear camera system automatically switchable between SPECT and PET modes of operation is thus described. While the present invention has been described in particular embodiments, it should be appreciated that the present invention should not be construed as limited by such embodiments, but rather construed according to the below claims.

What is claimed is:

1. A nuclear camera system comprising:
   a first detector and a second detector for detecting scintillation events, said first detector and said second detector coupled to an acquisition computer system;
   a input mechanism for selecting between a PET imaging mode and a SPECT imaging mode;
   a switchable trigger detection unit that is automatically switchable between coincidence detection when said PET imaging mode is selected and non-coincidence detection when said SPECT imaging mode is selected;
   said switchable trigger detection unit coupled to supply a first valid event trigger signal to said first detector causing said first detector to record a scintillation event and coupled to supply a second valid event trigger signal to said second detector causing said second detector to record a scintillation event.

2. A nuclear camera system as described in claim 1 wherein:
   said first detector and said second detector individually comprise event detection units for transmitting indications of scintillation events to said switchable trigger detection unit; and wherein said switchable trigger detection unit generates said first and second valid event trigger signals upon detection of two indications of scintillation events occurring within a coincidence window, one in said first detector and one said second detector, provided said PET imaging mode is selected.

3. A nuclear camera system as described in claim 2 wherein each event detection unit of said event detection units correspond to a zonal area of said first or second detector and each event detection unit generates an indication of scintillation events occurring within a corresponding zonal area of said first or second detector.

4. A nuclear camera system as described in claim 3 wherein said event detection units utilize constant fraction discriminators to generate said indications of scintillation events.

5. A nuclear camera system as described in claim 1 wherein:
said first detector and said second detector individually comprise event detection units for transmitting indications of scintillation events to said switchable trigger detection unit; and wherein
said switchable trigger detection unit generates said first valid event trigger signal upon receiving an indication of a scintillation event occurring within said first detector and generates said second valid event trigger signal upon receiving an indication of a scintillation event occurring within said second detector, provided said SPECT imaging mode is selected.

6. A nuclear camera system as described in claim 5 wherein each event detection unit of said event detection units correspond to a zonal area of said first or second detector and each event detection unit generates an indication of scintillation events occurring within a corresponding zonal area of said first or second detector.

7. A nuclear camera system as described in claim 6 wherein said event detection units utilize leading edge discriminators to generate said indications of scintillation events.

8. A nuclear camera system as described in claim 1 wherein:
said first detector comprises PET event detection units for transmitting indications of scintillation events occurring within said first detector to said switchable trigger detection unit;
said second detector comprises PET event detection units for transmitting indications of scintillation events occurring within said second detector to said switchable trigger detection unit; and wherein
said switchable trigger detection unit comprises a coincidence detector coupled to said indications of scintillation events occurring within said first detector and coupled to said indications of scintillation events occurring within said second detector, said coincidence detector for generating a coincidence signal upon coincidence of said scintillation events occurring within said first detector and said indications of scintillation events occurring within said second detector.

9. A nuclear camera system as described in claim 8 wherein:
said first detector comprises SPECT event detection units for transmitting indications of scintillation events occurring within said first detector to said switchable trigger detection unit; and
said second detector comprises SPECT event detection units for transmitting indications of scintillation events occurring within said second detector to said switchable trigger detection unit.

10. A nuclear camera system as described in claim 9 wherein said switchable trigger detection unit further comprises:
a first multiplexer receiving a select signal and receiving an input from said SPECT event detection units of said first detector and receiving an input from said coincidence detector;
a second multiplexer receiving said select signal and receiving an input from said SPECT event detection units of said second detector and receiving an input from said coincidence detector; and
wherein said first multiplexer outputs said first valid event trigger signal to said first detector and wherein said second multiplexer outputs said second valid event trigger signal to said second detector.

11. A trigger signal generator switchable between PET and SPECT operational modes, said trigger signal generator comprising:
first SPECT event detection circuitry for generating a first trigger signal upon detection of a scintillation event within a first detector;
second SPECT event detection circuitry for generating a second trigger signal upon detection of a scintillation event within a second detector;
first PET event detection circuitry for generating a third trigger signal upon detection of a scintillation event within said first detector;
second PET event detection circuitry for generating a fourth trigger signal upon detection of a scintillation event within said second detector;
a coincidence detector coupled to said third and fourth trigger signals for generating a coincidence signal upon coincidence of said third and fourth trigger signals; and
a switchable unit receiving said coincidence signal and said first and second trigger signals, said switchable unit for providing said first and second detector with said coincidence signal when in said PET operational mode and for providing said first and second detector with said first and second trigger signals, respectively, when in said SPECT operational mode.

12. A trigger signal generator as described in claim 11 wherein said switchable unit receives a select signal indicating either said PET or said SPECT operational mode.

13. A trigger signal generator as described in claim 12 wherein said switchable unit further comprises:
a first multiplexer receiving said select signal and said first trigger signal and said coincidence signal and outputting a valid event signal to said first detector;
a second multiplexer receiving said select signal and said second trigger signal and said coincidence signal and outputting a valid event signal to said second detector;
said first multiplexer outputting said first trigger signal as said valid event signal to said first detector when in said SPECT operational mode and outputting said coincidence signal as said valid event signal to said first detector when in said PET operational mode; and
said second multiplexer outputting said second trigger signal as said valid event signal to said second detector when in said SPECT operational mode and outputting said coincidence signal as said valid event signal to said second detector when in said PET operational mode.

14. A trigger signal generator as described in claim 11 wherein said switchable unit triggers said first and second detectors to record a detected scintillation event, including accumulating energy of said scintillation event and localizing said scintillation event.

15. A trigger signal generator as described in claim 11 wherein said first and second SPECT event detection circuitry utilize a leading edge discriminator and wherein said first and second PET event detection circuitry utilize a constant fraction discriminator.

16. For a channel circuit associated with a photomultiplier of a scintillation detector, an accumulator circuit comprising:

a programmable register for containing a programmable integration period;

an analog to digital converter for receiving a first signal representative of energy detected by said photomultiplier as a result of a scintillation event and for digitizing said first signal to generate a digital signal therefrom;

a first integrator for integrating said digital signal over said programmable integration period to arrive at a result;

a memory circuit for containing said result of said first integrator.

17. An accumulator circuit as described in claim 16 further comprising a programming unit for programming a first integration period into said programmable register such that said first integrator is optimized for periods of higher count rate and for programming a second integration period into said programmable register such that said first integrator is optimized for periods of lower count rate.

18. An accumulator circuit as described in claim 17 wherein a received trigger signal initiates an integration interval and further comprising:

a counter circuit for counting an interval from said trigger signal;

a comparator circuit coupled to said counter circuit and coupled to said programmable register, said comparator circuit generating an output signal when said counter circuit reaches said programmable integration period; and said memory circuit for latching in said result upon generation of said output signal from said comparator circuit.

19. An accumulator circuit as described in claim 16 further comprising:

a programming unit for programming said programmable integration period such that said first integrator is optimized first a PET operational mode.

20. An accumulator circuit as described in claim 19 further comprising:

a programming unit for programming said programmable integration period such that said first integrator is optimized for a SPECT operational mode.

21. An event detection apparatus comprising:

(a) at least a pair of scintillation detectors for reporting a pair of events occurring in coincidence for PET imaging and for reporting events individually for SPECT imaging, each of said pair of scintillation detectors comprising:

(i) an analog to digital converter for receiving a channel signal representative of energy detected by a photomultiplier as a result of a scintillation event and for digitizing said channel signal to generate a digital signal therefrom;

(ii) a first integrator circuit coupled to receive said digital signal and for integrating said digital signal over a first time period of a programmable integration interval;

(iii) a second integrator circuit coupled to said digital signal and for integrating said digital signal over a second time period of said programmable integration duration; and (iv) a programmable register for containing a value representative of said programmable integration duration; and (b) a mechanism for recording said events.

22. An event detection apparatus as described in claim 21 further comprising a programming unit for programming a first value into said programmable register such that said first and second integrator circuits are optimized for periods of higher count rate detection and for programming a second value into said programmable register such that said first and second integrator circuits are optimized for periods of lower count rate detection.

23. An event detection apparatus as described in claim 21 wherein a received trigger signal initiates an integration interval and further comprising:

a first counter circuit for counting an interval from said trigger signal;

a first comparator circuit coupled to said first counter circuit and coupled to said programmable register, said first comparator circuit generating a first output signal when said first counter circuit reaches said programmable integration interval;

a memory circuit for latching in a result of said first integrator circuit upon generation of said first output signal from said first comparator circuit.

a second counter circuit for counting an interval from said trigger signal;

a second comparator circuit coupled to said second counter circuit and coupled to said programmable register, said second comparator circuit generating a second output signal when said second counter circuit reaches said programmable integration interval; and said memory circuit for latching in a result of said second integrator circuit upon generation of said second output signal from said second comparator circuit.

24. An event detection apparatus as described in claim 21 wherein said first integrator circuit and said second integrator circuit operate such that said first time period and said second time period overlap.

25. An event detection apparatus as described in claim 21 further comprising a trigger circuit for generating a trigger pulse upon detection of a gamma event and wherein said first integrator circuit and said second integrator circuit are independently initiated by said trigger circuit.

26. An event detection apparatus as described in claim 25 further comprising a two stage latch circuit coupled to receive output data from both of said first integrator circuit and said second integrator circuit, said two stage latch circuit for containing integrated results of said digital signal.

27. An event detection apparatus as described in claim 26 further comprising a multiplexer circuit for selecting an output between said first integrator circuit and said second integrator circuit and for supplying said output to said two stage latch circuit.

28. An event detection apparatus as described in claim 26 wherein said two stage latch circuit comprises:

a first memory stage for receiving output data from both of said first integrator circuit and said second integrator circuit; and a second memory stage coupled to said first memory stage for receiving output data from said first stage when said first stage receives said output data from said first integrator circuit or said second integrator circuit.

29. In a nuclear medicine camera, an apparatus for generating a photomultiplier cluster, said apparatus comprising:
at least a pair of scintillation detectors for reporting a pair of events occurring in coincidence for PET imaging and for reporting events individually for SPECT imaging, each of said pair of scintillation detectors comprising:
an array of photomultipliers wherein individual photomultipliers generate channel signals,
integration circuitry integrating said channel signals from each scintillation detector responsive to a gamma event and generating integration results therefrom;
peak circuitry for determining a peak photomultiplier based on said integration results and for generating a signal indicative of said peak photomultiplier; and
cluster circuitry addressed by said peak circuitry and responsive to said signal indicative of said peak photomultiplier for generating a photomultiplier cluster associated with said peak photomultiplier, said cluster circuitry containing separate photomultiplier clusters for individual photomultipliers of said array of photomultipliers and wherein said cluster circuitry also generates a cluster type signal responsive to said signal indicative of said peak photomultiplier wherein said cluster type signal indicates a geometric type of said photomultiplier cluster.

30. An apparatus as described in claim 29 wherein said photomultiplier cluster comprises a set of photomultiplier indicators and further comprising:
a sequencer circuit coupled to said cluster circuitry, said sequencer circuit for addressing said cluster circuitry such that individual photomultiplier indicators of said photomultiplier cluster are sequentially output from said cluster circuitry; and
weight circuitry responsive to (1) said photomultiplier indicators and (2) said cluster type signal, said weight circuitry for generating individual coordinate weight value signals associated with individual photomultipliers of said photomultiplier cluster.

31. An apparatus as described in claim 30 wherein said photomultiplier cluster comprises a set of photomultiplier indicators and further comprising:
a buffer storage for storing integrated results of said photomultiplier cluster, said buffer storage addressed by photo multiplier indicators output from said cluster circuitry; and
centroid computation circuitry coupled to receive output integration results from said buffer storage and coupled to receive said individual coordinate weight value signals associated with individual photomultipliers of said photomultiplier cluster, and in response thereto, said centroid computation circuitry for generating a two dimensional spatial coordinate of said gamma event.

32. An apparatus as described in claim 29 wherein said cluster type signal indicates between a normal cluster type, an edge cluster type and a corner cluster type of said photomultiplier cluster.

33. An apparatus as described in claim 29 wherein said photomultiplier cluster comprises a set of photomultiplier indicators and further comprising a sequencer circuit coupled to said cluster circuitry, said sequencer circuit for addressing said cluster circuitry such that individual photomultiplier indicators of said photomultiplier cluster are sequentially output from said cluster circuitry.

34. An apparatus as described in claim 33 wherein said cluster circuitry comprises a programmable memory circuit addressed by said signal indicative of said peak photomultiplier and said sequencer circuit.

35. An apparatus as described in claim 29 further comprising a user selectable operational mode between said PET imaging and said SPECT imaging wherein said photomultiplier cluster that is output from said cluster circuitry is responsive to said operational mode.

36. An apparatus as described in claim 35 wherein said cluster circuitry outputs photomultiplier clusters in sets of seven or less photomultipliers each, provided said operational mode is set for said PET imaging and wherein said cluster circuitry outputs photomultiplier clusters in sets of more than seven photomultipliers each, provided said operational mode is set for said SPECT imaging.

37. In a nuclear medicine camera, an apparatus for generating a photomultiplier cluster, said apparatus comprising:
(a) a user selectable operational mode between PET imaging and SPECT imaging;
(b) at least a pair of scintillation detectors for reporting a pair of events occurring in coincidence for said PET imaging and for reporting events individually for said SPECT imaging, each of said pair of scintillation detectors comprising:
an array of photomultipliers, individual photomultipliers for generating output channel signals indicative of energy detected by said individual photomultipliers;
peak circuitry coupled to receive said output channel signals and for determining a peak photomultiplier of said array of photomultipliers; and
cluster circuitry addressed by said peak circuitry and responsive to said signal indicative of said peak photomultiplier for generating a photomultiplier cluster associated with said peak photomultiplier, said cluster circuitry containing separate photomultiplier clusters for each peak photomultiplier, said cluster circuitry for providing photomultiplier clusters of a first size provided said operational mode is said PET imaging and for providing photomultiplier clusters of a second size provided said operational mode is said SPECT imaging; and
(c) a mechanism for recording said events detected by said pair of scintillation detectors.

38. An apparatus as described in claim 37 wherein said first size is relatively smaller than said second size.

39. An apparatus as described in claim 37 wherein said first size is 7 or less photomultipliers per cluster and wherein said second size is more than 7 photomultipliers per cluster.

40. In a nuclear medicine camera, an apparatus for generating a trigger signal indicative of an event, said apparatus comprising:
(a) a user selectable operational mode between PET imaging and SPECT imaging;
(b) at least a pair of scintillation detectors for reporting a pair of events occurring in coincidence for said PET imaging and for reporting events individually for said SPECT imaging, each of said pair of scintillation detectors comprising:
an array of photomultipliers, individual photomultipliers for generating output channel signals indicative of energy detected by said individual photomultipliers, wherein said array of photomultipliers is divided into zones;
a first plurality of event detection circuits wherein each of said event detection circuits receive channel signals from a particular zone of said zones of said array of photomultipliers; and a first trigger circuit coupled to said first plurality of event detection circuits for generating a trigger signal upon receiving an event indication from any event detection circuit of said first plurality of event detection circuits.

41. An apparatus as described in claim 40 wherein each of said event detection circuits of said first plurality comprise a constant fraction discriminator for generating an event indication.

42. An apparatus as described in claim 40 further comprising:

an AND gate coupled to each first trigger circuit of said pair of scintillation detectors, said AND gate generating a valid event trigger signal upon receiving a pair of trigger signals within a coincidence window from each first trigger circuit of said pair of scintillation detectors.

43. An apparatus as described in claim 40 wherein said pair of scintillation detectors further comprise:

a second plurality of event detection circuits wherein each of said event detection circuits of said second plurality receive channel signals from a particular zone of said zones of said array of photomultipliers; and a second trigger circuit coupled to said second plurality of event detection circuits for generating a trigger signal upon receiving an event indication from any event detection circuit of said second plurality of event detection circuits.

44. An apparatus as described in claim 43 wherein each of said event detection circuits of said second plurality comprise a leading edge discriminator for generating an event indication.

45. An apparatus as described in claim 43 further comprising:

an OR gate coupled to each second trigger circuit of said pair of scintillation detectors, said OR gate generating a valid event trigger signal upon receiving a trigger signal from either of said second trigger circuits of said pair of scintillation detectors.

46. In a nuclear medicine camera, an apparatus for optimizing said camera for either PET or SPECT imaging modes, said apparatus comprising:

a switchable operational mode between said PET imaging and said SPECT imaging modes;

at least a pair of scintillation detectors for reporting a pair of events occurring in coincidence for said PET imaging mode and for reporting events individually for said SPECT imaging mode, said pair of scintillation detectors for rotating about a patient and for collecting projection image data under said PET or SPECT imaging modes;

programmable integration circuitry coupled to channel signals output from photomultiplier tubes of said pair of scintillation detectors, said programmable circuitry for integrating said channel signals over a first integration period or over a second integration period in response to said operational mode;

a programmable trigger circuit coupled to event detection logic within said pair of scintillation detectors, said programmable trigger circuit for generating valid event trigger signals based on coincidence between said pair of scintillation detectors or not based on coincidence between said pair of scintillation detectors in response to said operational mode; and a programmable photomultiplier cluster circuit responsive to values over said channel signals, said programmable photomultiplier cluster for utilizing a cluster of a first size for localizing detected events and for utilizing a cluster of a second size for localizing detected events in response to said operational mode.

47. An apparatus as described in claim 46 wherein first integration period is utilized for said PET imaging mode and wherein said second integration period is utilized for said SPECT imaging mode and wherein said first integration period is shorter in length over said second integration period.

48. An apparatus as described in claim 47 wherein said programmable trigger circuit utilizes coincidence between said pair of scintillation detectors for generating said valid event trigger signals when in said PET imaging mode and said programmable trigger circuit does not utilize coincidence between said pair of scintillation detectors for generating said valid event trigger signals when in said SPECT imaging mode.

49. An apparatus as described in claim 48 wherein said first size of said programmable photomultiplier cluster is seven photomultipliers or less and is utilized when in said PET imaging mode and wherein said second size is more than seven photomultipliers and is utilized when in said SPECT imaging mode.

* * * * *

UNITED STATES PATENT AND TRADEMARK OFFICE
Certificate

Patent No. 5,585,637                  Patented: December 17, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Hugo Bertelsen, Horace H. Hines, Matthew J. Murphy, Peter Nellemann, Donald R. Wellnitz, Gerd Muehllehner and Michael Geagan.

Signed and Sealed this Fifteenth Day of June, 1999.

BRIAN W. BROWN
*Special Program Examiner*
Technology Center 2800
Semiconductors, Electrical
and Optical Systems